(12) United States Patent
Wong et al.

(10) Patent No.: US 11,298,354 B2
(45) Date of Patent: Apr. 12, 2022

(54) METHODS OF USE AND PHARMACEUTICAL COMBINATIONS OF HDAC INHIBITORS WITH BET INHIBITORS

(71) Applicants: DANA-FARBER CANCER INSTITUTE, INC., Boston, MA (US); ACETYLON PHARMACEUTICALS, INC., Boston, MA (US)

(72) Inventors: Kwok-kin Wong, Boston, MA (US); Yan Liu, Boston, MA (US); Dennis O. Adeegbe, Boston, MA (US); Steven Norman Quayle, Brookline, MA (US)

(73) Assignees: DANA-FARBER CANCER INSTITUTE, INC., Boston, MA (US); ACETYLON PHARMACEUTICALS, INC., Boston, MA (US)

( * ) Notice: Subject to any disclaimer, the term of this patent is extended or adjusted under 35 U.S.C. 154(b) by 255 days.

(21) Appl. No.: 16/305,567

(22) PCT Filed: Jun. 9, 2017

(86) PCT No.: PCT/US2017/036847
§ 371 (c)(1),
(2) Date: Nov. 29, 2018

(87) PCT Pub. No.: WO2017/214565
PCT Pub. Date: Dec. 14, 2017

(65) Prior Publication Data
US 2020/0323848 A1    Oct. 15, 2020

Related U.S. Application Data

(60) Provisional application No. 62/348,054, filed on Jun. 9, 2016.

(51) Int. Cl.
*A61K 31/505* (2006.01)
*A61P 35/00* (2006.01)
*A61K 31/437* (2006.01)
*A61K 31/551* (2006.01)

(52) U.S. Cl.
CPC .......... *A61K 31/505* (2013.01); *A61K 31/437* (2013.01); *A61K 31/551* (2013.01); *A61P 35/00* (2018.01)

(58) Field of Classification Search
CPC .. A61K 31/505; A61K 31/437; A61K 31/551; A61P 35/00
See application file for complete search history.

(56) References Cited

U.S. PATENT DOCUMENTS

| | | | |
|---|---|---|---|
| 2011/0300134 A1* | 12/2011 | van Duzer | A61P 37/06 424/133.1 |
| 2013/0225543 A1* | 8/2013 | Jones | A61K 45/06 514/171 |
| 2014/0011767 A1* | 1/2014 | Yang | A61P 35/00 514/64 |
| 2014/0357512 A1* | 12/2014 | Yang | G01N 33/57496 506/9 |
| 2015/0099744 A1* | 4/2015 | Tamang | A61P 35/00 514/234.2 |
| 2015/0105358 A1 | 4/2015 | Quayle et al. | |
| 2015/0105383 A1* | 4/2015 | Quayle | A61K 31/505 514/234.2 |
| 2015/0105384 A1* | 4/2015 | Jones | A61K 31/5377 514/235.2 |
| 2015/0105409 A1* | 4/2015 | Quayle | A61K 31/519 514/262.1 |
| 2015/0150871 A1* | 6/2015 | Quayle | A61K 45/06 424/278.1 |
| 2015/0176076 A1* | 6/2015 | Yang | A61P 43/00 514/275 |
| 2016/0030458 A1 | 2/2016 | Jones et al. | |
| 2016/0339022 A1* | 11/2016 | Tamang | A61K 31/5377 |
| 2016/0355486 A1* | 12/2016 | Seyedi | C07D 239/42 |
| 2017/0001965 A1* | 1/2017 | van Duzer | A61P 35/00 |
| 2017/0114023 A1* | 4/2017 | Golonzhka | A61K 31/495 |
| 2019/0046529 A1* | 2/2019 | Quayle | A61P 35/00 |
| 2019/0209559 A1* | 7/2019 | Jones | A61K 31/505 |
| 2019/0262337 A1* | 8/2019 | Moore | A61K 31/635 |
| 2019/0282573 A1* | 9/2019 | Quayle | A61K 31/454 |
| 2019/0282574 A1* | 9/2019 | Quayle | A61K 31/505 |
| 2019/0321361 A1* | 10/2019 | Huang | A61K 31/427 |
| 2020/0046698 A1* | 2/2020 | North | A61K 31/5377 |

FOREIGN PATENT DOCUMENTS

WO    2015168587 A1    11/2015

OTHER PUBLICATIONS

Carew; Blood 2015; 126, 3022. doi: https://doi.org/10.1182/blood.V126.23.3022.3022 (Year: 2015).*
Ghoshal; Expert Opinion on Therapeutic Patents, 2016, 26, 505-522. DOI: 10.1517/13543776.2016.1159299 (Year: 2016).*
Heinemann; Oncotarget, 2015, 6, 21507-21521. doi: 10.18632/oncotarget.4242. (Year: 2015).*
Lenhart; Mol Cancer Ther, 2015, 14, 2167-2174. DOI: 10.1158/1535-7163.MCT-15-0037 (Year: 2015).*
Ping; Journal of Nanjing Medical University, 2015,8, 1092-1095. DOI: 10.7655/NYDXBNS20150808 (Year: 2015).*
Santo; Blood, 2012, 119, 2579-2589. doi: https://doi.org/10.1182/blood-2011-10-387365 (Year: 2012).*

(Continued)

*Primary Examiner* — Daniel R Carcanague
(74) *Attorney, Agent, or Firm* — Lathrop GPM LLP; Brian C. Trinque

(57) ABSTRACT

The disclosure relates to pharmaceutical combinations comprising an HDAC6 selective inhibitor and a BET inhibitor for the treatment of cancer in a subject in need thereof. Also provided herein are methods for treating cancer in a subject in need thereof, comprising administering to the subject an effective amount of an HDAC6 selective inhibitor and a BET inhibitor.

11 Claims, 34 Drawing Sheets

(56) References Cited

OTHER PUBLICATIONS

Shahbazi; Clin Cancer Res, 2016, 22, 2534-2544. DOI: 10.1158/1078-0432.CCR-15-1666 (Year: 2016).*
Wang; European Journal of Medicinal Chemistry, 2018, 143, 1406-1418. DOI: 10.1016/j.ejmech.2017.10.040 (Year: 2018).*
Extended European Search Report in Application EP17811118, dated Dec. 12, 2019. 9 pages (Year: 2019).*
Perez-Salvia; Epigenetics, 2017, 12, 323-339. DOI:10.1080/15592294.2016.1265710 (Year: 2017).*
Wang, Oncology Reports 2016, 36, 589-597. DOI: 10.3892/or.2016.4811 (Year: 2016).*
Lwin et al. (2013) "A microenvironment-mediated c-Myc/miR-548m/HDAC6 amplification loop in non-Hodgkin B cell lymphomas," J. Clin. Invest. 123(11):4612-4626.
Depew et al. (2012) "Pulmonary Mantle Cell Lymphoma: A Rare Manifestation of an Uncommon Condition," Rare Tumors 4(11): 30-31; abstract.

* cited by examiner

METHODS OF USE AND PHARMACEUTICAL COMBINATIONS OF HDAC INHIBITORS WITH BET INHIBITORS

CROSS-REFERENCE TO RELATED APPLICATIONS

This application is a 35 U.S.C. § 371 filing of International Application No. PCT/US2017/036847, filed on Jun. 9, 2017, which claims priority to U.S. Provisional Application Ser. No. 62/348,054, filed Jun. 9, 2016, which is incorporated herein by reference in its entirety.

BACKGROUND

Histone deacetylase (HDAC) inhibition can cause cancer cell growth arrest. However, pan-HDAC inhibition leads to significant adverse effects, and an alternative HDAC inhibition profile is desirable, particularly in combination with other therapeutic agents.

HDAC6 is a Class IIb HDAC and is known to remove acetyl groups from many cellular proteins, including α-tubulin and HSP90. It has been reported that HSP90 hyperacetylation destabilizes its target proteins, including ER and EGFR. Inhibitors of HDAC6 have demonstrated anti-cancer proliferative activity in various cancer types. Blocking HDAC6 activity has been shown to cause cancer cell growth inhibition through various mechanisms.

Bromodomain and extra-terminal motif (BET) proteins, including BRD2, BRD3, BRD4, and BRDT, contain a bromodomain that recognizes acetylated lysine residues, for example, on the N-terminal tails of histones. BET inhibitors bind the bromodomains of BET proteins and alter cellular epigenetic and transcriptional programs. Inhibitors of BET proteins have shown therapeutic effects in various cancer types.

Due to the dose-limiting toxicities of current pan-selective HDAC inhibitors, there is an ongoing need for improved methods for the treatment of cancer.

SUMMARY

In order to provide alternative efficacious and less toxic cancer treatments, provided herein are methods for the treatment of cancer, and pharmaceutical combinations comprising an HDAC inhibitor and a BET inhibitor. The pharmaceutical combinations and methods disclosed herein are well tolerated and do not exhibit the dose-limiting toxicities of prior therapies.

In one aspect, provided herein are methods for treating cancer in a subject in need thereof, comprising administering to the subject a therapeutically effective amount of an HDAC6 selective inhibitor and a therapeutically effective amount of a BET inhibitor. In some embodiments, the HDAC6 selective inhibitor is a compound of Formula I:

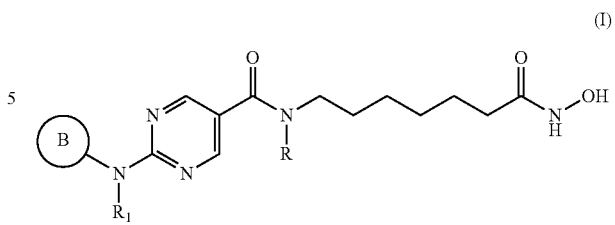

(I)

or a pharmaceutically acceptable salt thereof,
wherein,
ring B is aryl or heteroaryl;
$R_1$ is an aryl or heteroaryl, each of which may be optionally substituted by OH, halo, or $C_{1-6}$-alkyl; and
R is H or $C_{1-6}$-alkyl.

In other embodiments, $R^1$ is an aryl or heteroaryl. In another embodiment, the compound of Formula I is:

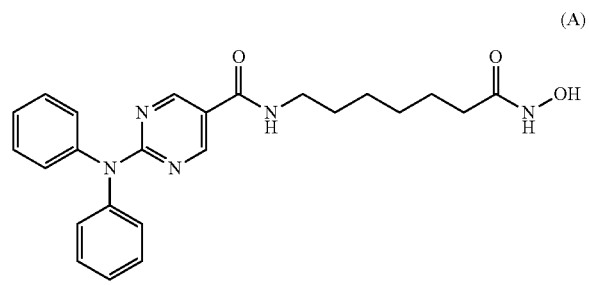 [SMILES: O=C(CCCCCCNC(=O)c1cnc(N(c2ccccc2)c2ccccc2)nc1)NO]

(A)

or a pharmaceutically acceptable salt thereof.

In a further embodiment, $R^1$ is an aryl or heteroaryl, each of which is substituted by halo. In yet another embodiment, the compound of Formula I is:

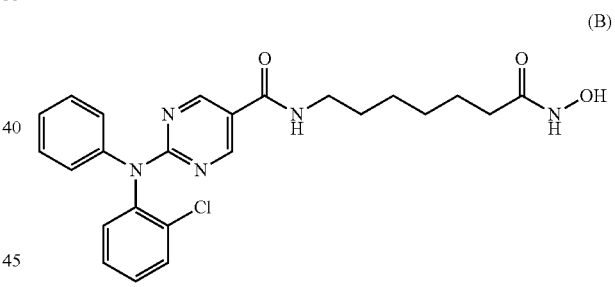

(B)

or a pharmaceutically acceptable salt thereof.

In some embodiments, the HDAC6 selective inhibitor is a compound of Formula II:

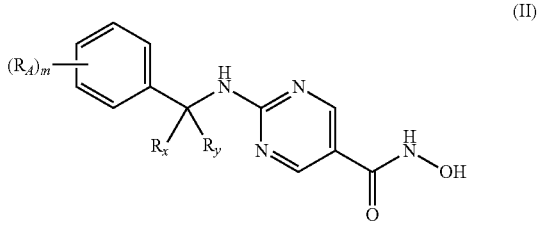

(II)

or a pharmaceutically acceptable salt thereof,
wherein,
$R_x$ and $R_y$, together with the carbon to which each is attached, form a cyclopropyl, cyclobutyl, cyclopentyl, cyclohexyl, cycloheptyl, or cyclooctyl;
each $R_A$ is independently $C_{1-6}$-alkyl, $C_{1-6}$-alkoxy, halo, OH, —NO$_2$, —CN, or —NH$_2$; and
m is 0, 1, or 2.

In another embodiment, the compound of Formula II is:

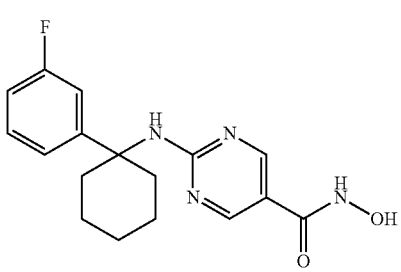
(C)

or a pharmaceutically acceptable salt thereof. In still another embodiment, the compound of Formula II is:

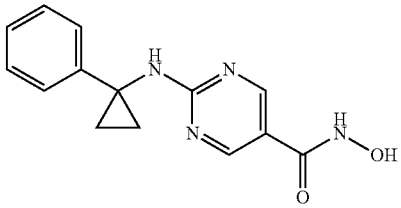
(D)

or a pharmaceutically acceptable salt thereof. In yet another embodiment, the HDAC6 selective inhibitor is Tubastatin A, or a pharmaceutically acceptable salt thereof.

In other embodiments, the BET inhibitor is selected from the group consisting of ABBV-075, BAY1238097, BMS986158, bromosporine, CBP30, CPI-203, CPI-0610, FT-1101, GSK2820151, I-BET151, I-BET726, I-BET-762 (GSK525762), INCB054329, INCB057643, ISOX DUAL, JQ1, LY294002, LY303511, MS436, MK8628 (OTX-015), OF-1, OXF BD 02, PFI-1, PFI-3, PF-6405761, RVX-208, TEN-010, XD 14, and ZEN003694, or a pharmaceutically acceptable salt thereof. In another embodiment, the BET inhibitor is JQ1.

In yet another embodiment, the HDAC6 selective inhibitor or the BET inhibitor are administered at a sub-therapeutic dose. In still another embodiment, the HDAC6 selective inhibitor induces apoptosis of cancer cells.

In another aspect, provided herein are pharmaceutical combinations comprising a therapeutically effective amount of an HDAC6 selective inhibitor, or a pharmaceutically acceptable salt thereof, and a therapeutically effective amount of a BET inhibitor, or a pharmaceutically acceptable salt thereof. In one embodiment, the HDAC6 selective inhibitor is a compound of Formula I. In another embodiment, the compound of Formula I is Compound A, or a pharmaceutically acceptable salt thereof. In yet another embodiment, the compound of Formula I is Compound B, or a pharmaceutically acceptable salt thereof. In other embodiments, the HDAC6 selective inhibitor is a compound of Formula II. In a further embodiment, the compound of Formula II is Compound C, or a pharmaceutically acceptable salt thereof. In still another embodiment, the compound of Formula II is Compound D, or a pharmaceutically acceptable salt thereof. In yet another embodiment, the HDAC6 selective inhibitor is Tubastatin A, or a pharmaceutically acceptable salt thereof.

In some embodiments, the BET inhibitor is selected from the group consisting of ABBV-075, BAY1238097, BMS986158, CPI-203, CPI-0610, FT-1101, GSK2820151, GSK525762, I-BET151, I-BET726, I-BET-762, INCB054329, INCB057643, JQ1, MS436, OF-1, MK8628, PFI-3, PF-6405761, RVX-208, TEN-010, and ZEN003694, or a pharmaceutically acceptable salt thereof. In another embodiment, the BET inhibitor is JQ1, or a pharmaceutically acceptable salt thereof. In certain embodiments, the pharmaceutical combination further comprises a pharmaceutically acceptable carrier.

In another aspect, provided herein are pharmaceutical combinations comprising a therapeutically effective amount of a compound of Formula I, or a pharmaceutically acceptable salt thereof, and a therapeutically effective amount of JQ1, or a pharmaceutically acceptable salt thereof.

In another aspect, provided herein are pharmaceutical combinations comprising a therapeutically effective amount of Compound A, or a pharmaceutically acceptable salt thereof, and a therapeutically effective amount of JQ1, or a pharmaceutically acceptable salt thereof.

In another aspect, provided herein are pharmaceutical combinations comprising a therapeutically effective amount of Compound B, or a pharmaceutically acceptable salt thereof, and a therapeutically effective amount of JQ1, or a pharmaceutically acceptable salt thereof.

In another aspect, provided herein are pharmaceutical combinations comprising a therapeutically effective amount of a compound of Formula II, or a pharmaceutically acceptable salt thereof, and a therapeutically effective amount of JQ1, or a pharmaceutically acceptable salt thereof.

In another aspect, provided herein are pharmaceutical combinations comprising a therapeutically effective amount of Compound C, or a pharmaceutically acceptable salt thereof, and a therapeutically effective amount of JQ1, or a pharmaceutically acceptable salt thereof.

In another aspect, provided herein are pharmaceutical combinations comprising a therapeutically effective amount of Compound D, or a pharmaceutically acceptable salt thereof, and a therapeutically effective amount of JQ1, or a pharmaceutically acceptable salt thereof.

In other embodiments, provided herein are uses of the pharmaceutical combinations disclosed herein for the manufacture of a pharmaceutical preparation or medicament for the treatment of cancer. In some embodiments, the cancer is lung cancer.

In another embodiment, provided herein is a pharmaceutical combination wherein the HDAC6 selective inhibitor and the BET inhibitor are together formulated as a single formulation. In yet another embodiment, provided herein is a pharmaceutical combination wherein the HDAC6 selective inhibitor and the BET inhibitor are each formulated as separate formulations.

In other embodiments, provided herein are methods for decreasing cell viability of cancer cells in a subject with cancer by administering a pharmaceutical combination disclosed herein. In another embodiment, provided herein are methods for synergistically increasing apoptosis of cancer cells in a subject with cancer by administering to a subject a pharmaceutical combination disclosed herein. In still another embodiment, provided herein are methods for reducing circulating regulatory T lymphocytes (Tregs) in a subject with cancer by administering to the subject a therapeutically effective amount of an HDAC6 selective inhibitor, a therapeutically effective amount of a BET inhibitor, or a therapeutically effective amount of a pharmaceutical combination disclosed herein. In some embodiments, the Tregs are CD4+FOXP3+Tregs. In yet another embodiment, provided herein are methods for altering expression of antigen presenting complexes in a subject with cancer by administering to the subject a therapeutically effective amount of an HDAC6 selective inhibitor, or a therapeutically effective amount of a pharmaceutical combination disclosed herein. In a further embodiment, provided herein are methods for treating cancer by increasing costimulatory function of antigen presenting cells in a subject by administering to the subject a therapeutically effective amount of an HDAC6 selective inhibitor, or a therapeutically effective amount of a pharmaceutical combination disclosed herein. In some embodiments, the presenting protein is CD86, and the expression is increased. In another embodiment, the presenting protein is MHC II, and the expression is increased. In a further embodiment, provided herein are methods for treating cancer by activating T cells in a subject by administering to the subject a therapeutically effective amount of an HDAC6 selective inhibitor, or a therapeutically effective amount of a pharmaceutical combination disclosed herein. In some embodiments, expression of CD69 is increased. In another embodiment, the T cells are CD69 positive CD4+ T cells. In another embodiment, the T cells are CD69 positive CD8+ T cells.

In another aspect, provided herein is a method for decreasing cell proliferation of cancer cells in a subject with cancer by administering to the subject a therapeutically effective amount of a pharmaceutical combination disclosed herein. In still another aspect, the disclosure relates to methods for upregulating lymphocyte functional activity in a subject in need thereof, comprising administering to the subject a therapeutically effective amount of an HDAC6 selective inhibitor, or a therapeutically effective amount of a pharmaceutical combination disclosed herein. In some embodiments, the lymphocyte is a T cell. In another embodiment, the functional activity is transient TCR-independent activation.

In certain embodiments of the foregoing methods, the cancer is lung cancer. In another embodiment of the foregoing methods, the lung cancer is non-small cell lung cancer, small cell lung cancer, or lung carcinoid tumor. In a further embodiment of the foregoing methods, the cancer is non-small cell lung cancer.

In other embodiments of the foregoing methods, the HDAC6 selective inhibitor and the BET inhibitor are together formulated as a single formulation. In another embodiment of the foregoing methods, the HDAC6 selective inhibitor and the BET inhibitor are each formulated as separate formulations. In still another embodiment of the foregoing methods, the HDAC6 selective inhibitor and the BET inhibitor are administered at substantially the same time. In yet another embodiment of the foregoing methods, the HDAC6 selective inhibitor and the BET inhibitor are administered at different times.

In some embodiments of the foregoing methods, the cancer is resistant or refractory cancer.

In another aspect provided herein is a method for decreasing cell proliferation of cancer cells in a subject with cancer comprising administering to the subject a therapeutically effective amount of a pharmaceutical combination comprising a compound of Formula I, or a pharmaceutically acceptable salt thereof, and JQ1, or a pharmaceutically acceptable salt thereof.

In another aspect provided herein is a method for decreasing cell proliferation of cancer cells in a subject with cancer comprising administering to the subject a therapeutically effective amount of a pharmaceutical combination comprising Compound A, or a pharmaceutically acceptable salt thereof, and JQ1, or a pharmaceutically acceptable salt thereof.

In another aspect provided herein is a method for decreasing cell proliferation of cancer cells in a subject with cancer comprising administering to the subject a therapeutically effective amount of a pharmaceutical combination comprising Compound B, or a pharmaceutically acceptable salt thereof, and JQ1, or a pharmaceutically acceptable salt thereof.

In another aspect provided herein is a method for decreasing cell proliferation of cancer cells in a subject with cancer comprising administering to the subject a therapeutically effective amount of a pharmaceutical combination comprising a compound of Formula II, or a pharmaceutically acceptable salt thereof, and JQ1, or a pharmaceutically acceptable salt thereof.

In another aspect provided herein is a method for decreasing cell proliferation of cancer cells in a subject with cancer comprising administering to the subject a therapeutically effective amount of a pharmaceutical combination comprising Compound C, or a pharmaceutically acceptable salt thereof, and JQ1, or a pharmaceutically acceptable salt thereof.

In another aspect provided herein is a method for decreasing cell proliferation of cancer cells in a subject with cancer comprising administering to the subject a therapeutically effective amount of a pharmaceutical combination comprising Compound D, or a pharmaceutically acceptable salt thereof, and JQ1, or a pharmaceutically acceptable salt thereof.

Other objects, features, and advantages will become apparent from the following detailed description. The detailed description and specific examples are given for illustration only because various changes and modifications within the spirit and scope of the disclosure will become apparent to those skilled in the art from this detailed description. Further, the examples demonstrate the principle of the disclosure.

DETAILED DESCRIPTION

Figure 1A:
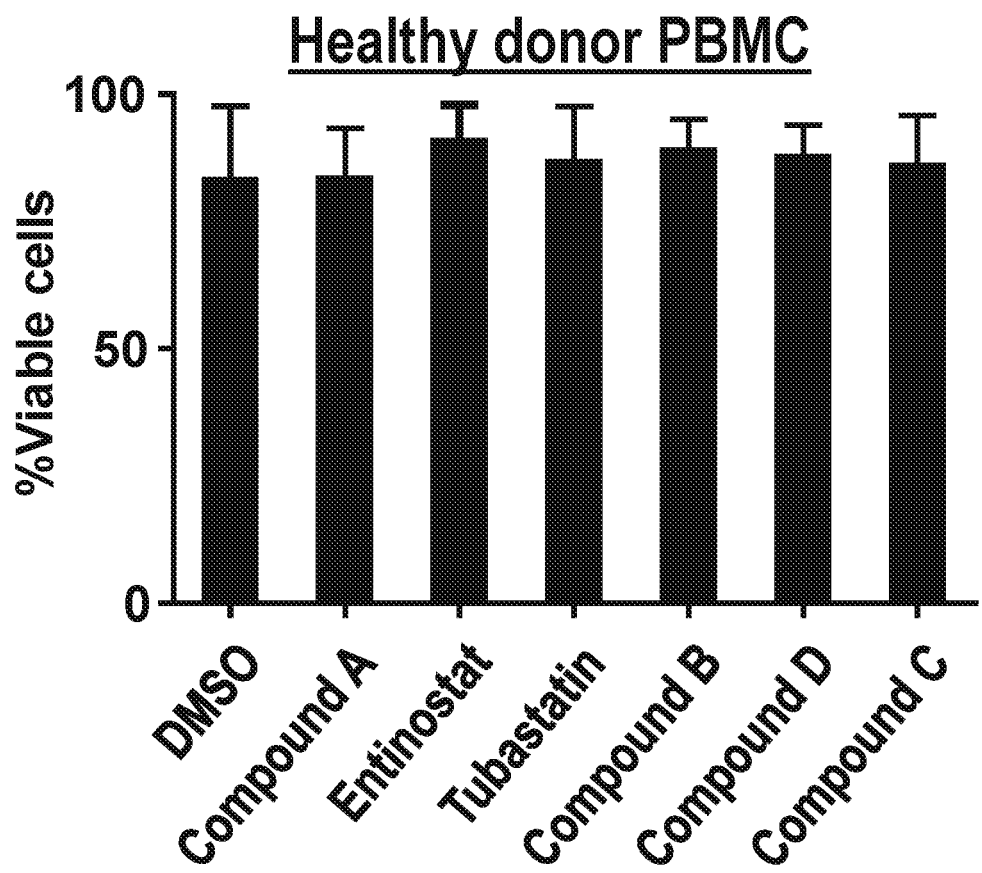
FIG. 1A shows the percentage of live cells as determined by fraction of total cells that were negative for the live/dead viability dye after culturing peripheral blood mononuclear cells (PBMCs) from healthy donors for 24 hours with the HDAC inhibitors.

The tumor micro-environment contains a variety of stromal/supporting cells, including those of hematopoietic origin. Specific cell types such as T lymphocytes, natural killer (NK) cells, and various myeloid cells have been demonstrated in many investigational models to play diverse roles in shaping the course of the immune response against cancer cells (Adam, J. K. et al., *Immune responses in cancer*. Pharmacol Ther, 2003. 99(1): p. 113-32; Domagala-Kulawik, J., *The role of the immune system in non-small cell lung carcinoma and potential for therapeutic intervention*. Transl Lung Cancer Res, 2015. 4(2): p. 177-90; Quail, D. F. and J. A. Joyce, *Microenvironmental regulation of tumor progression and metastasis*. Nat Med, 2013. 19(11): p. 1423-37). Of particular importance are antigen-presenting cells (APCs), which process tumor-associated antigens (TAAs) and present them to potential tumor-reactive T cells in a process that leads to T cell priming. Despite their potential to generate an anti-tumor response, T cell antigen-specific responses are often inhibited by immune-suppressive cells such as myeloid-derived suppressor cells (MDSCs) and CD4+Foxp3+ regulatory T cells (Facciabene, A. et al., *T-regulatory cells: key players in tumor immune escape and angiogenesis*. Cancer Res, 2012. 72(9): p. 2162-71). In addition to inhibitory cellular mechanisms operative in the tumor microenvironment, cancer cells can evade immune recognition by downregulation of MHC class I on their cell surface or dampen T cell effector function by up-regulating molecules such as PD-L1 which transduce inhibitory signals to T cells. This brings to the forefront the notion that agents that promote positive immunophenotypic and functional changes in immune cells may generate a more permissive tumor microenvironment favoring an enhanced anti-tumor response.

HDACs are a family of enzymes that modulate the expression of genes or their products by removing acetyl groups from histone and non-histone proteins. By so doing, they regulate numerous cellular processes, some of which have been implicated in aspects of tumor development and behavior such as differentiation and cell cycle progression of malignant cells, as well as apoptosis (Haberland, M. et al., *The many roles of histone deacetylases in development and physiology: implications for disease and therapy*. Nat Rev Genet, 2009. 10(1): p. 32-42; Licciardi, P. V. and T. C. Karagiannis, *Regulation of immune responses by histone deacetylase inhibitors*. ISRN Hematol, 2012. 2012: p. 690901; Ropero, S. and M. Esteller, *The role of histone deacetylases (HDACs) in human cancer*. Mol Oncol, 2007. 1(1): p. 19-2). Several studies have been performed to evaluate the relative utility of both pan- and isozyme-selective HDAC inhibitors for cancer therapy (Kroesen, M. et al., *HDAC inhibitors and immunotherapy; a double edged sword?* Oncotarget, 2014. 5(16): p. 6558-72; West, A. C. et al., *The anticancer effects of HDAC inhibitors require the immune system*. Oncoimmunology, 2014. 3(1): p. e27414). Although promising therapeutic outcomes have been demonstrated using pan-HDAC inhibitors, especially when combined with chemotherapy drugs, use of these agents is associated with adverse effects and dose-limiting toxicity in patients. While many translational studies exploring the therapeutic efficacy of HDAC inhibitors have focused on their effects on malignant cells, multiple studies have highlighted the immune-modulatory activity of HDAC inhibitors when used alone or in combination with other immunotherapy agents (Chinnaiyan, P. et al., *Modulation of radiation response by histone deacetylase inhibition*. Int J Radiat Oncol Biol Phys, 2005. 62(1): p. 223-9; Di Fazio, P. et al., *The pan-deacetylase inhibitor panobinostat inhibits growth of hepatocellular carcinoma models by alternative pathways of apoptosis*. Cell Oncol, 2010. 32(4): p. 285-300; Kroesen, 2014; Licciardi, 2012; Ropero, 2007; West, 2014). The pan-HDAC inhibitors have limitations including poor tolerability, particularly in combination with standard of care drugs. For example, the pan-HDAC inhibitor panobinostat causes direct cytotoxic effects via induction of apoptosis in tumor cell lines (Di Fazio, 2010). Beyond direct cancer cell-autonomous killing, murine models of epithelial tumors have shown that class-specific or pan-HDAC inhibitors can alter expression of NKG2D ligands, thus affecting NK cell lytic function against cancer cells. The effects of HDAC inhibitors on the cellular constituents of the tumor immune microenvironment remain poorly understood.

Bromodomain inhibitors are a second class of molecules which alter cellular epigenetic and transcriptional programs through regulating the recognition of acetylated lysine residues by transcriptional machinery. JQ1 is a well-characterized inhibitor of the BET family of bromodomain-containing proteins and may indirectly regulate epigenetic footprints by modulating the interactions of histone acetyl transferases (HATs) and HDACs with transcription factors and proteins involved in gene expression. The effects of BET inhibitors (e.g., JQ1) on tumor-associated immune cells remain largely unknown.

Recent preclinical and clinical data generated with antibodies which target immune checkpoints, namely PD-(L)1 and CTLA4, demonstrate that anti-tumor immunity can be driven in multiple tumor types by targeting inhibitory interactions among T cells, APCs and tumor cell populations. However, while the use of these agents represents a major advance in the treatment of cancer, only a minority of patients respond in most tumor types. In addition, the barriers to response appear diverse and are poorly characterized. The durability of anti tumor immunity is increasingly being appreciated to hinge upon immune cell contributions. As disclosed herein, certain immune-modulatory effects of small molecule epigenetic modulators including non-selective and selective HDAC inhibitors and BET inhibitors were identified. Described herein are remarkable dynamic changes with respect to phenotype and function of T cells and monocytes/macrophages in peripheral tissues as well as in the tumor microenvironment caused by an HDAC6 selective inhibitor (e.g., Compound A). Also described are the Treg-specific effects of a BET inhibitor. A pharmaceutical combination comprising an HDAC6 selective inhibitor (e.g., Compound A) and a BET inhibitor (e.g., JQ1) facilitated a sustained anti-tumor response in immunocompetent genetically engineered mouse models of non-small cell lung cancer (NSCLC). With Compound A demonstrating a favorable safety profile in current clinical trials of hematologic cancers, its utility in combination with bromodomain inhibition represents a rational combination for translational development to augment anti-tumor immune responses by targeting mechanisms other than immune checkpoints.

The present disclosure is directed to methods for treating cancer in a subject in need thereof, comprising administering to the subject a therapeutically effective amount of an HDAC6 selective inhibitor and a therapeutically effective amount of a BET inhibitor. Also provided herein are combination products and pharmaceutical combinations comprising an HDAC6 selective inhibitor (e.g., a compound of Formula I or Formula II) and a BET inhibitor.

Definitions

Listed below are definitions of various terms used in this disclosure. These definitions apply to the terms as they are used throughout this specification and claims, unless otherwise limited in specific instances, either individually or as part of a larger group.

As used in the specification and in the claims, the term "comprising" may include the embodiments "consisting of" and "consisting essentially of" The terms "comprise(s)," "include(s)," "having," "has," "may," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated compounds, which allows the presence of only the named compounds, along with any pharmaceutically acceptable carriers, and excludes other compounds.

The term "about" generally indicates a possible variation of no more than 10%, 5%, or 1% of a value. For example, "about 25 mg/kg" will generally indicate, in its broadest sense, a value of 22.5-27.5 mg/kg, i.e., 25±2.5 mg/kg.

The term "alkyl" refers to saturated, straight- or branched-chain hydrocarbon moieties containing, in certain embodiments, between one and six, or one and eight carbon atoms. Examples of $C_{1-6}$-alkyl moieties include, but are not limited to, methyl, ethyl, propyl, isopropyl, n-butyl, tert-butyl, neopentyl, n-hexyl moieties; and examples of $C_{1-8}$-alkyl moieties include, but are not limited to, methyl, ethyl, propyl, isopropyl, n-butyl, tert-butyl, neopentyl, n-hexyl, heptyl, and octyl moieties.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "aryl" refers to a mono- or poly-cyclic carbocyclic ring system having one or more aromatic rings, fused or non-fused, including, but not limited to, phenyl, naphthyl, tetrahydronaphthyl, indanyl, idenyl and the like.

The term "heteroaryl" refers to a mono- or poly-cyclic (e.g., bi-, or tri-cyclic or more) fused or non-fused, moieties or ring system having at least one aromatic ring, having from five to ten ring atoms of which one ring atom is selected from S, O, and N; zero, one or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "halo" refers to a halogen, such as fluorine, chlorine, bromine, and iodine.

The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

The term "HDAC6 selective" means that the compound binds to HDAC6 to a substantially greater extent, such as 5×, 10×, 15×, 20× greater or more, than to any other type of HDAC enzyme, such as HDAC1 or HDAC2. That is, the compound is selective for HDAC6 over any other type of HDAC enzyme. For example, a compound that binds to HDAC6 with an $IC_{50}$ of 10 nM and to HDAC1 with an $IC_{50}$ of 50 nM is HDAC6 selective. On the other hand, a compound that binds to HDAC6 with an $IC_{50}$ of 50 nM and to HDAC1 with an $IC_{50}$ of 60 nM is not HDAC6 selective.

The term "inhibitor" is synonymous with the term antagonist.

A "BET inhibitor" targets bromodomain and extra-terminal motif (BET) proteins, including BRD2, BRD3, BRD4, and BRDT. BET proteins contain a bromodomain that recognizes acetylated lysine residues. BET inhibitors bind the bromodomains of BET proteins and alter cellular epigenetic and transcriptional programs. For example, a BET inhibitor includes, but is not limited to, ABBV-075, BAY1238097, BMS986158, bromosporine, CBP30, CPI-203, CPI-0610, FT-1101, GSK2820151, I-BET151, I-BET726, I-BET-762 (GSK525762), INCB054329, INCB057643, ISOX DUAL, JQ1, LY294002, LY303511, MS436, MK8628 (OTX-015), OF-1, OXF BD 02, PFI-1, PFI-3, PF-6405761, RVX-208, TEN-010, XD 14, and ZEN003694.

As used herein, the term "treatment" or "treating" indicates that the method has, at the least, mitigated the cancer. A method for treating comprises applying or administering to the subject a pharmaceutical combination comprising a HDAC6 selective inhibitor and a BET inhibitor. A method for treating comprises applying or administering to an isolated tissue or cell line from a subject (e.g., for diagnosis or ex vivo applications), who has cancer a pharmaceutical combination comprising a HDAC6 selective inhibitor and a BET inhibitor. The purpose of application or administration of the pharmaceutical combination is to cure, heal, alleviate, relieve, alter, remedy, ameliorate, improve, or affect cancer. Such treatments may be specifically tailored or modified, based on knowledge obtained from the field of pharmacogenomics. The methods of the disclosure can, at the least, mitigate abnormal cellular proliferation. For example, the method can reduce the rate of cancer growth in a patient, or prevent the continued growth or spread of the cancer, or even reduce the overall reach of the cancer.

As used herein, the term "patient," "individual," or "subject" refers to a human or a non-human mammal. Non-human mammals include, for example, livestock and pets, such as ovine, bovine, porcine, canine, feline, and murine mammals. Preferably, the patient, subject or individual is human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure may be synthesized from the parent compound which contains a basic or acidic moiety by conventional chemical methods. Generally, such salts may be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. The term "combination," "therapeutic combination," "pharmaceutical combination," or "combination product" as used herein refer to either a fixed combination in one dosage unit form, or non-fixed combination, or a kit of parts for the combined administration where two or more therapeutic agents may be administered independently, at the same time or separately within time intervals, especially where these time intervals allow that the combination partners show a cooperative, e.g., synergistic, effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single formulation having a fixed ratio of active ingredients or in separate formulations (e.g., capsules and/or intravenous formulations) for each active ingredient. In addition, such administration also encompasses use of each type of therapeutic agent in a sequential or separate manner, either at approximately the same time or at different times. Such administration also encompasses each component being formulated as a separate formulation that can be administered at different times. For example, the HDAC6 selective inhibitor of Formula I can be dosed daily. In any case, the treatment regimen will provide beneficial effects of the drug combination in treating the conditions or disorders described herein.

The term "sub-therapeutically effective amount" or "sub-therapeutic dose" is an amount or dose of the active ingredient (e.g., an HDAC6 selective inhibitor or a BET inhibitor), that, when administered to a patient by itself, does not completely inhibit over time the biological activity of the intended target.

The term "synergistic effect" refers to the action of two agents, such as, for example, an HDAC6 selective inhibitor and a BET inhibitor, producing an effect, for example, slowing the symptomatic progression of cancer, or symptoms thereof, which is greater than the simple addition of the effects of each drug administered alone.

As used herein, the term "resistant" or "refractive" to a therapeutic agent when referring to a cancer patient means that the cancer has innate, or achieved, resistance to the effects of the therapeutic agent as a result of contact with the therapeutic agent. Stated alternatively, the cancer patient is resistant to the ordinary standard of care associated with the particular therapeutic agent.

As used herein, "treatment naïve" refers to the patient not having previously received treatment with a drug, either investigational or approved, for cancer in particular, a BET inhibitor.

Alternatively, patients treated according to the methods of the disclosure may be "treatment experienced." As used herein, "treatment experienced" refers to a patient who has had at least one previous course of a cancer therapy, in particular a BET inhibitor. In some embodiments, the last dose in this previous course occurred at least three months prior to implementing a method according to the present disclosure.

Histone Deacetylase (HDAC) Inhibitors

Provided herein are methods for treating cancer in a subject in need thereof, comprising administering a HDAC inhibitor and a BET inhibitor. Also provided herein are pharmaceutical combinations comprising a HDAC inhibitor and a BET inhibitor.

The pharmaceutical combinations and methods disclosed herein comprise a histone deacetylase (HDAC) inhibitor. The HDAC inhibitor may be any HDAC inhibitor. Thus, the HDAC inhibitor may be selective or non-selective to a particular type of histone deacetylase enzyme. Preferably, the HDAC inhibitor is a selective HDAC inhibitor. More preferably, the HDAC inhibitor is an HDAC6 selective inhibitor.

In some embodiments, the HDAC6 selective inhibitor is a compound of Formula I:

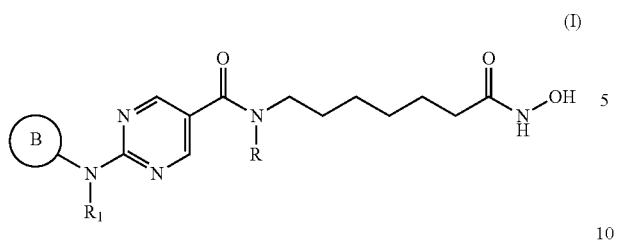

or a pharmaceutically acceptable salt thereof,
wherein,
ring B is aryl or heteroaryl;
$R_1$ is an aryl or heteroaryl, each of which may be optionally substituted by OH, halo, or $C_{1-6}$-alkyl;
and
R is H or $C_{1-6}$-alkyl.

Representative compounds of Formula I include, but are not limited to:

Compound A

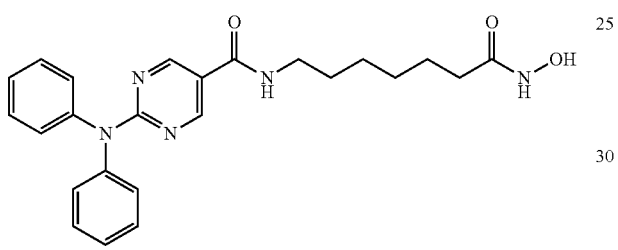

2-(diphenyl)-N-(7-(hydroxyamino)-7-oxoheptyl)pyrimidine-5-carboxamide
$IC_{50}$(nM) HDAC6 = 10 HDAC3 = 84

Compound B

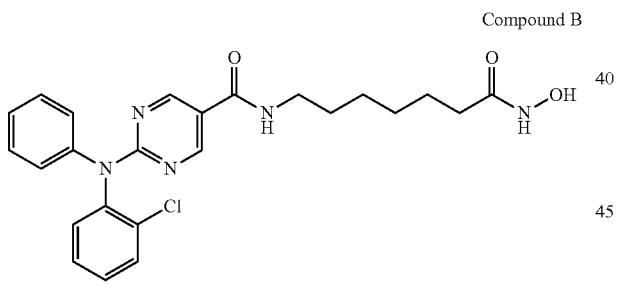

2-((2-chlorophenyl)(phenyl)amino)-N-(7-(hydroxyamino)-7-oxoheptyl)pyrimidine-5-carboxamide
$IC_{50}$(nM) HDAC6 = 4 HDAC3 = 76 or pharmaceutically acceptable salts thereof. In some embodiments, the HDAC6 selective inhibitor is Compound A, or a pharmaceutically acceptable salt thereof. Compound A is also referred to as ricolinostat. In other embodiments, the HDAC6 selective inhibitor is Compound B, or a pharmaceutically acceptable salt thereof.

The preparation and properties of selective HDAC6 inhibitors according to Formula I are provided in International Patent Application Nos. PCT/US2011/021982 and PCT/US2014/059238, the entire contents of which are incorporated herein by reference.

In other embodiments, the HDAC6 selective inhibitor is a compound of Formula II:

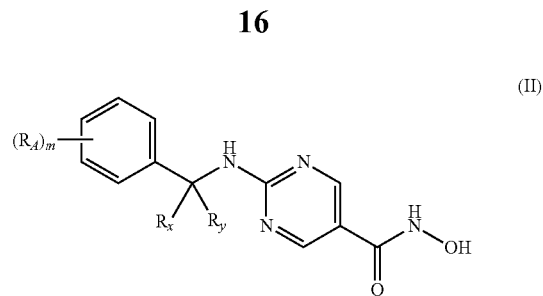

or a pharmaceutically acceptable salt thereof,
wherein,
$R_x$ and $R_y$ together with the carbon to which each is attached, form a cyclopropyl, cyclobutyl, cyclopentyl, cyclohexyl, cycloheptyl, or cyclooctyl;
each $R_A$ is independently $C_{1-6}$-alkyl, $C_{1-6}$-alkoxy, halo, OH, —$NO_2$, —CN, or —$NH_2$; and m is 0, 1, or 2.

Representative compounds of Formula I include, but are not limited to:

Compound C

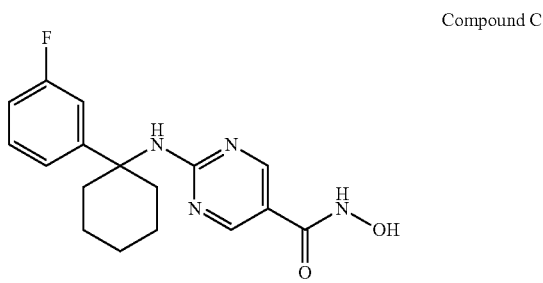

$IC_{50}$(nM) HDAC6 = 7 HDAC1 = 2123
(283.5x) HDAC2 = 2570 (9343.2x)
HDAC3 = 11223 (1498.8x)

Compound D

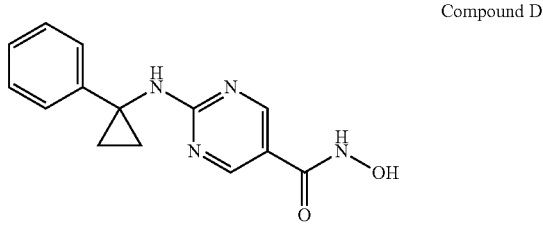

$IC_{50}$(nM) HDAC6 = 2 HDAC1 = 94 (60x)
HDAC2 = 128 (81.9x) HDAC3 = 219 (139.5x)

or pharmaceutically acceptable salts thereof. In some embodiments, the HDAC6 selective inhibitor is Compound C, or a pharmaceutically acceptable salt thereof. In other embodiments, the HDAC6 selective inhibitor is Compound D, or a pharmaceutically acceptable salt thereof.

The preparation and properties of selective HDAC6 inhibitors according to Formula II are provided in International Patent Application No. PCT/US2011/060791, the entire contents of which are incorporated herein by reference.

In another embodiment, the HDAC6 selective inhibitor is Tubastatin A, or a pharmaceutically acceptable salt thereof.

Bromodomain and Extra-Rerminal Motif Protein (BET) Inhibitor

Some embodiments of the pharmaceutical combinations and methods disclosed herein comprise a BET inhibitor. The BET inhibitor may be any BET inhibitor. In certain embodiments, the BET inhibitor is selected from the group consisting of ABBV-075, BAY1238097, BMS986158, bromosporine, CBP30, CPI-203, CPI-0610, FT-1101, GSK2820151, I-BET151, I-BET726, I-BET-762 (GSK525762), INCB054329, INCB057643, ISOX DUAL, JQ1, LY294002, LY303511, MS436, MK8628 (OTX-015), OF-1, OXF BD 02, PFI-1, PFI-3, PF-6405761, RVX-208, TEN-010, XD 14, and ZEN003694, or a pharmaceutically acceptable salt thereof.

In another embodiment, the BET inhibitor is JQ1 or (+)-JQ1, or a pharmaceutically acceptable salt thereof. In another embodiment, the BET inhibitor is JQ1:

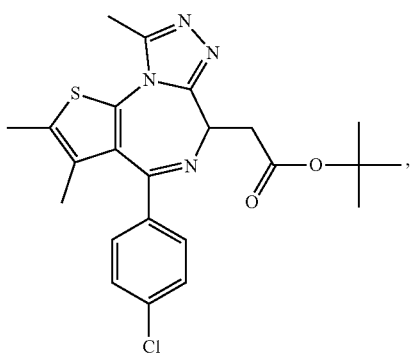

(JQ1)

or a pharmaceutically acceptable salt thereof. In yet another embodiment, the BET inhibitor is (+)-JQ1. In still another embodiment, the BET inhibitor (+)-JQ1 is referred to as JQ1. JQ1 is a well-known BET inhibitor (Filippakopoulos, P. et al., *Selective Inhibition of BET Bromodomains*. Nature, 2010. 468: p. 1067-73; Belkina, A. C. et al., *BET domain co-regulators in obesity, inflammation and cancer*. Nature Reviews Cancer, 2012. 12(7): p. 465-77, both of which are incorporated herein by reference in their entireties).

In some embodiments, the compounds described herein are unsolvated. In other embodiments, one or more of the compounds are in solvated form. As known in the art, the solvate can be any of pharmaceutically acceptable solvent, such as water, ethanol, and the like.

Although the compounds of Formulas I and II are depicted in their neutral forms, in some embodiments, these compounds are used in a pharmaceutically acceptable salt form.

Pharmaceutical Combinations and Compositions

Accordingly, in another aspect, provided herein is a pharmaceutical combination comprising a histone deacetylase (HDAC) inhibitor and a BET inhibitor.

In some embodiments of the pharmaceutical combinations, the HDAC inhibitor is an HDAC6 selective inhibitor. In specific embodiments, the HDAC6 selective inhibitor is a compound of Formula I:

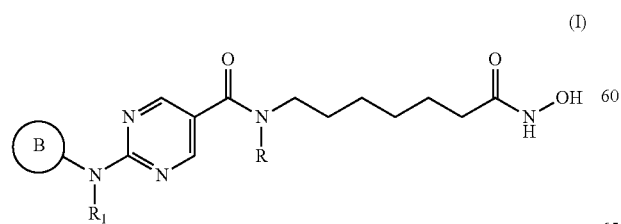

(I)

or a pharmaceutically acceptable salt thereof, wherein, ring B is aryl or heteroaryl;

$R_1$ is an aryl or heteroaryl, each of which may be optionally substituted by OH, halo, or $C_{1-6}$-alkyl;

and

R is H or $C_{1-6}$-alkyl.

In some embodiments, the compound of Formula I is Compound A

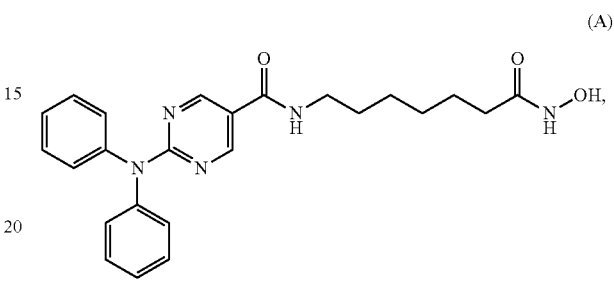

(A)

or a pharmaceutically acceptable salt thereof.

In yet other embodiments, the compound of Formula I is Compound B

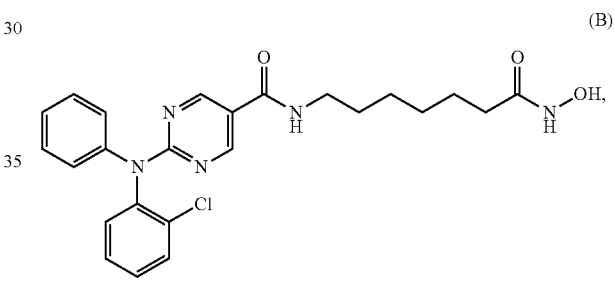

(B)

or a pharmaceutically acceptable salt thereof.

In yet another embodiment, the pharmaceutical combination comprises the HDAC6 selective inhibitor Compound A, or a pharmaceutically acceptable salt thereof, and the BET inhibitor JQ1, or a pharmaceutically acceptable salt thereof.

In still another embodiment, the pharmaceutical combination comprises the HDAC6 selective inhibitor Compound B, or a pharmaceutically acceptable salt thereof, and the BET inhibitor JQ1, or a pharmaceutically acceptable salt thereof.

In other embodiments, the HDAC6 selective inhibitor is a compound of Formula II:

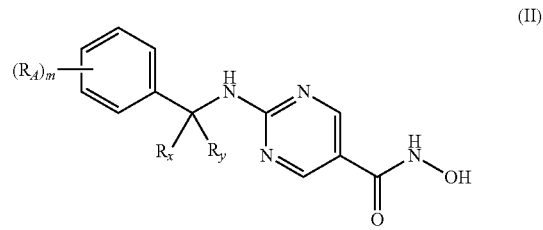

(II)

or a pharmaceutically acceptable salt thereof, wherein, $R_x$ and $R_y$ together with the carbon to which each is attached, form a cyclopropyl, cyclobutyl, cyclopentyl, cyclohexyl, cycloheptyl, or cyclooctyl;

each $R_4$ is independently $C_{1-6}$-alkyl, $C_{1-6}$-alkoxy, halo, OH, —$NO_2$, —CN, or —$NH_2$; and m is 0, 1, or 2.

In another embodiment, the pharmaceutical combination comprises the HDAC6 selective inhibitor Compound C, or a pharmaceutically acceptable salt thereof, and the BET inhibitor JQ1, or a pharmaceutically acceptable salt thereof.

In yet another embodiment, the pharmaceutical combination comprises the HDAC6 selective inhibitor Compound D, or a pharmaceutically acceptable salt thereof, and the BET inhibitor JQ1, or a pharmaceutically acceptable salt thereof.

In an embodiment, the pharmaceutical combination is for use in the treatment of cancer in a subject. In certain embodiments, the cancer is a resistant or refractory cancer.

In an embodiment, the pharmaceutical combination is for use in the treatment of cancer in a subject, wherein the subject is treatment naïve.

In other embodiments of the foregoing pharmaceutical combinations and compositions, the pharmaceutical combination or composition further comprises one or more pharmaceutically acceptable carriers.

Methods for Treating Cancer

In one aspect, the disclosure provides methods for treating cancer in a subject in need thereof, comprising administering to the subject a therapeutically effective amount of a pharmaceutical combination comprising an HDAC inhibitor and a BET inhibitor.

The subject considered herein is typically a human. However, the subject can be any mammal for which treatment is desired. Thus, the methods described herein can be applied to both human and veterinary applications.

As such, in one embodiment, provided herein is a method for treating cancer in a subject in need thereof, comprising administering to the subject a therapeutically effective amount of an HDAC6 selective inhibitor and a therapeutically effective amount of a BET inhibitor. In some embodiments, the HDAC6 selective inhibitor or the BET inhibitor are administered at a sub-therapeutic dose.

In another embodiment, provided herein is a method for treating cancer in a subject in need thereof, comprising administering to the subject a therapeutically effective amount of an HDAC6 selective inhibitor of Formula I and a therapeutically effective amount of a BET inhibitor.

In yet another embodiment, provided herein is a method for treating cancer in a subject in need thereof, comprising administering to the subject a therapeutically effective amount of an HDAC6 selective inhibitor of Formula II and a therapeutically effective amount of a BET inhibitor.

In yet another embodiment, provided herein is a method for treating cancer in a subject in need thereof, comprising administering to the subject a therapeutically effective amount of Compound A, or a pharmaceutically acceptable salt thereof, and a therapeutically effective amount of JQ1, or a pharmaceutically acceptable salt thereof.

In still another embodiment, provided herein is a method for treating cancer in a subject in need thereof, comprising administering to the subject a therapeutically effective amount of Compound B, or a pharmaceutically acceptable salt thereof, and a therapeutically effective amount of JQ1, or a pharmaceutically acceptable salt thereof.

In yet another embodiment, provided herein is a method for treating cancer in a subject in need thereof, comprising administering to the subject a therapeutically effective amount of Compound C, or a pharmaceutically acceptable salt thereof, and a therapeutically effective amount of JQ1, or a pharmaceutically acceptable salt thereof.

In yet another embodiment, provided herein is a method for treating cancer in a subject in need thereof, comprising administering to the subject a therapeutically effective amount of Compound D, or a pharmaceutically acceptable salt thereof, and a therapeutically effective amount of JQ1, or a pharmaceutically acceptable salt thereof.

In some embodiments of the methods disclosed herein, the cell is a cancer cell. In another embodiment, the cell is a lung cancer cell. In still another embodiment, the cell is a non-small cell lung cancer cell.

In yet another embodiment, provided herein is a method for treating lung cancer in a subject in need thereof, comprising administering to the subject a therapeutically effective amount of Compound A, or a pharmaceutically acceptable salt thereof, and a therapeutically effective amount of JQ1, or a pharmaceutically acceptable salt thereof.

In still another embodiment, provided herein is a method for treating lung cancer in a subject in need thereof, comprising administering to the subject a therapeutically effective amount of Compound B, or a pharmaceutically acceptable salt thereof, and a therapeutically effective amount of JQ1, or a pharmaceutically acceptable salt thereof.

In yet another embodiment, provided herein is a method for treating lung cancer in a subject in need thereof, comprising administering to the subject a therapeutically effective amount of Compound C, or a pharmaceutically acceptable salt thereof, and a therapeutically effective amount of JQ1, or a pharmaceutically acceptable salt thereof.

In yet another embodiment, provided herein is a method for treating lung cancer in a subject in need thereof, comprising administering to the subject a therapeutically effective amount of Compound D, or a pharmaceutically acceptable salt thereof, and a therapeutically effective amount of JQ1, or a pharmaceutically acceptable salt thereof.

In yet another embodiment, provided herein is a method for treating non-small cell lung cancer in a subject in need thereof, comprising administering to the subject a therapeutically effective amount of Compound A, or a pharmaceutically acceptable salt thereof, and a therapeutically effective amount of JQ1, or a pharmaceutically acceptable salt thereof.

In still another embodiment, provided herein is a method for treating non-small cell lung cancer in a subject in need thereof, comprising administering to the subject a therapeutically effective amount of Compound B, or a pharmaceutically acceptable salt thereof, and a therapeutically effective amount of JQ1, or a pharmaceutically acceptable salt thereof.

In yet another embodiment, provided herein is a method for treating non-small cell lung cancer in a subject in need thereof, comprising administering to the subject a therapeutically effective amount of Compound C, or a pharmaceutically acceptable salt thereof, and a therapeutically effective amount of JQ1, or a pharmaceutically acceptable salt thereof.

In yet another embodiment, provided herein is a method for treating non-small cell lung cancer in a subject in need thereof, comprising administering to the subject a therapeutically effective amount of Compound D, or a pharmaceutically acceptable salt thereof, and a therapeutically effective amount of JQ1, or a pharmaceutically acceptable salt thereof.

In some embodiments of the foregoing methods, the HDAC6 selective inhibitor induces apoptosis of cancer cells.

In other embodiments, provided are methods for decreasing cell viability of cancer cells in a subject with cancer by administering a pharmaceutical combination disclosed herein.

In another embodiment, provided are methods for synergistically increasing apoptosis of cancer cells in a subject with cancer by administering to a subject a pharmaceutical combination disclosed herein.

In still another embodiment, provided are methods for reducing circulating regulatory T lymphocytes (Tregs) in a subject with cancer by administering to the subject a therapeutically effective amount of an HDAC6 selective inhibitor, a therapeutically effective amount of a BET inhibitor, or a therapeutically effective amount of a pharmaceutical combination disclosed herein. In some embodiments, the Tregs are CD4+FOXP3+Tregs.

In yet another embodiment, provided are methods for altering expression of antigen presenting complexes in a subject with cancer by administering to the subject a therapeutically effective amount of an HDAC6 selective inhibitor, or a therapeutically effective amount of a pharmaceutical combination disclosed herein.

In a further embodiment, provided are methods for treating cancer by increasing costimulatory function of antigen presenting cells in a subject by administering to the subject a therapeutically effective amount of an HDAC6 selective inhibitor, or a therapeutically effective amount of a pharmaceutical combination disclosed herein. In some embodiments, the presenting protein is CD86, and the expression is increased. In another embodiment, the presenting protein is MHC II, and the expression is increased.

In a further embodiment, provided are methods for treating cancer by activating T cells in a subject by administering to the subject a therapeutically effective amount of an HDAC6 selective inhibitor, or a therapeutically effective amount of a pharmaceutical combination disclosed herein. In some embodiments, expression of CD69 is increased. In another embodiment, the T cells are CD69 positive CD4+ T cells. In another embodiment, the T cells are CD69 positive CD8+ T cells.

In another aspect, provided herein is a method for decreasing cell proliferation of cancer cells in a subject with cancer by administering to the subject a therapeutically effective amount of a pharmaceutical combination disclosed herein.

In yet another aspect, the disclosure relates to methods for upregulating lymphocyte functional activity in a subject in need thereof. Specifically, the disclosure relates to methods for upregulating lymphocyte functional activity in a subject in need thereof, comprising administering to the subject a therapeutically effective amount of an HDAC6 selective inhibitor, or a therapeutically effective amount of a pharmaceutical combination disclosed herein. In some embodiments, the lymphocyte is a T cell. In another embodiment, the functional activity is transient TCR-independent activation.

In certain embodiments of the foregoing methods, the cancer is lung cancer. In another embodiment of the foregoing methods, the lung cancer is non-small cell lung cancer, small cell lung cancer, or lung carcinoid tumor. In a further embodiment of the foregoing methods, the cancer is non-small cell lung cancer.

In some embodiments of the foregoing methods, the cancer is resistant or refractory cancer.

In certain embodiments of the foregoing methods, the HDAC6 selective inhibitor is selected from the group consisting of Compound A, Compound B, Compound C, Compound D, Tubastatin A, or a pharmaceutically acceptable salt thereof. In some embodiments, the BET inhibitor is JQ1, or a pharmaceutically acceptable salt thereof.

Administration/Dose

In some embodiments, the HDAC6 selective inhibitor (a compound of Formula I or Formula II) is administered simultaneously with the BET inhibitor. Simultaneous administration typically means that both compounds enter the patient at precisely the same time. However, simultaneous administration also includes the possibility that the HDAC6 selective inhibitor and the BET inhibitor enter the patient at different times, but the difference in time is sufficiently miniscule that the first administered compound is not provided the time to take effect on the patient before entry of the second administered compound. Such delayed times typically correspond to less than 1 minute, and more typically, less than 30 seconds. In one example, wherein the compounds are in solution, simultaneous administration can be achieved by administering a solution containing the pharmaceutical combination of compounds. In another example, simultaneous administration of separate solutions, one of which contains the HDAC6 selective inhibitor and the other of which contains the BET inhibitor, can be employed. In one example wherein the compounds are in solid form, simultaneous administration can be achieved by administering a composition containing the pharmaceutical combination of compounds. Alternatively, simultaneous administration can be achieved by administering two separate compositions, one comprising the HDAC6 selective inhibitor and the other comprising the BET inhibitor. In another embodiment, the HDAC6 selective inhibitor and the BET inhibitor are administered at substantially the same time.

In some embodiments, the pharmaceutical combination of compounds exhibits a synergistic effect (i.e., greater than additive effect) in the treatment of the cancer. The term "synergistic effect" refers to the action of two agents, such as, for example, an HDAC6 selective inhibitor and a BET inhibitor, producing an effect, for example, slowing the symptomatic progression of cancer or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve, and combination index curve, respectively.

In other embodiments, the HDAC6 selective inhibitor and the BET inhibitor are not administered simultaneously, but the two agents exhibit a synergistic effect. In some embodiments, the HDAC6 selective inhibitor is administered before the BET inhibitor. In other embodiments, the BET inhibitor is administered before the HDAC6 selective inhibitor. The time difference in non-simultaneous administrations can be greater than 1 minute, 5 minutes, 10 minutes, 15 minutes, 30 minutes, 45 minutes, 60 minutes, two hours, three hours, six hours, nine hours, 12 hours, 24 hours, 36 hours, 48 hours, 3 days, 4 days, 5 days, 6 days, or 7 days. In other embodiments, the first administered compound is provided time to take effect on the patient before the second administered compound is administered. Generally, the difference in time does not extend beyond the time for the first administered compound to complete its effect in the patient, or beyond the time the first administered compound is completely or substantially eliminated or deactivated in the patient. In another embodiment, the HDAC6 selective inhibitor and the BET inhibitor are administered at different times.

In some embodiments, the HDAC6 selective inhibitor and the BET inhibitor are together formulated as a single formulation.

In other embodiments, the HDAC inhibitor and the BET inhibitor are each formulated as separate formulations.

In some embodiments, one or both of the HDAC6 selective inhibitor and the BET inhibitor are administered in a therapeutically effective amount or dosage. A "therapeutically effective amount" is an amount of an HDAC6 selective inhibitor (a compound of Formula I or II) or of a BET inhibitor that, when administered to a patient by itself, effectively treats cancer. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners. The amount of the compound that corresponds to a therapeutically effective amount is strongly dependent on the type of cancer, stage of the cancer, the age of the patient being treated, and other facts. In general, therapeutically effective amounts of these compounds are well-known in the art, such as provided in the supporting references cited above.

In other embodiments, one or both of the HDAC6 selective inhibitor and the BET inhibitor are administered in a sub-therapeutically effective amount or dosage. A sub-therapeutically effective amount is an amount of HDAC6 selective inhibitor (a compound of Formula I or II) or a BET inhibitor that, when administered to a patient by itself, does not completely inhibit over time the biological activity of the intended target.

Whether administered in therapeutic or sub-therapeutic amounts, the pharmaceutical combination of the HDAC6 selective inhibitor and the BET inhibitor should be effective in treating cancer. For example, a sub-therapeutic amount of a compound of the BET inhibitor can be an effective amount if, when combined with a compound of Formula I or II (HDAC6 selective inhibitor), the pharmaceutical combination is effective in the treatment of cancer.

In certain embodiments of the disclosure, the pharmaceutical combinations and methods include an HDAC6 selective inhibitor of Formula I and a BET inhibitor. Thus, in one embodiment, the pharmaceutical combinations and methods include Compound A and a BET inhibitor. In another embodiment, the pharmaceutical combinations and methods include Compound B and a BET inhibitor. In another embodiment, the pharmaceutical combinations and methods include Compound C and a BET inhibitor. In yet another embodiment, the pharmaceutical combinations and methods include Compound D and a BET inhibitor. These embodiments exhibit synergy such that sub-therapeutic amounts of the HDAC6 selective inhibitor or of the BET inhibitor may be used. In certain embodiments of the disclosure, the pharmaceutical combinations and methods include an HDAC6 selective inhibitor of Formula II and a BET inhibitor.

In different embodiments, depending on the pharmaceutical combination and the effective amounts used, the pharmaceutical combination of compounds can inhibit cancer growth, achieve cancer stasis, or even achieve substantial or complete cancer regression.

While the amounts of an HDAC6 selective inhibitor and a BET inhibitor should result in the effective treatment of cancer, the amounts, when combined, are preferably not excessively toxic to the patient (i.e., the amounts are preferably within toxicity limits as established by medical guidelines). In some embodiments, either to prevent excessive toxicity and/or provide a more efficacious treatment of cancer, a limitation on the total administered dosage is provided. Typically, the amounts considered herein are per day; however, half-day and two-day or three-day cycles also are considered herein.

Different dosage regimens may be used to treat cancer. In some embodiments, a daily dosage, such as any of the exemplary dosages described above, is administered once, twice, three times, or four times a day for three, four, five, six, seven, eight, nine, or ten days. Depending on the stage and severity of the cancer, a shorter treatment time (e.g., up to five days) may be employed along with a high dosage, or a longer treatment time (e.g., ten or more days, or weeks, or a month, or longer) may be employed along with a low dosage. In some embodiments, a once- or twice-daily dosage is administered every other day. In some embodiments, each dosage contains both an HDAC6 selective inhibitor and a BET inhibitor to be delivered as a single dosage, while in other embodiments, each dosage contains either an HDAC6 selective inhibitor and a BET inhibitor to be delivered as separate dosages.

The HDAC6 selective inhibitors, the BET inhibitors, or their pharmaceutically acceptable salts or solvate forms, in pure form or in an appropriate pharmaceutical composition, can be administered via any of the accepted modes of administration or agents known in the art. The compounds can be administered, for example, orally, nasally, parenterally (intravenous, intramuscular, or subcutaneous), topically, transdermally, intravaginally, intravesically, intracisternally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, preferably in unit dosage forms suitable for simple administration of precise dosages. A particular route of administration is oral, particularly one in which a convenient daily dosage regimen can be adjusted according to the degree of severity of the disease to be treated.

As discussed above, the HDAC6 selective inhibitor and the BET inhibitor of the pharmaceutical combination can be administered in a single unit dose or separate dosage forms. Accordingly, the phrase "pharmaceutical combination" includes a combination of two drugs in either a single dosage form or separate dosage forms, i.e., the pharmaceutically acceptable carriers and excipients described throughout the application can be combined with an HDAC6 selective inhibitor and a BET inhibitor in a single unit dose, as well as individually combined with an HDAC6 selective inhibitor and a BET inhibitor when these compounds are administered separately.

Auxiliary and adjuvant agents may include, for example, preserving, wetting, suspending, sweetening, flavoring, perfuming, emulsifying, and dispensing agents. Prevention of the action of microorganisms is generally provided by various antibacterial and antifungal agents. Isotonic agents may also be included. Prolonged absorption of an injectable pharmaceutical form can be brought about by the use of agents delaying absorption. The auxiliary agents also can include wetting agents, emulsifying agents, pH buffering agents, and antioxidants.

Solid dosage forms can be prepared with coatings and shells, such as enteric coatings and others well-known in the art. They can contain pacifying agents and can be of such composition that they release the active compound or compounds in a certain part of the intestinal tract in a delayed manner. Examples of embedded compositions that can be used are polymeric substances and waxes. The active compounds also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the HDAC6 selective inhibitors or BET inhibitors described herein, or a pharmaceutically acceptable salt thereof, and optional pharmaceutical adjuvants in a carrier to thereby form a solution or suspension.

Generally, depending on the intended mode of administration, the pharmaceutically acceptable compositions will contain about 1% to about 99% by weight of the compounds described herein, or a pharmaceutically acceptable salt thereof, and 99% to 1% by weight of a pharmaceutically acceptable excipient. In one example, the composition will be between about 5% and about 75% by weight of a compound described herein, or a pharmaceutically acceptable salt thereof, with the rest being suitable pharmaceutical excipients.

Actual methods of preparing such dosage forms are known, or will be apparent, to those skilled in this art. Reference is made, for example, to Remington's Pharmaceutical Sciences, 18th Ed. (Mack Publishing Company, Easton, Pa., 1990).

Kits

In other embodiments, kits are provided. Kits according to the disclosure include package(s) comprising compounds or compositions of the disclosure. In some embodiments, kits comprise an HDAC6 selective inhibitor, or a pharmaceutically acceptable salt thereof, and a BET inhibitor, or a pharmaceutically acceptable salt thereof.

The phrase "package" means any vessel containing compounds or compositions presented herein. In some embodiments, the package can be a box or wrapping. Packaging materials for use in packaging pharmaceutical products are well-known to those of skill in the art. Examples of pharmaceutical packaging materials include, but are not limited to, bottles, tubes, inhalers, pumps, bags, vials, containers, syringes, bottles, and any packaging material suitable for a selected formulation and intended mode of administration and treatment.

The kit can also contain items that are not contained within the package, but are attached to the outside of the package, for example, pipettes.

Kits can further contain instructions for administering compounds or compositions of the disclosure to a patient. Kits also can comprise instructions for approved uses of compounds herein by regulatory agencies, such as the United States Food and Drug Administration. Kits can also contain labeling or product inserts for the compounds. The package(s) and/or any product insert(s) may themselves be approved by regulatory agencies. The kits can include compounds in the solid phase or in a liquid phase (such as buffers provided) in a package. The kits can also include buffers for preparing solutions for conducting the methods, and pipettes for transferring liquids from one container to another.

EXAMPLES

Examples have been set forth below for the purpose of illustration and to describe certain specific embodiments. However, the scope of the claims is not to be in any way limited by the examples set forth herein. Various changes and modifications to the disclosed embodiments will be apparent to those skilled in the art and such changes and modifications including, without limitation, those relating to the chemical structures, substituents, derivatives, formulations and/or methods of the disclosure may be made without departing from the spirit of the disclosure and the scope of the appended claims. Definitions of the variables in the structures in the schemes herein are commensurate with those of corresponding positions in the formulae presented herein.

The synthesis of the compounds of Formula I is provided in International Patent Application Nos. PCT/US2011/021982 (Compound B) and PCT/US2014/059238 (Compounds A and B), which are incorporated herein by reference in their entireties. The synthesis of compounds of Formula II (Compounds C and D) is provided in PCT/US2011/060791, which is incorporated herein by reference in its entirety.

Example 1: Synthesis of 2-(diphenylamino)-N-(7-(hydroxyamino)-7-oxoheptyl)pyrimidine-5-carboxamide (Compound A)

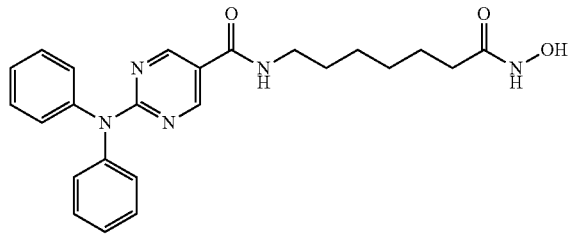 [SMILES: O=C(CCCCCCNC(=O)c1cnc(N(c2ccccc2)c2ccccc2)nc1)NO]

Reaction Scheme

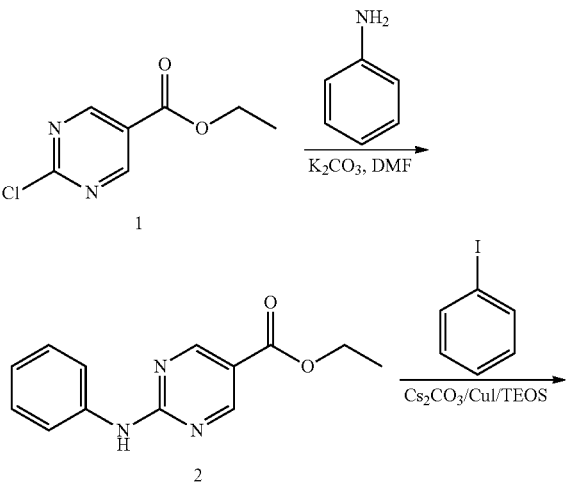

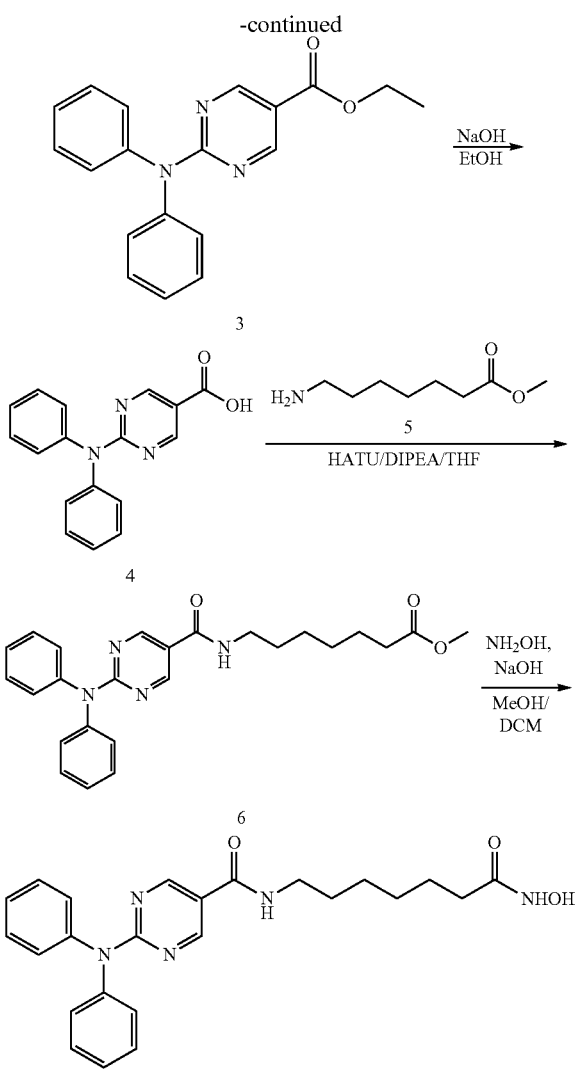

Synthesis of Intermediate 2

A mixture of aniline (3.7 g, 40 mmol), compound 1 (7.5 g, 40 mmol), and K$_2$CO$_3$ (11 g, 80 mmol) in DMF (100 ml) was degassed and stirred at 120° C. under N$_2$ overnight. The reaction mixture was cooled to r.t. and diluted with EtOAc (200 ml), then washed with saturated brine (200 ml×3). The organic layers were separated and dried over Na$_2$SO$_4$, evaporated to dryness and purified by silica gel chromatography (petroleum ether/EtOAc=10/1) to give the desired product as a white solid (6.2 g, 64%).

Synthesis of Intermediate 3

A mixture of compound 2 (6.2 g, 25 mmol), iodobenzene (6.12 g, 30 mmol), CuI (955 mg, 5.0 mmol), Cs$_2$CO$_3$ (16.3 g, 50 mmol) in TEOS (200 ml) was degassed and purged with nitrogen. The resulting mixture was stirred at 140° C. for 14 hrs. After cooling to r.t., the residue was diluted with EtOAc (200 ml). 95% EtOH (200 ml) and NH$_4$F—H$_2$O on silica gel [50 g, pre-prepared by the addition of NH$_4$F (100 g) in water (1500 ml) to silica gel (500 g, 100-200 mesh)] was added, and the resulting mixture was kept at r.t. for 2 hrs. The solidified materials were filtered and washed with EtOAc. The filtrate was evaporated to dryness and the residue was purified by silica gel chromatography (petroleum ether/EtOAc=10/1) to give a yellow solid (3 g, 38%).

Synthesis of Intermediate 4

2N NaOH (200 ml) was added to a solution of compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layers were separated, washed with water (2×100 ml), brine (2×100 ml), and dried over Na$_2$SO$_4$. Removal of the solvent gave a brown solid (2.5 g, 92%).

Synthesis of Intermediate 6

A mixture of compound 4 (2.5 g, 8.58 mmol), compound 5 (2.52 g, 12.87 mmol), HATU (3.91 g, 10.30 mmol), and DIPEA (4.43 g, 34.32 mmol) was stirred at r.t. overnight. After the reaction mixture was filtered, the filtrate was evaporated to dryness and the residue was purified by silica gel chromatography (petroleum ethers/EtOAc=2/1) to give a brown solid (2 g, 54%).

Synthesis of 2-(diphenylamino)-N-(7-(hydroxyamino)-7-oxoheptyl)pyrimidine-5-carboxamide (Compound A)

A mixture of the compound 6 (2.0 g, 4.6 mmol), sodium hydroxide (2N, 20 mL) in MeOH (50 ml) and DCM (25 ml) was stirred at 0° C. for 10 min. Hydroxylamine (50%) (10 ml) was cooled to 0° C. and added to the mixture. The resulting mixture was stirred at r.t. for 20 min. After removal of the solvent, the mixture was neutralized with 1M HCl to give a white precipitate. The crude product was filtered and purified by pre-HPLC to give a white solid (950 mg, 48%).

Example 2: Synthesis of 2-((2-chlorophenyl)(phenyl)amino)-N-(7-(hydroxyamino)-7-oxoheptyl)pyrimidine-5-carboxamide (Compound B)

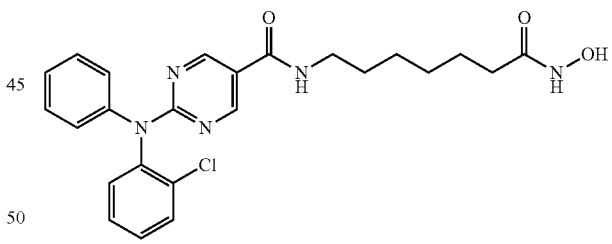

Reaction Scheme

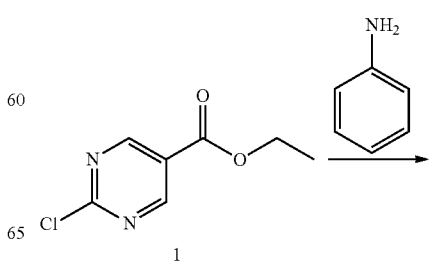

-continued

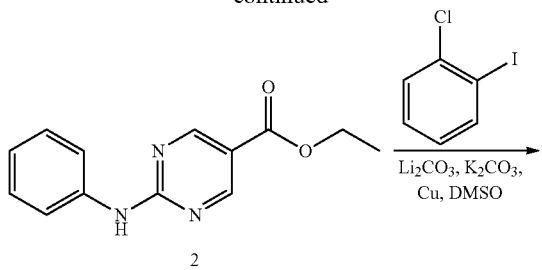

Synthesis of Intermediate 2

See synthesis of intermediate 2 in Example 1.

Synthesis of Intermediate 3

A mixture of compound 2 (69.2 g, 1 equiv.), 1-chloro-2-iodobenzene (135.7 g, 2 equiv.), Li$_2$CO$_3$ (42.04 g, 2 equiv.), K$_2$CO$_3$ (39.32 g, 1 equiv.), Cu (1 equiv. 45 μm) in DMSO (690 ml) was degassed and purged with nitrogen. The resulting mixture was stirred at 140° C. Work-up of the reaction gave compound 3 at 93% yield.

Synthesis of Intermediate 4

See synthesis of intermediate 4 in Example 1.

Synthesis of Intermediate 6

See synthesis of intermediate 6 in Example 1.

Synthesis of 2-((2-chlorophenyl)(phenyl)amino)-N-(7-(hydroxyamino)-7-oxoheptyl)pyrimidine-5-carboxamide (Compound B)

See synthesis of Compound A in Example 1.

Example 3: Synthesis of 2-((1-(3-fluorophenyl)cyclohexyl)amino)-N-hydroxypyrimidine-5-carboxamide (Compound C)

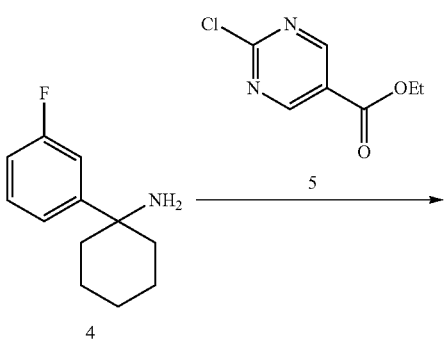

-continued

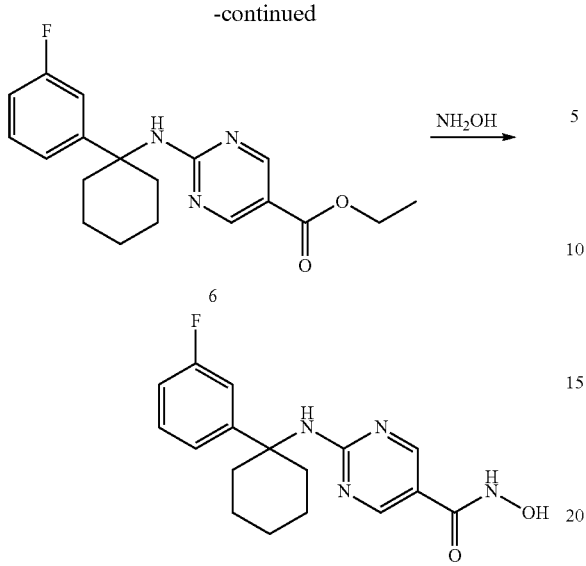

Synthesis of Intermediate 2

To a solution of compound 1 (100 g, 0.74 mol) in dry DMF (1000 ml) was added 1,5-dibromopentane (170 g, 0.74 mol). NaH (65 g, 2.2 eq) was added dropwise while the reaction was cooled in an ice bath. The resulting mixture was vigorously stirred overnight at 50° C. The suspension was carefully quenched with ice water and extracted with ethyl acetate (3×500 ml). The combined organic layers were concentrated to afford the crude product, which was purified by flash column chromatography to give compound 2 as pale solid (100 g, 67%).

Synthesis of Intermediate 3

A solution of compound 2 (100 g, 0.49 mol) in PPA (500 ml) was heated at 110° C. for about 5-6 hours. After completion, the resulting mixture was carefully adjusted to a pH of about 8-9 with saturated NaHCO$_3$ solution. The resulting precipitate was collected and washed with water (1000 ml) to afford compound 3 as white solid (95 g, 87%).

Synthesis of Intermediate 4

To a solution of compound 3 (95 g, 0.43 mol) in n-BuOH (800 ml) was added NaClO (260 ml, 1.4 eq). 3N NaOH (400 ml, 2.8 equiv.) was then added at 0° C. and the reaction was stirred overnight at r.t. The resulting mixture was extracted with EA (2×500 ml), and the combined organic layers washed with brine. The solvent was removed in vacuo to afford the crude product which was further purified by treatment with HCl salt to yield compound 4 as a white powder (72 g, 73%).

Synthesis of Intermediate 6

To a solution of compound 4 (2.29 g 10 mmol) in dioxane (50 ml) was added compound 5 (1.87 g, 1.0 equiv.) and DIPEA (2.58 g, 2.0 equiv.). The mixture was heated overnight at 110-120° C. The resulting mixture was directly purified on silica gel column to afford the coupled product, compound 6, as a white solid (1.37 g, 40%).

Synthesis of 2-((1-(3-fluorophenyl)cyclohexyl)amino)-N-hydroxypyrimidine-5-carboxamide (Compound C)

To a solution of compound 6 (100 mg, 0.29 mmol) in MeOH/DCM (10 ml, 1:1) was added 50% NH$_2$OH in water (2 ml, excess). Sat. NaOH in MeOH (2 ml, excess) was then added at 0° C. and the reaction was stirred for 3-4 hours. After completion, the resulting mixture was concentrated and acidified with 2N HCl to reach a pH of 4-5. The precipitate was collected and washed with water (10 ml) to remove excess NH$_2$OH. Drying the precipitate afforded 2-((1-(3-fluorophenyl)cyclohexyl)amino)-N-hydroxypyrimidine-5-carboxamide as a white powder (70 mg, 73%).

Example 4: Synthesis of N-hydroxy-2-((1-phenylcyclopropyl)amino)pyrimidine-5-carboxamide (Compound D)

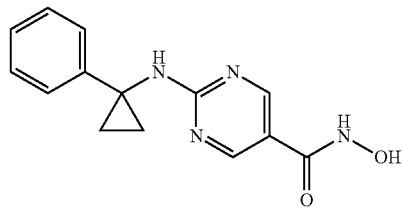 [SMILES: O=C(NO)c1cnc(NC2(c3ccccc3)CC2)nc1]

Reaction Scheme

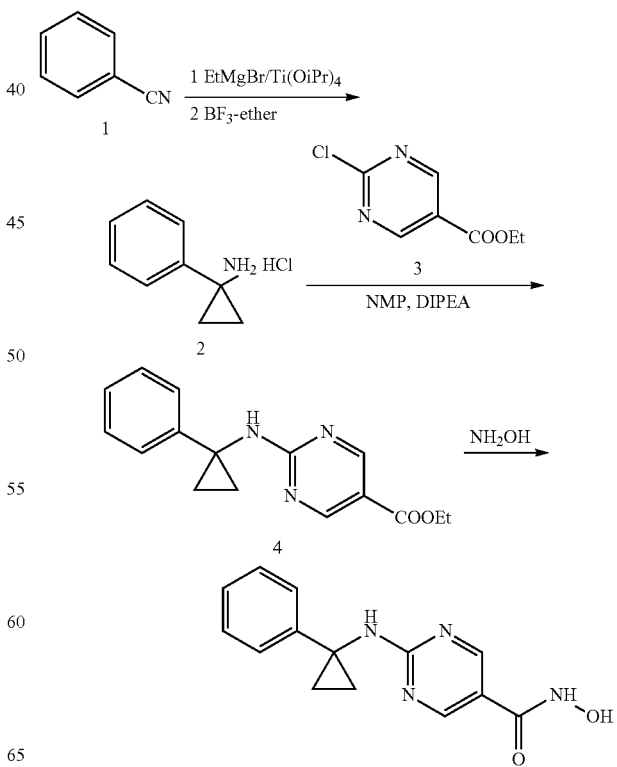

Synthesis of Intermediate 2

A solution of compound 1, benzonitrile, (250 g, 1.0 equiv.), and Ti(OiPr)$_4$ (1330 ml, 1.5 equiv.) in MTBE (3750 ml) was cooled to about −10 to −5° C. under a nitrogen atmosphere. EtMgBr (1610 ml, 3.0M, 2.3 equiv.) was added dropwise over a period of 60 min., during which the inner temperature of the reaction was kept below 5° C. The reaction mixture was allowed to warm to 15-20° C. for 1 hr. BF$_3$-ether (1300 ml, 2.0 equiv.) was added dropwise over a period of 60 min., while the inner temperature was maintained below 15° C. The reaction mixture was stirred at 15-20° C. for 1-2 hr. and stopped when a low level of benzonitrile remained. 1N HCl (2500 ml) was added dropwise while maintaining the inner temperature below 30° C. NaOH (20%, 3000 ml) was added dropwise to bring the pH to about 9.0, while still maintaining a temperature below 30° C. The reaction mixture was extracted with MTBE (3 L×2) and EtOAc (3 L×2), and the combined organic layers were dried with anhydrous Na$_2$SO$_4$ and concentrated under reduced pressure (below 45° C.) to yield a red oil. MTBE (2500 ml) was added to the oil to give a clear solution, and upon bubbling with dry HCl gas, a solid precipitated. This solid was filtered and dried in vacuum yielding 143 g of compound 2.

Synthesis of Intermediate 4

Compound 2 (620 g, 1.0 equiv) and DIPEA (1080 g, 2.2 equiv. were dissolved in NMP (3100 ml) and stirred for 20 min. Compound 3 (680 g, 1.02 equiv.) was added and the reaction mixture was heated to about 85-95° C. for 4 hrs. The solution was allowed to slowly cool to r.t. This solution was poured onto H$_2$O (20 L) and much of the solid was precipitated out from the solution with strong stirring. The mixture was filtered and the cake was dried under reduced pressure at 50° C. for 24 hr., yielding 896 g of compound 4 (solid, 86.8%).

Synthesis of N-hydroxy-2-((1-phenylcyclopropyl)amino)pyrimidine-5-carboxamide (Compound D)

A solution of MeOH (1000 ml) was cooled to about 0-5° C. with stirring. NH$_2$OH HCl (1107 g, 10 equiv.) was added, followed by careful addition of NaOCH$_3$ (1000 g, 12.0 equiv.) The resulting mixture was stirred at 0-5° C. for one hr, and was filtered to remove the solid. Compound 4 (450 g, 1.0 equiv.) was added to the reaction mixture in one portion, and stirred at 10° C. for two hours until compound 4 was consumed. The reaction mixture was adjusted to a pH of about 8.5-9 through addition of HCl (6N), resulting in precipitation. The mixture was concentrated under reduced pressure. Water (3000 ml) was added to the residue with intense stirring and the precipitate was collected by filtration. The product was dried in an oven at 45° C. overnight (340 g, 79% yield).

Example 5: HDAC Enzyme Assays

Compounds for testing were diluted in DMSO to 50 fold the final concentration and a 10.3 fold dilution series was made. The compounds were diluted in assay buffer (50 mM HOPES, pH 7.4, 100 mM Kill, 0.001% Tween-20, 0.05% BASE, 20 μM TEC) to 6 fold their final concentration. The HDAC enzymes (purchased from BPS Biosciences) were diluted to 1.5 fold their final concentration in assay buffer. The dipeptide substrate and trypsin at 0.05 μM final concentration were diluted in assay buffer at 6 fold their final concentration. The final enzyme concentrations used in these assays were 3.3 ng/ml (HDAC1), 0.2 ng/ml (HDAC2), 0.08 ng/ml (HDAC3) and 2 ng/ml (HDAC6). The final substrate concentrations used were 16 μM (HDAC1), 10 μM (HDAC2), 17 μM (HDAC3) and 14 μM (HDAC6). Five μl of compound and 20 μl of enzyme were added to wells of a black, opaque 384 well plate in duplicate. Enzyme and compound were incubated together at room temperature for 10 minutes. Five μl of substrate was added to each well, the plate was shaken for 60 seconds and placed into a Victor 2 μl plate reader. The development of fluorescence was monitored for 60 minutes and the linear rate of the reaction was calculated. The IC$_{50}$ was determined using Graph Pad Prism by a four parameter curve fit.

Example 6: HDAC Inhibitors in PBMC Cells and NSCLC Cells and Activation of T Lymphocytes The purpose of the following examples was to evaluate the preclinical activity of the HDAC6 inhibitor Compound A alone, and the potential of combining Compound A with JQ1 (a BET inhibitor) in non-small cell lung cancer cell lines. In these examples, (+)-JQ1 (referred to as JQ1 in the Examples) was utilized.

I. Effects of HDAC Inhibitors on Peripheral Blood Mononuclear Cells (PBMCs) from Healthy Donors HDAC inhibition results in tumor growth arrest in immunocompetent animal models. The effects of class I and class II HDAC inhibition on leukocytes were investigated using peripheral blood mononuclear cells (PBMCs) obtained from healthy donors. The PBMCs were cultured with Compound A and the results were compared with a panel of HDAC inhibitors with varying selectivity for HDAC6. This panel included HDAC6 selective inhibitors Compound B, Compound C, Compound D, and Tubastatin A; and an HDAC1/2/3 (Class I HDAC)-selective inhibitor entinostat (MS-275) (Table 1).

TABLE 1

HDAC inhibitors tested with healthy donor PBMCs and HDAC biochemical assay data.

| Compound | MW | HDAC Biochemical Assay Data IC$_{50}$ (nM) | |
|---|---|---|---|
| Compound A | 433.5 | HDAC6 = 10 | |
| | | HDAC3 = 84 | |
| Compound B | 468.0 | HDAC6 = 4 | |
| | | HDAC3 = 76 | |
| Compound C | 330.4 | HDAC6 = 7 | HDAC1 = 2123 |
| | | HDAC2 = 2570 | HDAC3 = 11223 |
| Compound D | 270.3 | HDAC6 = 2 | HDAC1 = 94 |
| | | HDAC2 = 128 | HDAC3 = 219 |
| Tubastatin | 371.9 | HDAC6 = 15 | HDAC1 = 16400 |
| | | HDAC2 = >30,000 | HDAC3 = >30,000 |
| Entinostat | 376.4 | Class I HDAC inhibitor | |
| | | HDAC1 = 510 | HDAC3 = 1700 |

Figure 1B:
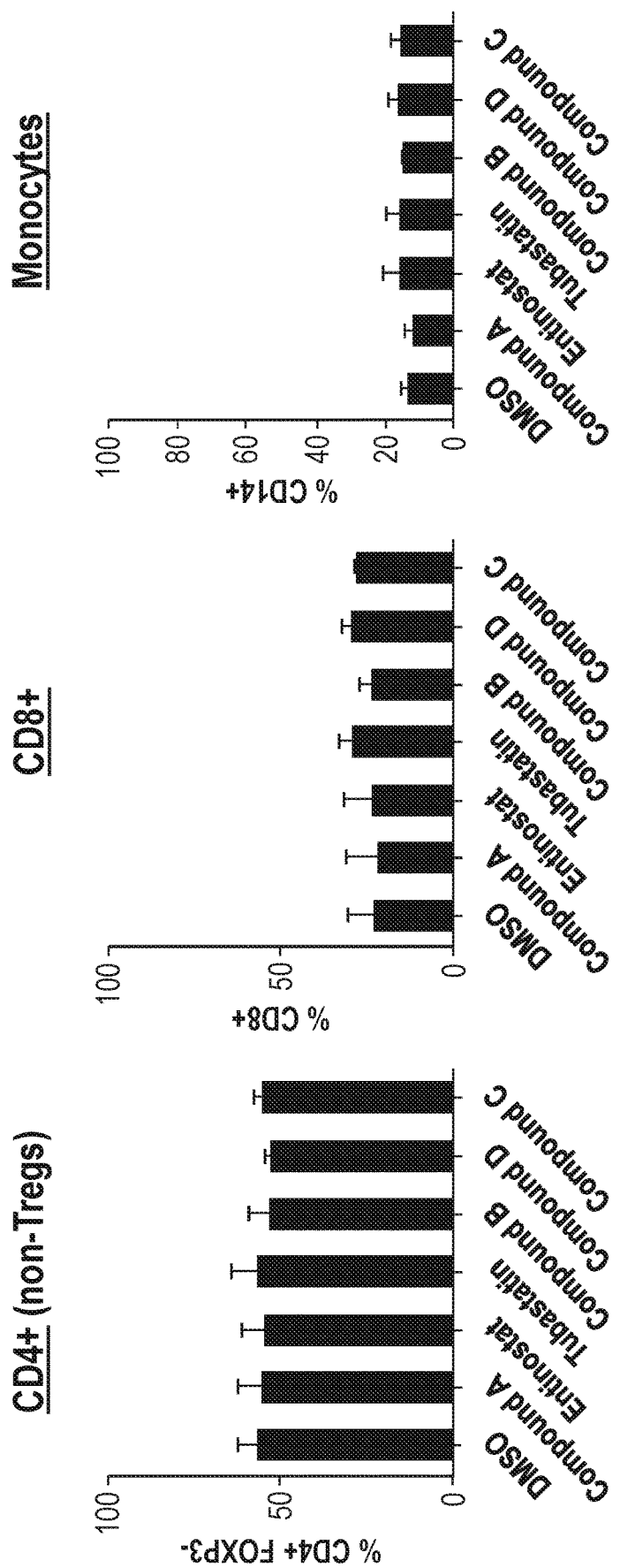
FIG. 1B shows the percentage of CD4+FOXP3− T cells (left), CD8+ T cells (middle), or CD3−CD14+ monocytes (right) in total viable PBMCs after culture with indicated HDAC inhibitors.
Figure 1C:
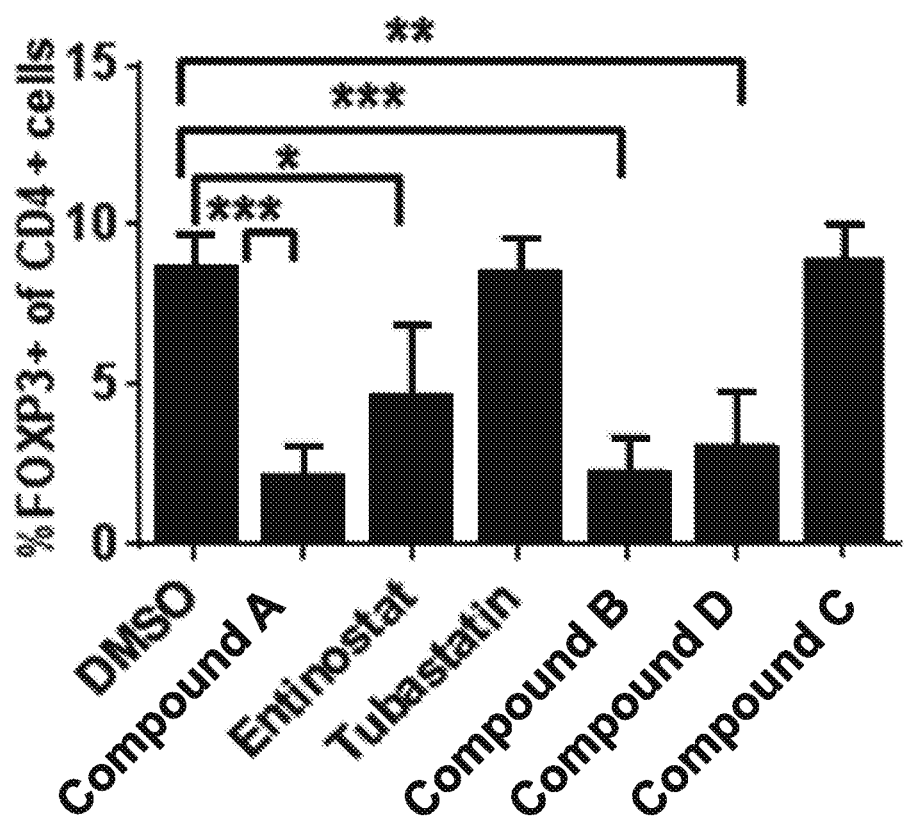
FIG. 1C shows a summary of proportions of CD4+ Foxp3+ Treg cells after 24-hour culture of healthy donor patient PBMCs with indicated drugs. Data represent the mean±SEM of samples analyzed from 4-8 subjects. * indicates p-value<0.05,  indicates p-value<0.001, * indicates p-value<0.0001.

The PBMCs were cultured with the HDAC inhibitors for 24 hours after which the frequency of T cell subsets was assessed by FACS. DMSO was used as a control. Notably, viability of cells cultured for 24 hours with these HDAC inhibitors was largely similar (FIG. 1A). With respect to cellular subtypes, the frequency of CD4+FOXP3− and CD8+ conventional T cells were not significantly impacted by these drugs (FIG. 1B). The percentage of CD4+FOXP3+ Tregs within PBMCs was reduced most significantly when cultured with Compound A or Compound B while the effect was still present with Compound D or entinostat. (FIG. 1C). Interestingly, the highly selective HDAC6 inhibitors Compound C and Tubastatin A did not significantly impact Treg frequency, suggesting that Class I HDAC inhibition by compounds such as Compound A, Compound B, and entinostat contributes to the observed reduction in Treg frequency.

II. Effects of Compound A or Entinostat on Non-Small Cell Lung Cancer Cells

Figures 2A, 2B:
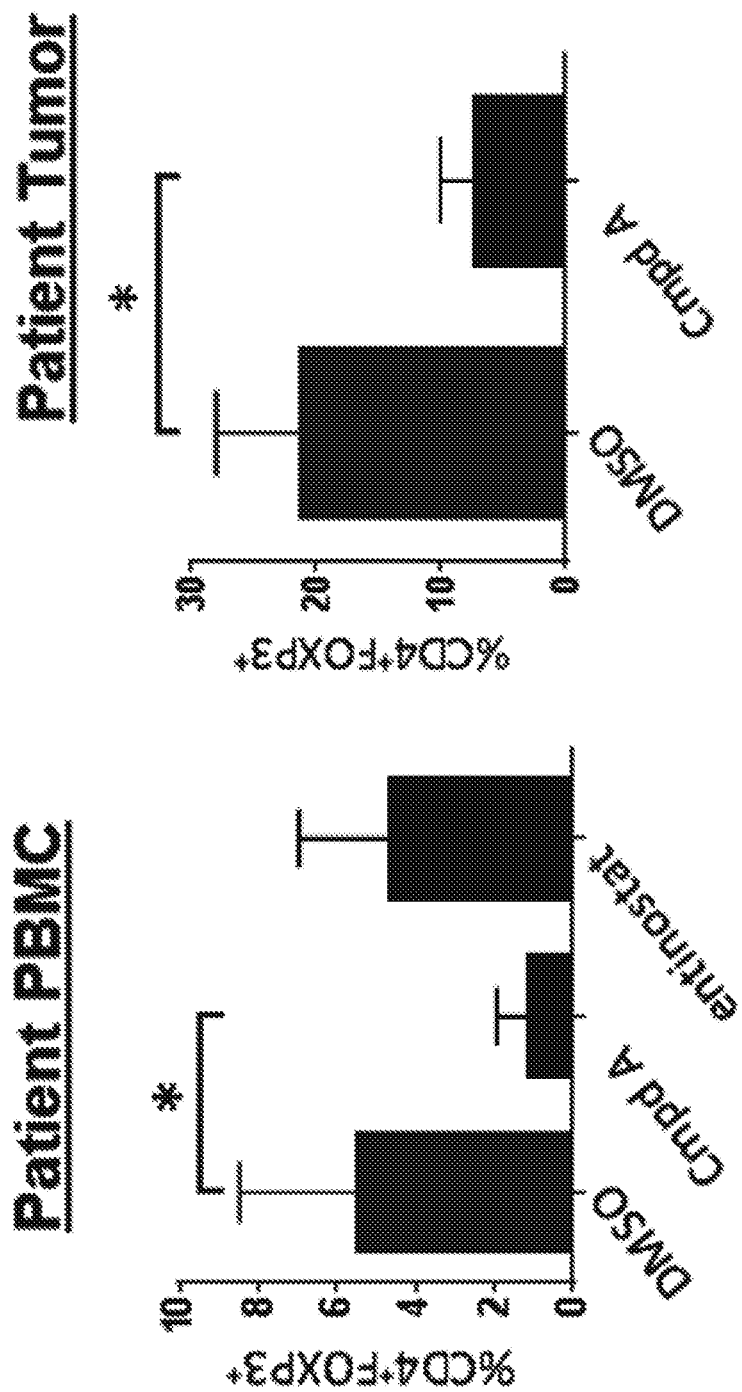
FIG. 2A shows percentage of CD4+FOXP3+ Treg cells in PBMCs from NSCLC patients that were cultured with Compound A or entinostat for 24 hours. Data represent the mean±SEM of samples analyzed from 4 patients. * indicates p-value<0.05.
FIG. 2B shows percentage of CD4+FOXP3+ Treg cells in tumors of NSCLC patients that were cultured with Compound A for 72 hours. Data represent the mean±SEM of samples analyzed from 4 patients. * indicates p-value<0.05.

Next, PBMCs obtained from non-small cell lung cancer (NSCLC) patients or bulk single cell suspensions collected from dissociated freshly resected tumors were cultured with 2.5 µm Compound A or 2.5 µm entinostat for 24 hours after which the phenotype of CD3-CD14+ monocytes or CD45+CD68+CD11b+ tumor macrophages respectively, were assessed by FACS. DMSO was used as a control. Flow cytometry analysis of leukocyte subsets within the cell cultures revealed that Compound A substantially reduced Treg proportions relative to DMSO treatment in patient PBMCs (FIG. 2A, p=0.04) and in patient tumor cells (FIG. 2B, p=0.05), similar to what was observed in the healthy donor PBMCs (FIG. 1C). Treatment with Compound A also reduced Treg proportions relative to entinostat treatment in patient PBMCs (FIG. 2A).

III. Additional Effects of Compound A or Entinostat

Figure 3A:
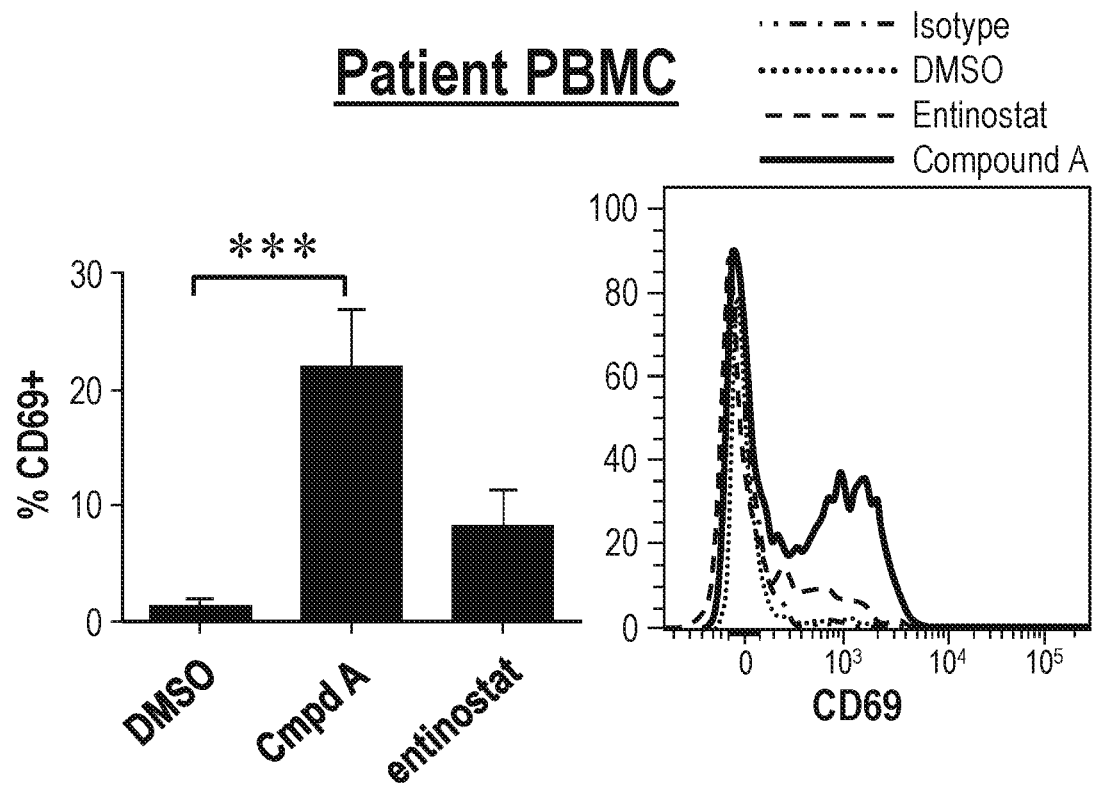
FIG. 3A shows a summary (left), and representative histograms (right) of expression levels of CD69 on gated CD8+ T cells within the PBMCs from NSCLC patients that were cultured with Compound A or entinostat. Data represent the mean±SEM of samples analyzed from 4 NSCLC patients. *** indicates p-value<0.0001.
Figure 3B:
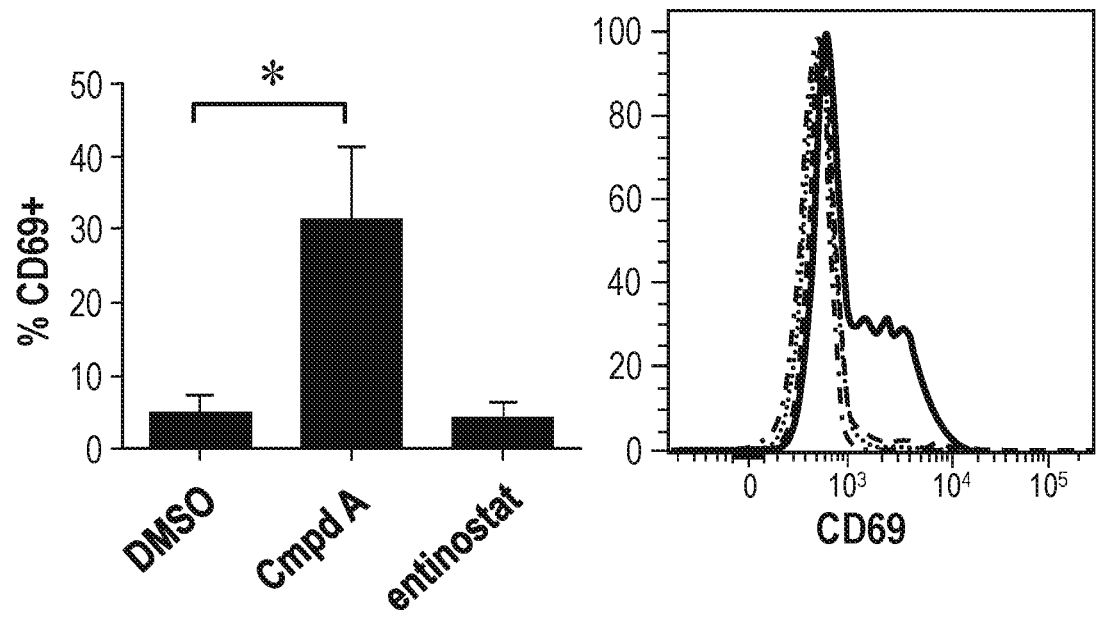
FIG. 3B shows a summary (left), and representative histograms (right) of expression levels of CD69 on gated CD4+ T cells within the PBMCs from NSCLC patients that were cultured with Compound A or entinostat. Data represent the mean±SEM of samples analyzed from 4 NSCLC patients. * indicates p-value<0.05.
Figure 3C:
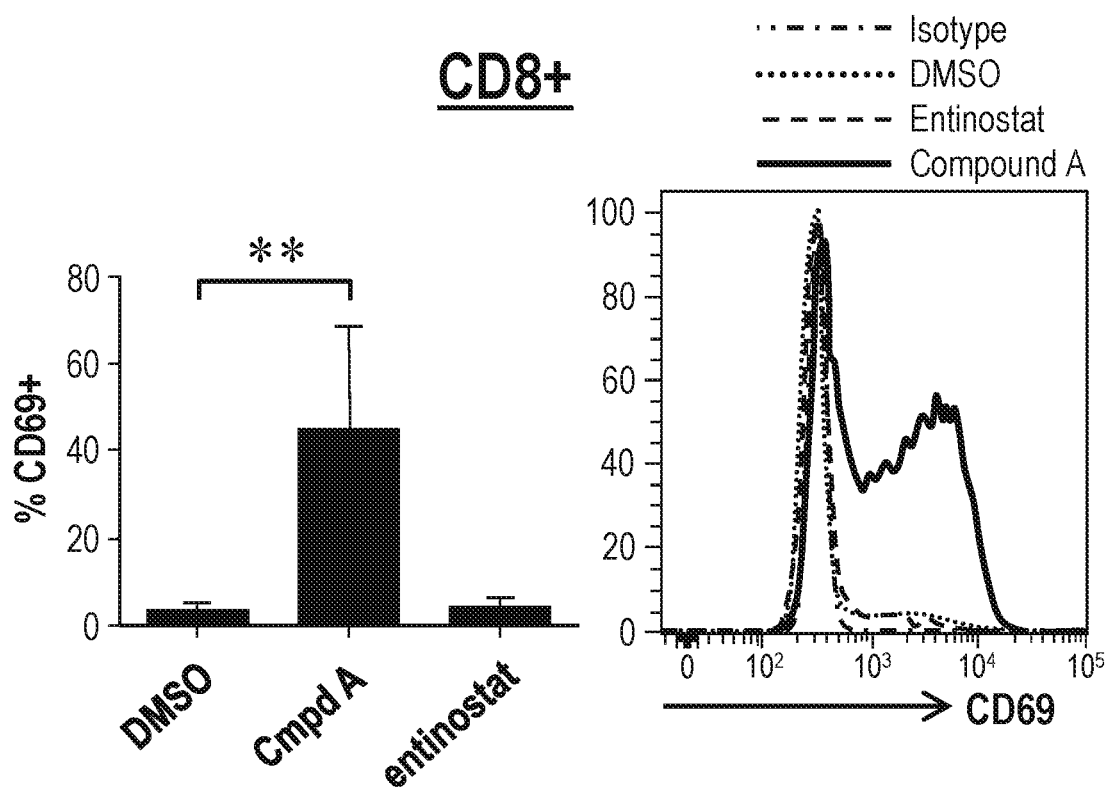
FIG. 3C shows a summary (left), and representative histograms (right) of expression levels of CD69 on gated CD8+ T cells within healthy donor PBMCs that were cultured with Compound A or entinostat for 24 hours. Data represent the mean±SEM of samples analyzed from 8 healthy donors. ** indicates p-value<0.001.
Figure 3D:
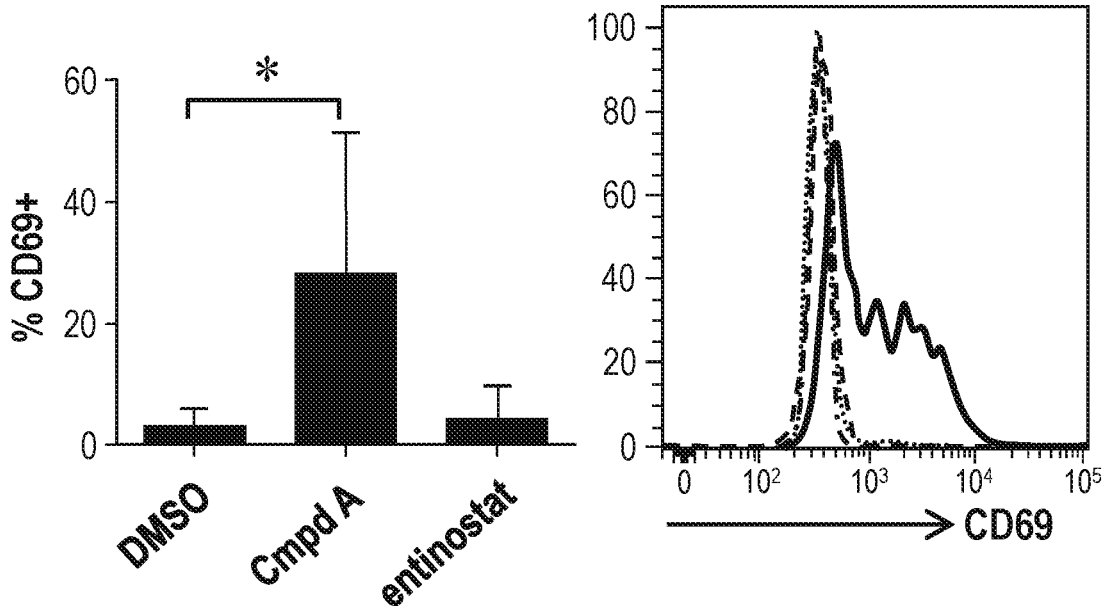
FIG. 3D shows a summary (left), and representative histograms (right) of expression levels of CD69 on gated CD4+ T cells within healthy donor PBMCs that were cultured with Compound A or entinostat for 24 hours. Data represent the mean±SEM of samples analyzed from 8 healthy donors. * indicates p-value<0.05.
Figure 3E:
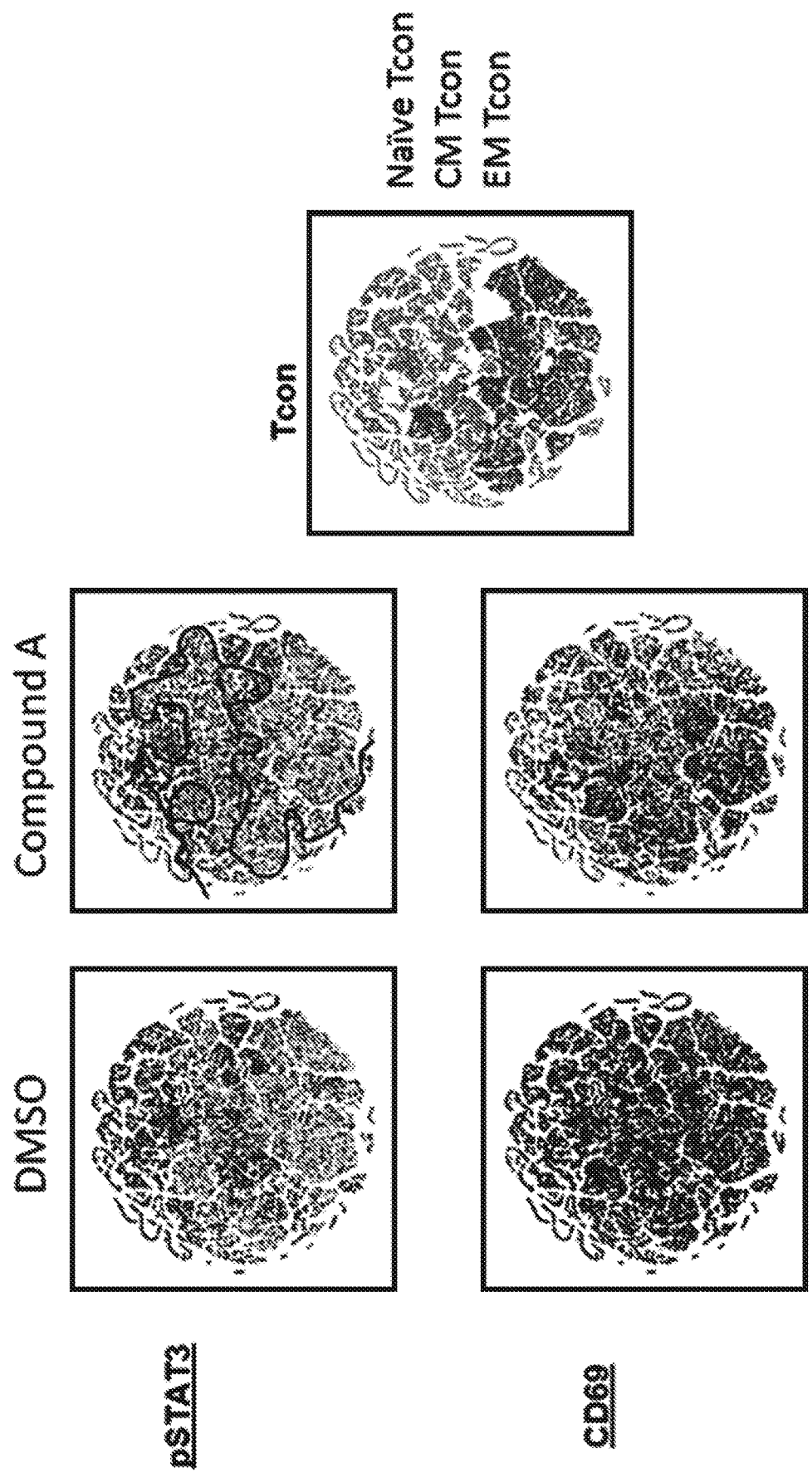
FIG. 3E shows the phenotype of PBMCs that were cultured with Compound A or entinostat and further evaluated by cytoff analysis. Shown is one representative profile for phospho-STAT3 (top) or CD69 (bottom) expression on total CD3+ T cells of three independent experiments analyzed from 3 healthy donors.

Parallel to these observations, expression of the CD69 activation marker was substantially up-regulated on conventional CD8+ and CD4+ T cells in both patient (FIG. 3A, p=0.003; FIG. 3B, p=0.01) and healthy donor PBMC cultures (FIG. 3C, ** indicates p-value<0.001; FIG. 3D, * indicates p-value<0.05) in the presence of Compound A but not entinostat, suggesting an increased activation profile is promoted by Compound A (FIG. 3E).

A HDAC6 selective inhibitor (Compound A) reduced the frequency of CD4+FOXP3+Tregs and promoted transient activation of peripheral and tumor-associated T lymphocytes.

Example 7: HDAC6 Selective Inhibitors and Functional Changes in APCs

Figure 4A:
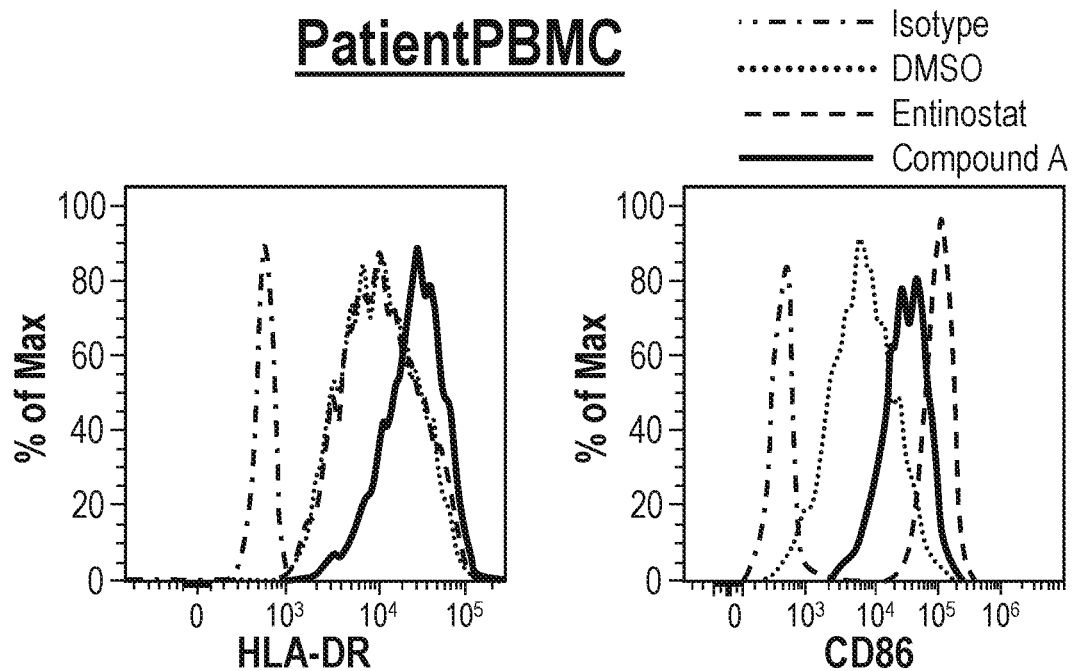
FIG. 4A shows representative histograms of expression levels of MHC class II (left), and co-stimulatory molecule CD86 (right) on gated CD3-CD14+ monocytes from PBMCs from NSCLC patients after culture with indicated HDAC inhibitors for 24 hours. Data represent the mean±SEM of 4 patients.
Figure 4B:
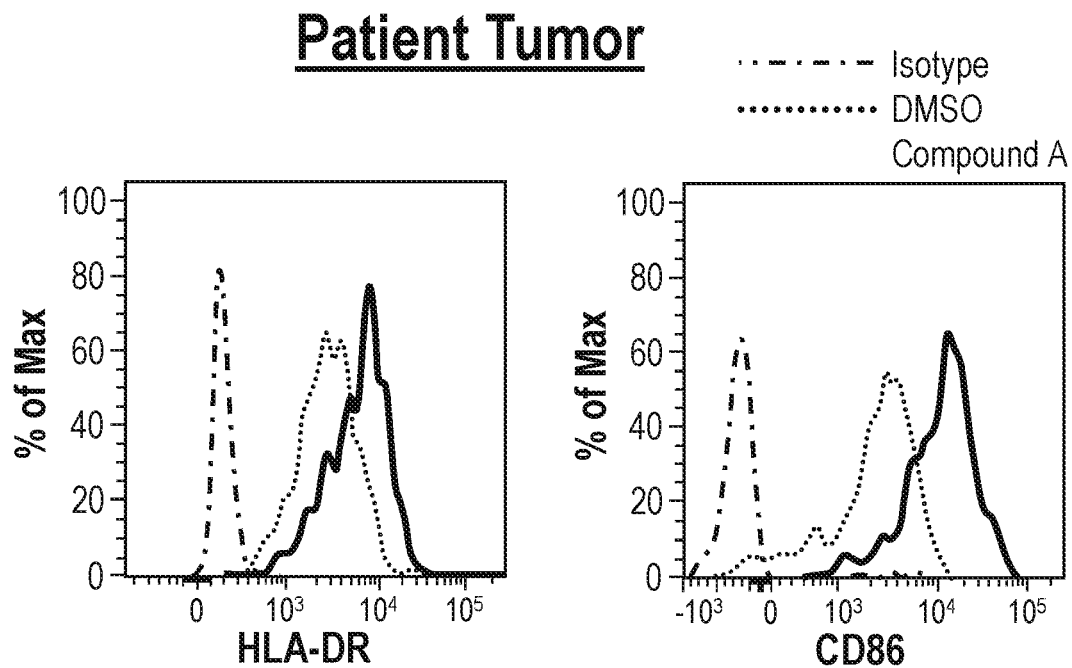
FIG. 4B shows representative histograms of expression levels of MHC class II (left), and co-stimulatory molecule CD86 (right) on CD45+CD68+CD11b+ tumor associated macrophages in debulked tumors after culture with indicated HDAC inhibitors for 24 hours. Data represent the mean±SEM of 4 patients.
Figure 4C:
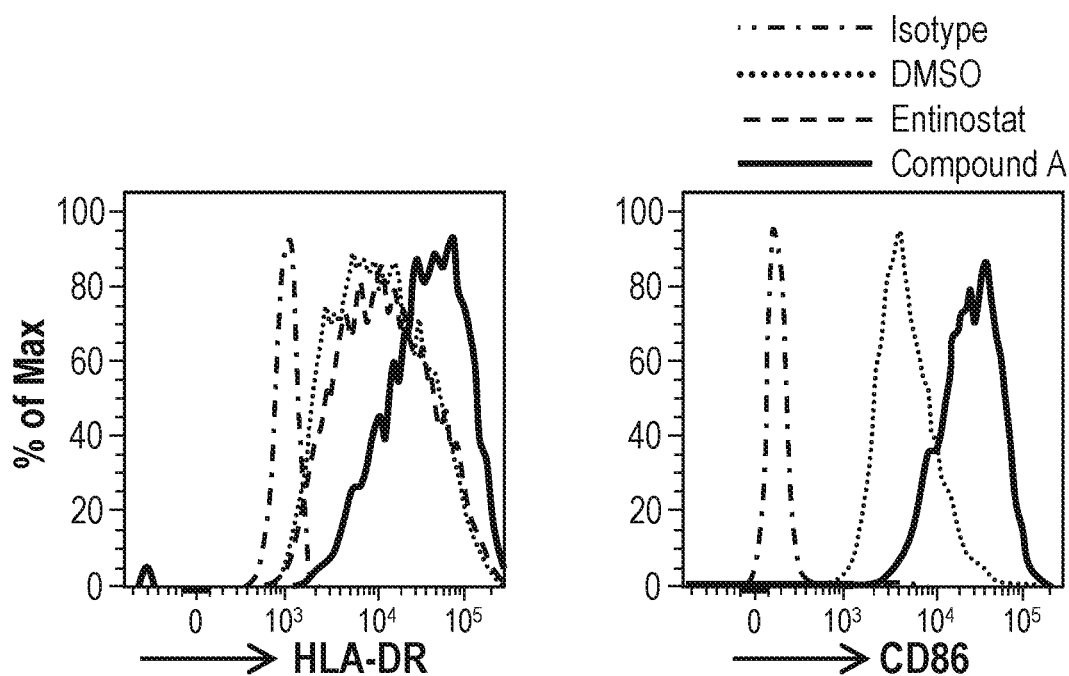
FIG. 4C shows representative histograms of expression levels of MHC class II (left), and co-stimulatory molecule CD86 (right) on gated CD3-CD14+ monocytes in PBMCs from healthy donors after culture with indicated HDAC inhibitors for 24 hours.
Figure 4D:
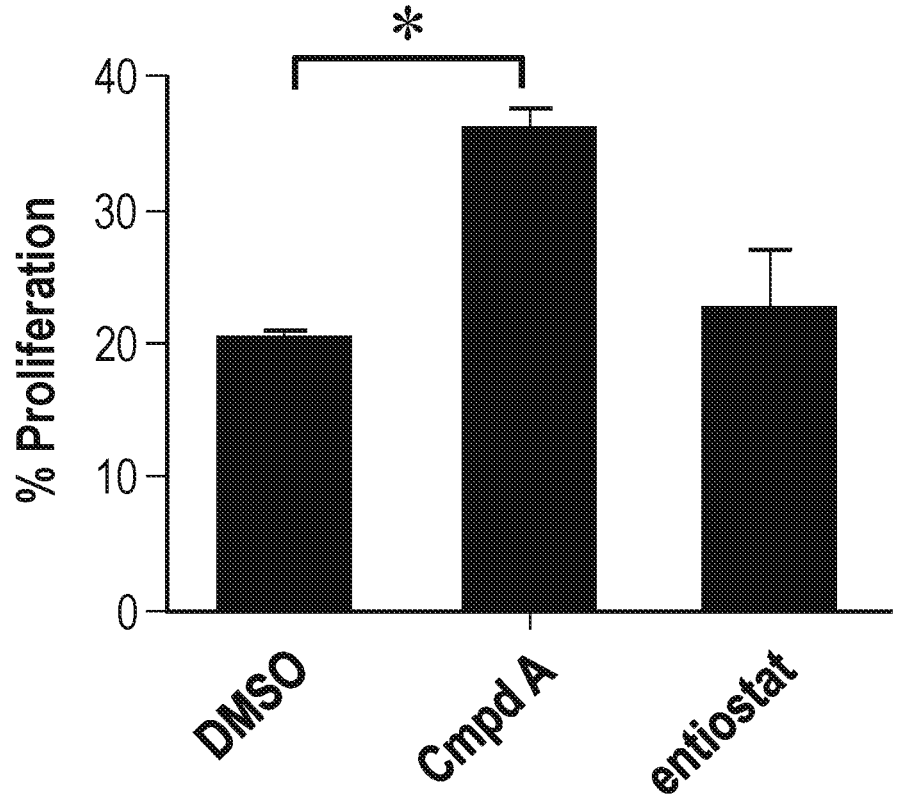
FIG. 4D shows the percentage of proliferation by the responder T cells as determined by CTV dilution in response to stimulation by CD14+ cells. Data represent two independent experiments. * indicates p-value<0.05.

HDAC6 inhibition can effect functional changes in APCs in a mechanism that involves regulation of inflammatory cytokine production. The effects of the HDAC6 selective inhibitor Compound A on APCs with respect to phenotype and function were investigated. Specifically, the phenotype of CD14+CD11b+ monocytes in the peripheral blood of healthy subjects and NSCLC patients, or that of CD14-CD68+CD11b+ macrophages within disaggregated NSCLC tumors were investigated. Upon 24-hour culture with Compound A, the CD14+ monocyte fraction up-regulated expression of MHC class II molecules, as well as CD86 but not CD80, phenotypic changes that are associated with increased priming ability of APCs. In contrast, neither addition of DMSO nor entinostat up-regulated the expression of these proteins (FIG. 4A; p=0.04). A similar pattern of increased expression of MHC class II and CD86 was seen on the CD14-CD68+CD11b+ macrophages within the 2-D tumor cell cultures (FIG. 4B) and in PBMCs obtained from healthy donors (FIG. 4C) when incubated with Compound A. This finding demonstrates a unique modulatory effect of Compound A on human monocytic cells and tumor-associated macrophages, and suggest that it promotes phenotypic changes that would support enhanced antigen presentation and co-stimulatory capabilities. In support of this notion, Compound A exposed CD14+ monocytes were superior at inducing allogeneic T cell proliferative responses in mixed lymphocyte reactions (FIG. 4D). Purified CD14+ cells within patient PBMCs that had been cultured with Compound A or entinostat for 24 hours were incubated with cell trace violet (CTV)-labelled purified T cells from allogeneic donor PBMCs for 6 days in the presence of 20 IU/mL of recombinant human IL-2.

An HDAC6 selective inhibitor (Compound A) promoted increased expression of MHC and co-stimulatory molecules on human monocytes and tumor-associated macrophages and increased their function to stimulate greater T cell proliferation.

Example 8: HDAC6 Selective Inhibitors and Tumor-Associated Immune Cells

Tumor-associated immune cells are important in shaping the course of tumor progression and anti-tumor immunity. The effects of an HDAC6 selective inhibitor on phenotypic and functional changes, especially in the context of tumor antigens, were investigated. Specifically, the effects of an HDAC6 selective inhibitor on immune cells infiltrating lung adenocarcinomas that spontaneously develop in fully immunocompetent genetically engineered mice harboring activating $Kras^{G12D}$ mutation and concurrent p53 loss (designated as KP), or those with T790M/L858R EGFR mutations (designated TL) were studied. Lung tumors (as confirmed by MRI) that spontaneously developed in mice harboring LSL-KrasG12D/p53$^{f/f}$ (KP) or LSL-EGFR (TL) transgenes upon intranasal delivery of adenovirus-cre recombinase were excised after a 7-day treatment with Compound A or vehicle. Single cell suspensions of lung tumor nodules were generated and subjected to FACS analysis to assess the proportions, phenotype and function of CD45+ immune cell subsets in the tumors isolated from both KP and TL mice.

Figure 5A:
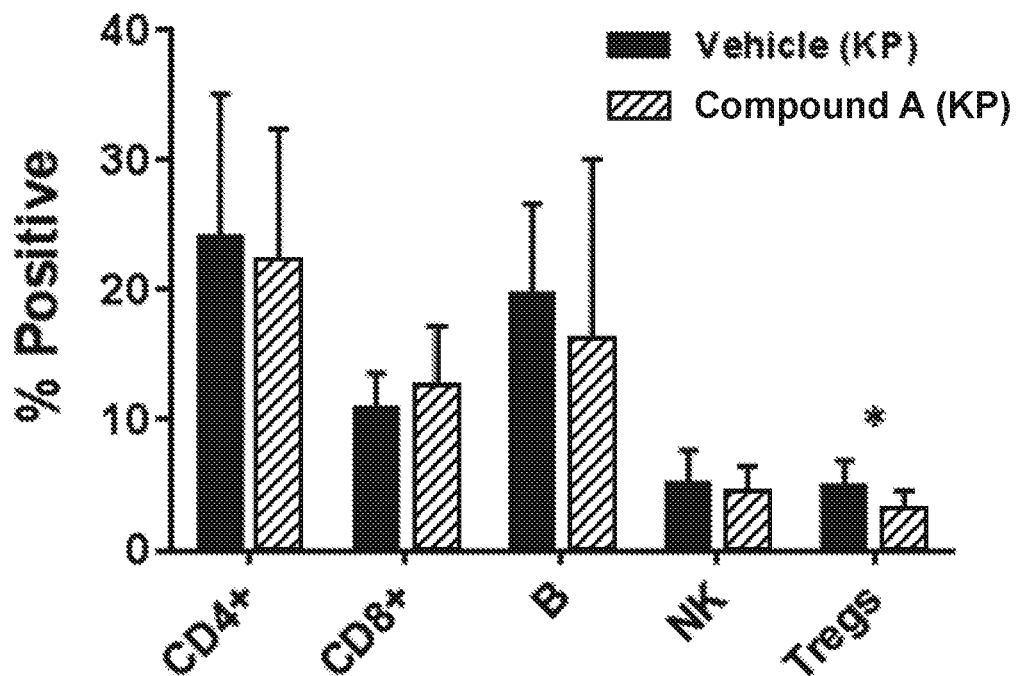
FIG. 5A shows the proportion of indicated lymphoid cell subsets in tumors of KP mice.
Figure 5B:
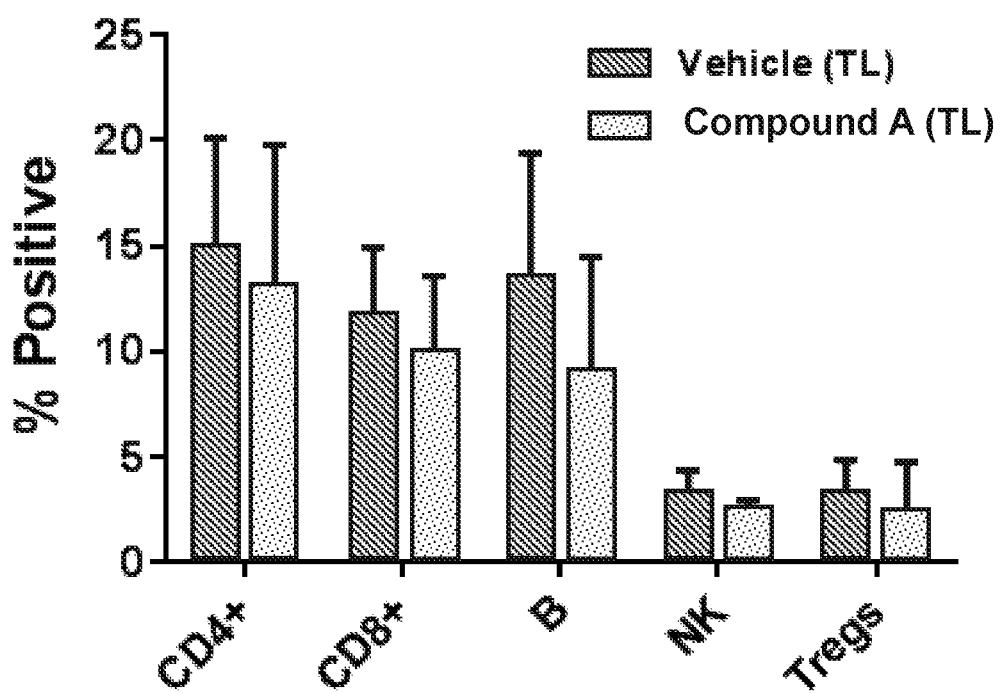
FIG. 5B shows the proportion of indicated lymphoid cell subsets in tumors of TL mice.
Figure 5C:
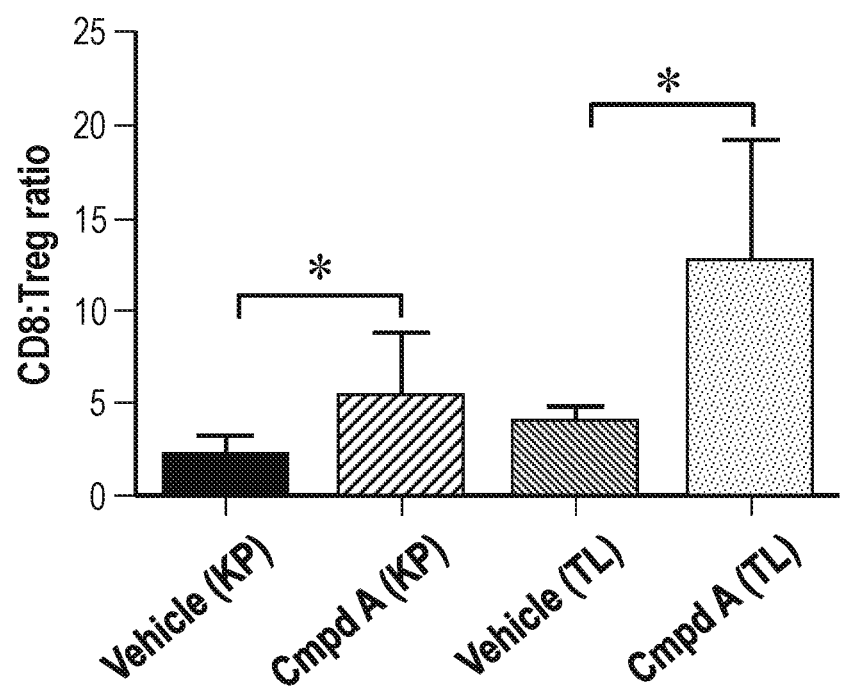
FIG. 5C shows the ratio of CD8+ T cells to CD4+Foxp3+ Treg cells in tumors of KP and TL mice.
Figure 5D:
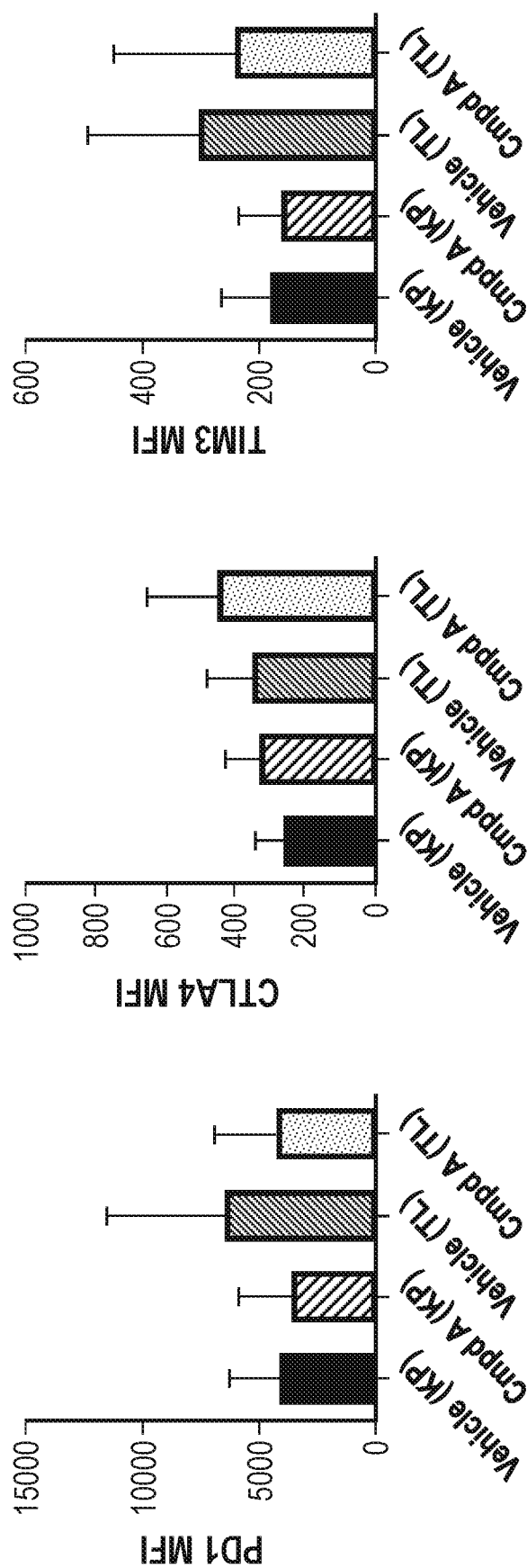
FIG. 5D shows expression levels of PD-1 (left), CTLA-4 (middle), and TIM3 (right) on tumor-infiltrating CD3+CD8+ T cells in mice treated with vehicle or Compound A as indicated. Data are mean±SEM of 5-9 mice per group.
Figure 5E:
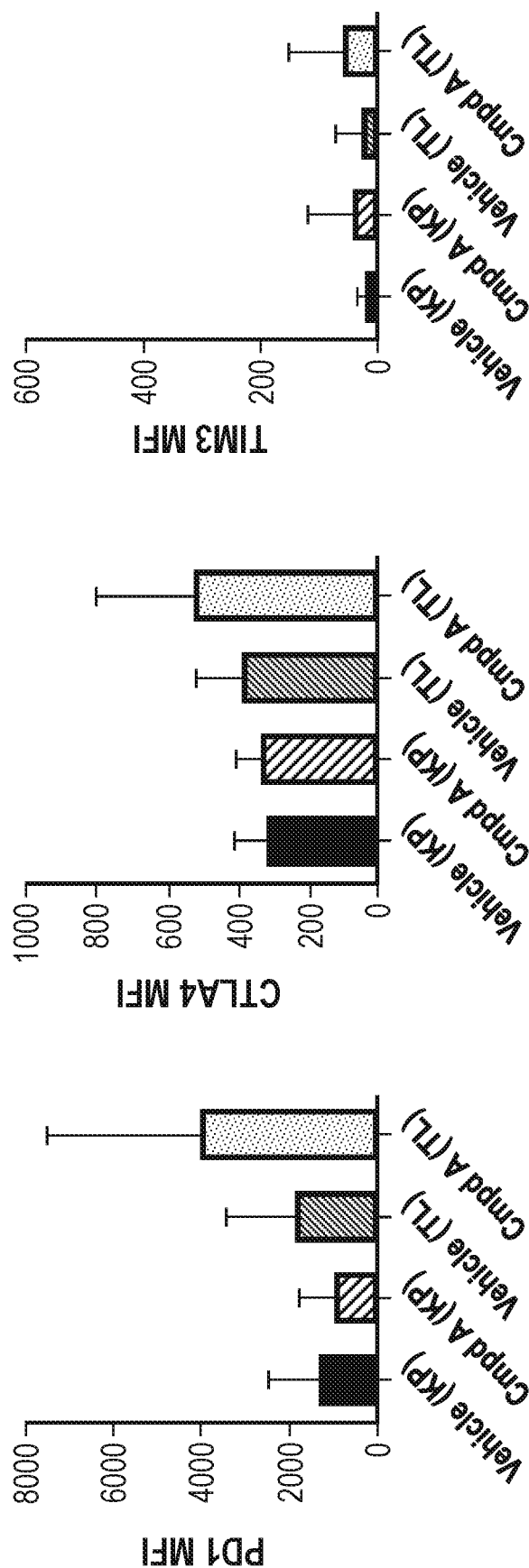
FIG. 5E shows expression levels of PD-1 (left), CTLA-4 (middle), and TIM3 (right) on tumor-infiltrating CD3+CD4+Foxp3− T cells in mice treated with vehicle or Compound A as indicated. Data are mean±SEM of 5-9 mice per group.
Figure 5F:
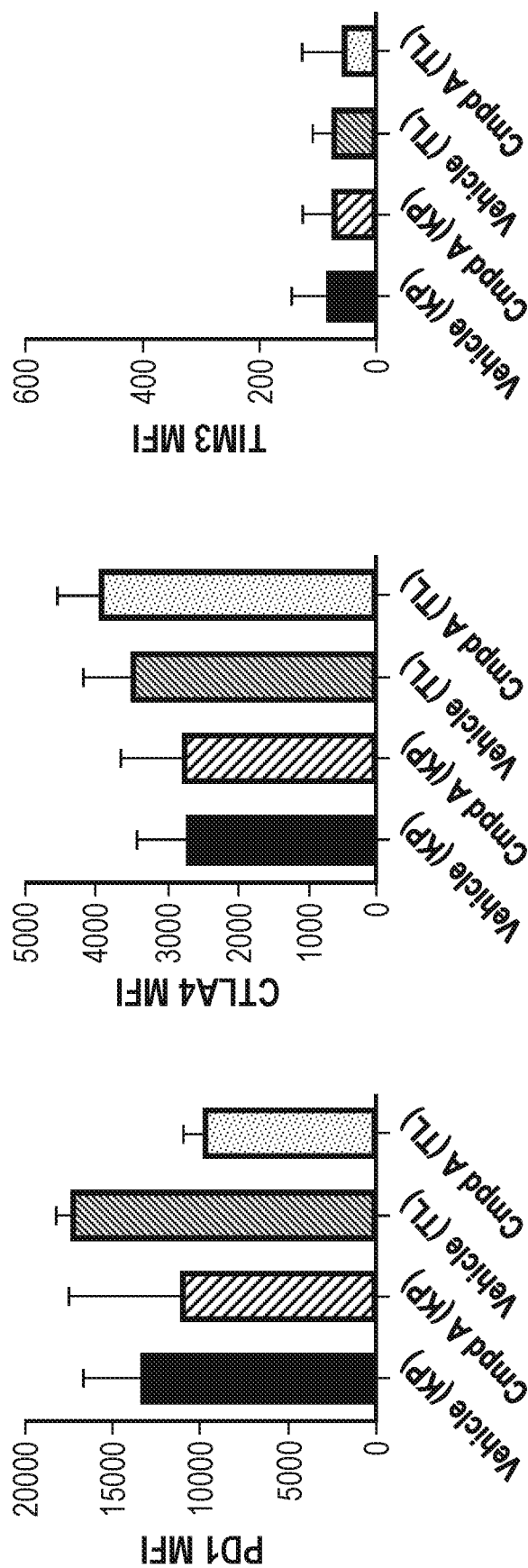
FIG. 5F shows expression levels of PD-1 (left), CTLA-4 (middle), and TIM3 (right) on tumor-infiltrating CD3+CD4+Foxp3+ T cells in mice treated with vehicle or Compound A as indicated. Data are mean±SEM of 5-9 mice per group.
Figure 5G:
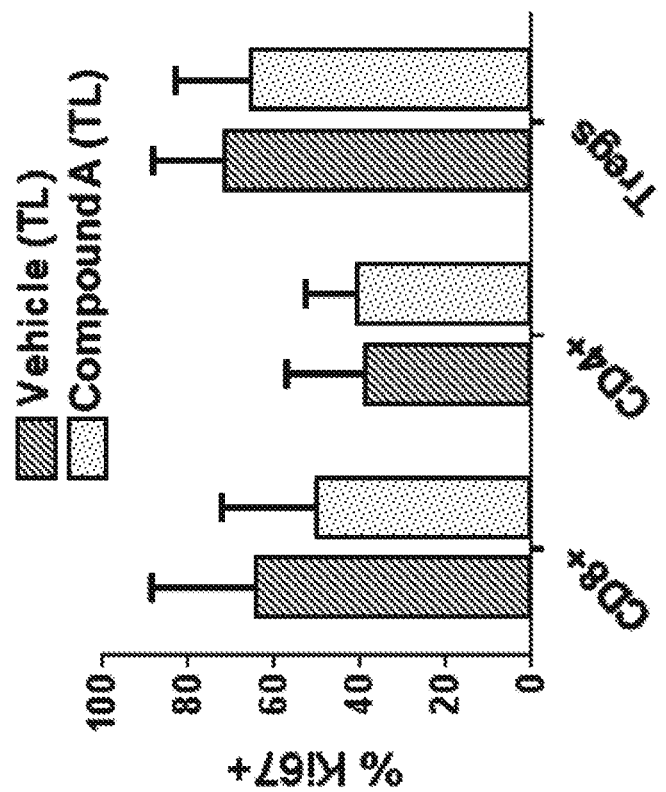
FIG. 5G shows the percentage of indicated T cell subsets expressing Ki67 in tumors of KP (left) or TL (right) mice that were treated with Compound A or vehicle as a control. Data are mean±SEM of 5-9 mice per group.
Figure 5G:
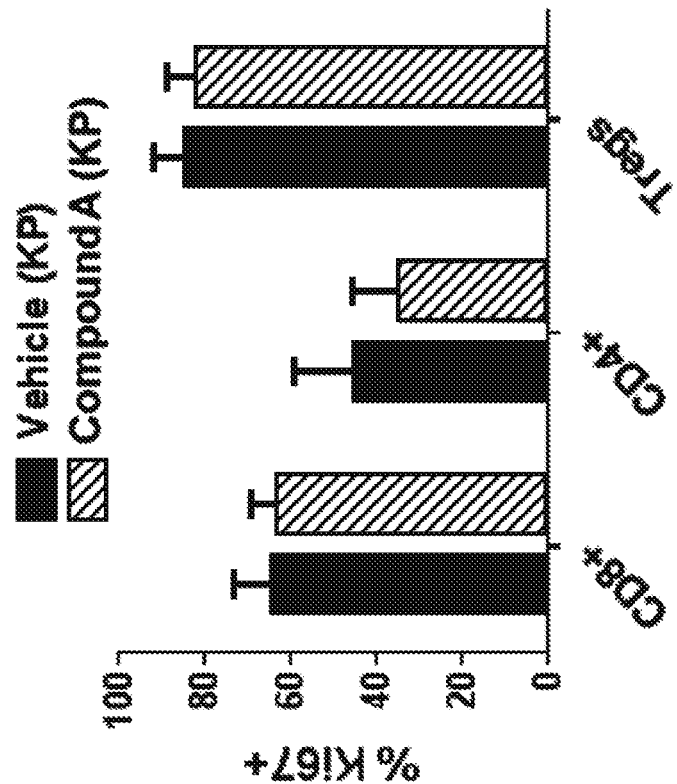
Figure 5H:
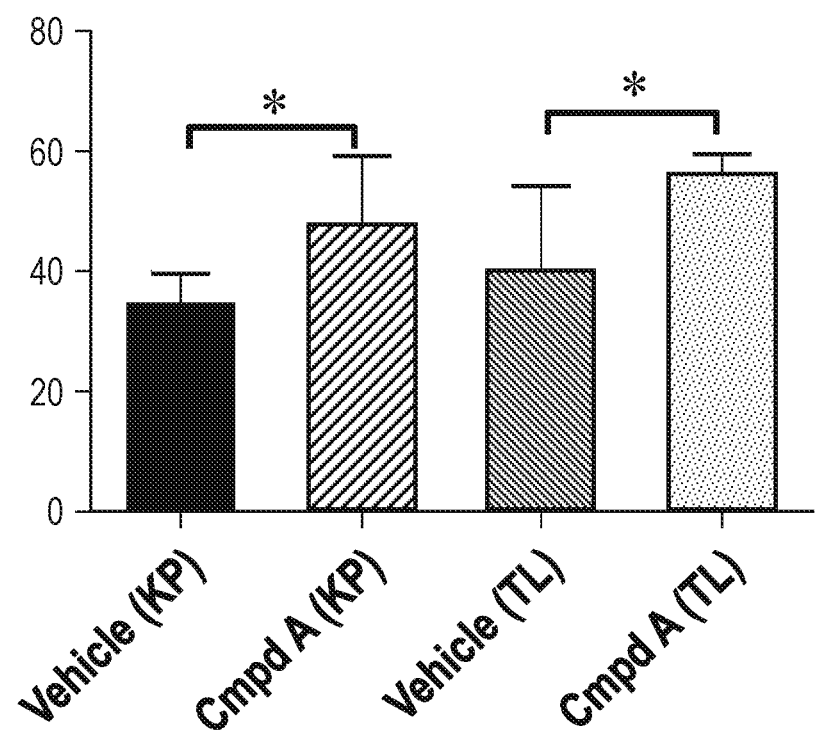
FIG. 5H shows the proportion of tumor-infiltrating CD8+ T cells expressing CD69 activation marker after ex-vivo stimulation. * indicates p-value<0.05.

Mice with existing adenocarcinomas were treated once daily with Compound A for seven days prior to evaluation of dissociated tumors by comprehensive multi-parameter flow cytometry. Under this short-term treatment, modest increases in the frequency of tumor-infiltrating CD8+ T cells and significant decreases in CD4+Foxp3+ Treg cells among lymphoid cells, resulting in a significant elevation of CD8:Treg ratios in treated tumors were observed (FIG. 5A-5C). Such increases in the CD8:Treg ratios are often associated with enhanced anti-tumor response. Although there were no substantial phenotypic changes with respect to inhibitory receptor molecule expression (FIG. 5D-5G), tumor-infiltrating CD8+ T cells in Compound A-treated mice exhibited increased expression levels of CD69 activation marker, and demonstrated enhanced capacity to secrete effector cytokine IFN-γ as well as TNF-α following ex-vivo stimulation when compared with equivalent cells in the vehicle control group (FIG. 5H).

Figure 5I:
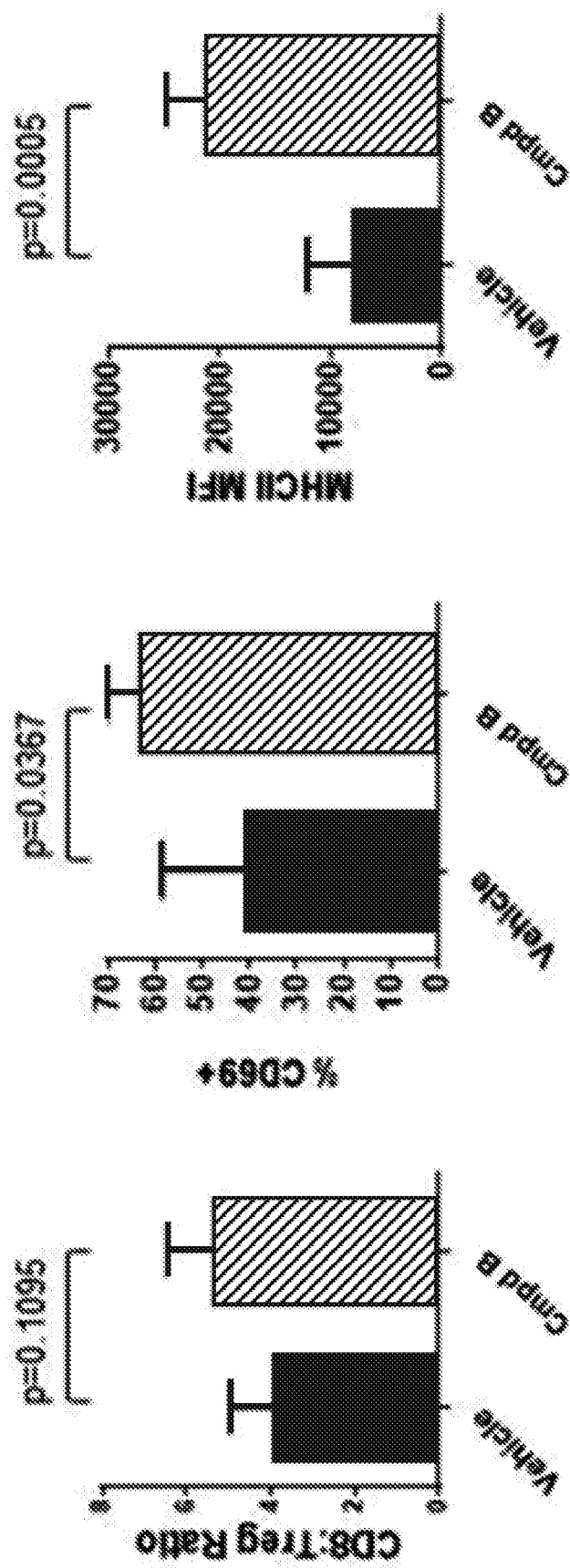
FIG. 5I shows ratio of CD8 to CD4+Foxp3+ Treg cells (left), the percentage of CD8+ T cells expressing CD69 activation marker (middle), and expression levels of MHC class II on macrophages (right) in tumors of KP mice treated with Compound B or vehicle.
Figure 5J:
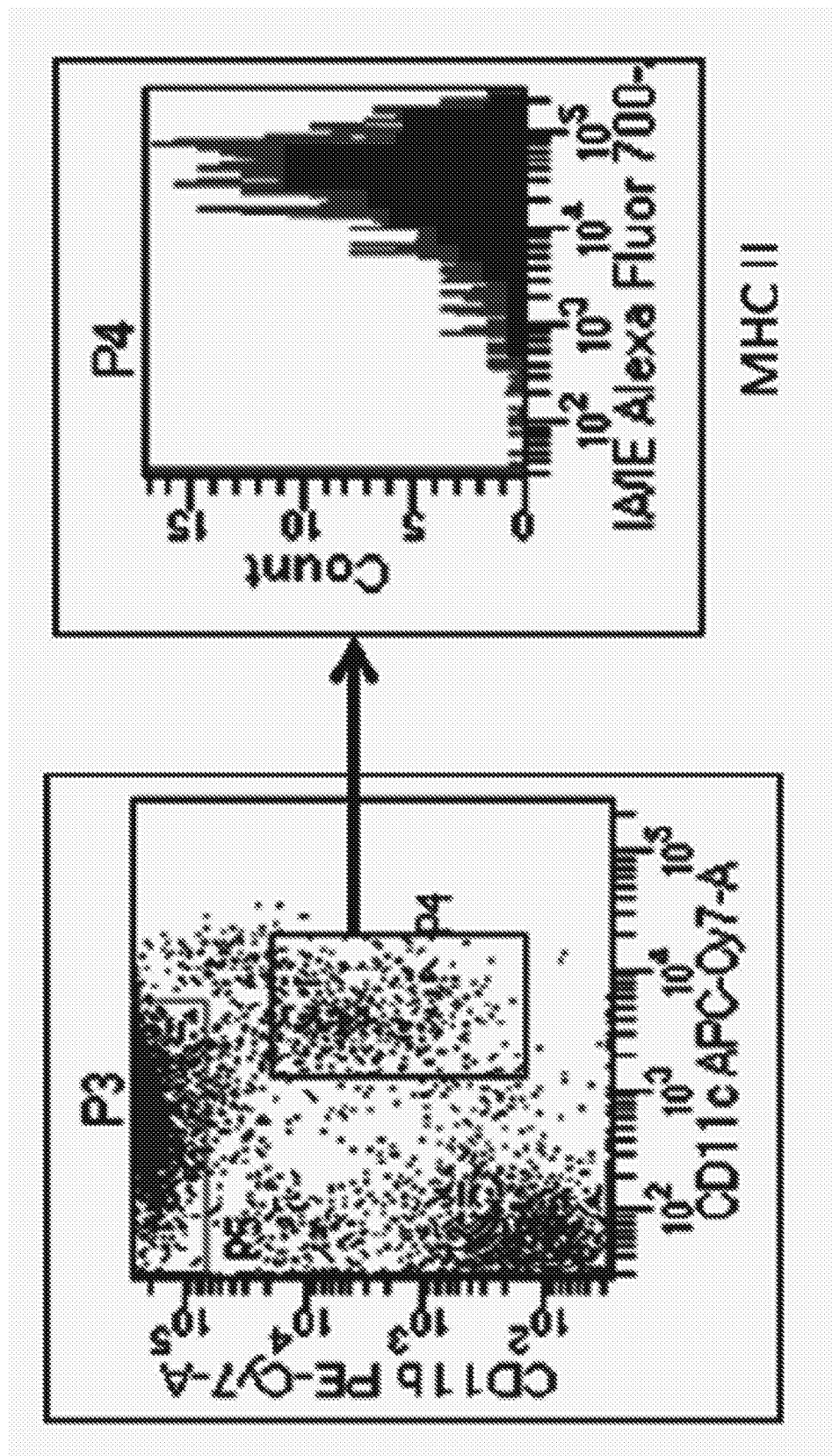
FIG. 5J shows the gating strategy for CD11b$^{lo}$ CD11c+ tumor-associated macrophages (TAMs) in the GEM mice with corresponding histogram plot for MHC class II expression.
Figure 5K:
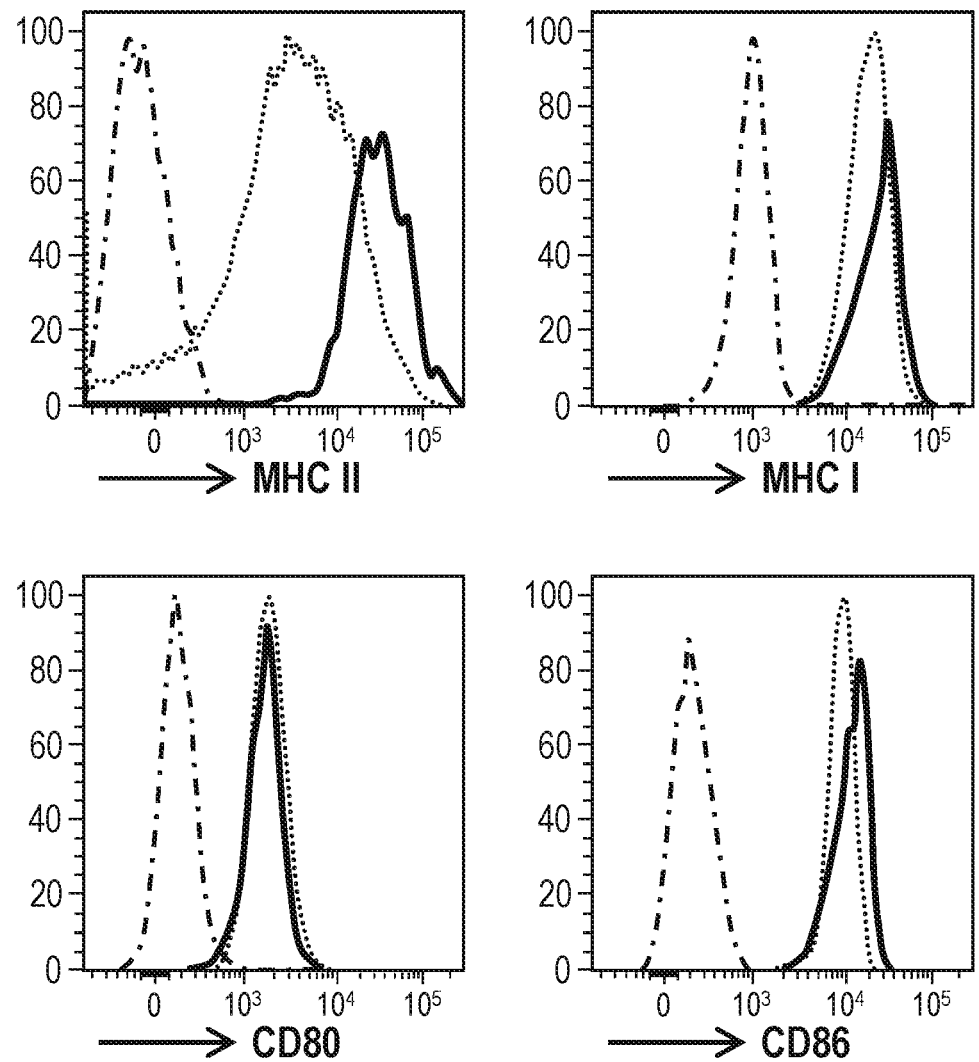
FIG. 5K shows representative histogram plots for the expression levels of MHC class II, CD80, and CD86 in TAMS of KP mice treated as indicated.
Figure 5L:
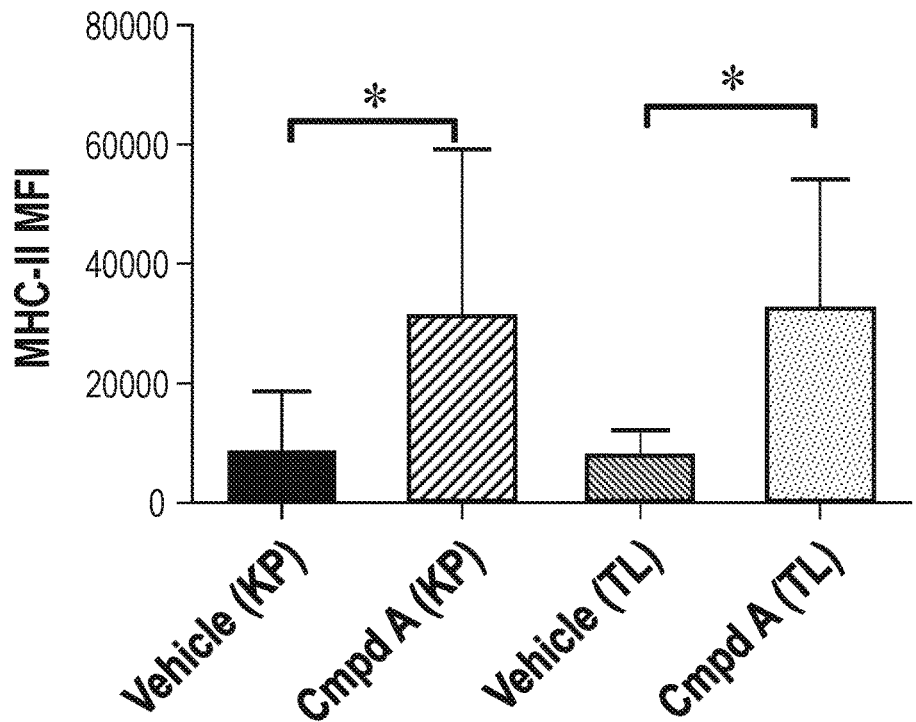
FIG. 5L shows the expression levels of MHC II molecules on tumor-associated CD11c+CD11b$^{lo}$ macrophages in vehicle and Compound A-treated KP and TL mice.
Figure 5M:
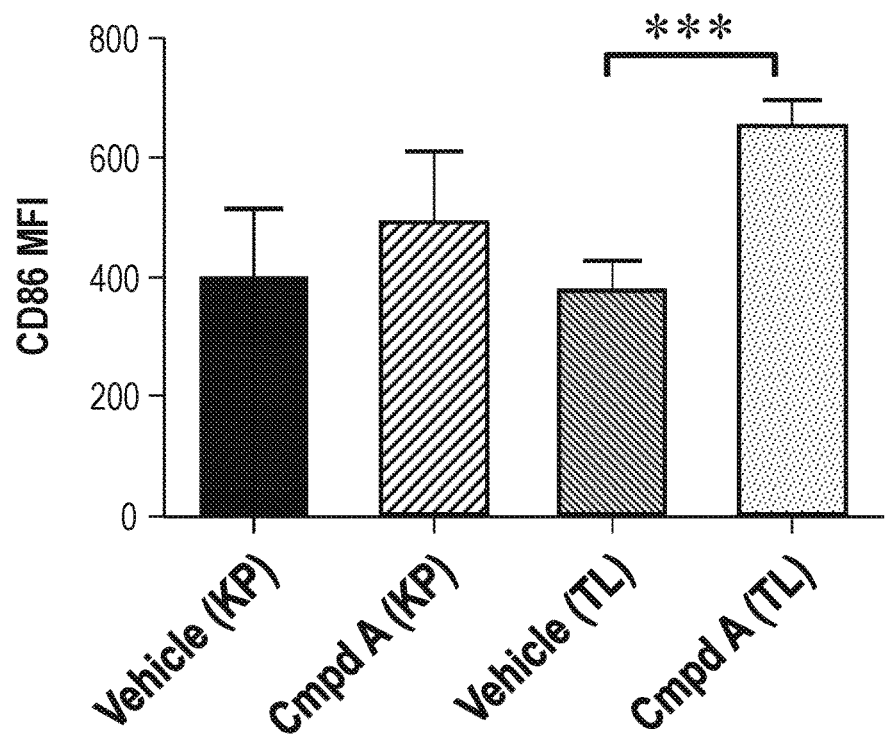
FIG. 5M shows the expression levels of CD86 co-stimulatory molecule on tumor-associated CD11c+CD11b$^{lo}$ macrophages in vehicle and Compound A-treated KP and TL mice.
Figure 5N:
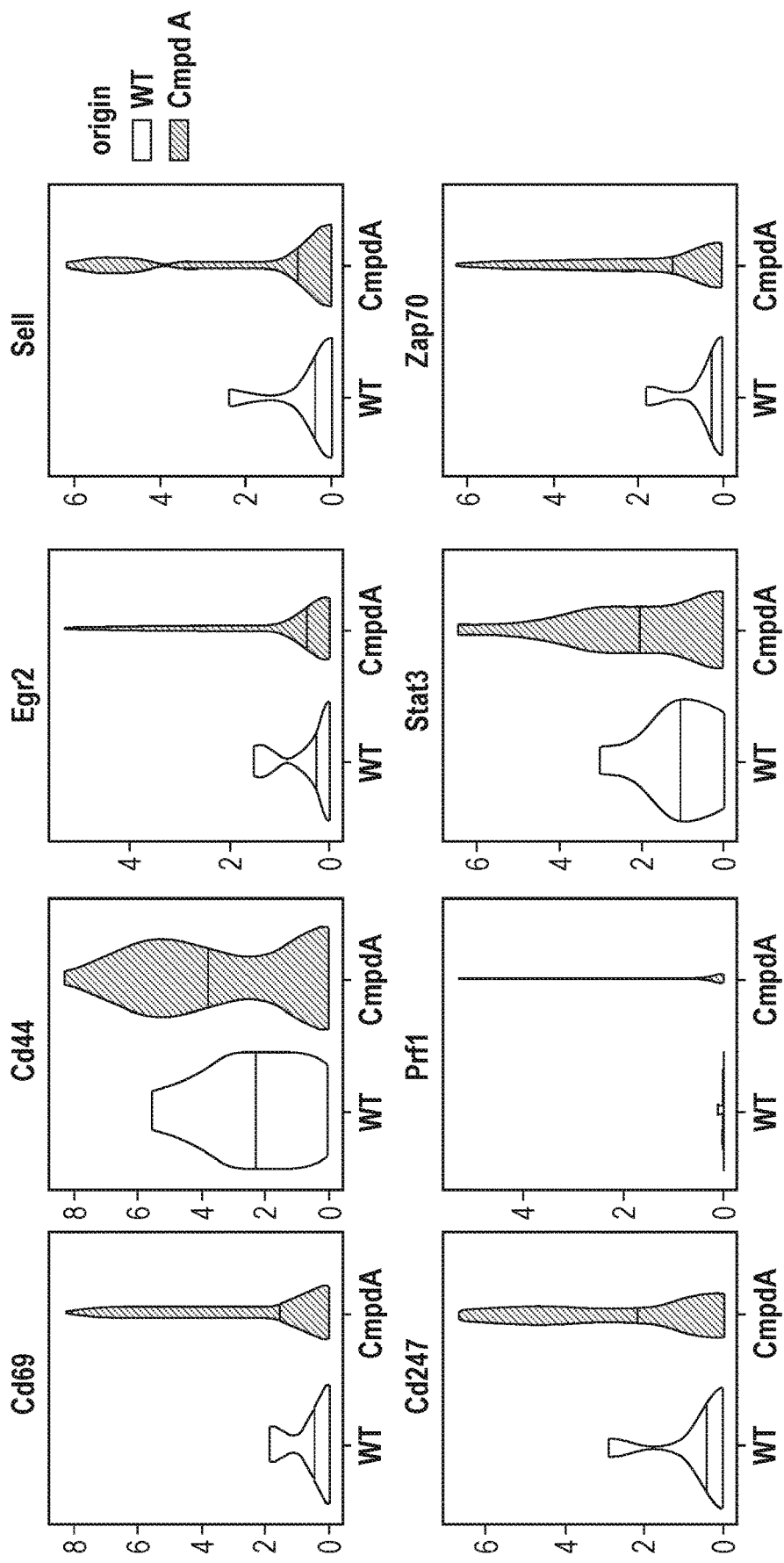
FIG. 5N shows the gene expression profile of CD3+ T cells sorted from tumors of vehicle versus Compound A-treated mice.

In addition, similar to Compound A, Compound B increased the CD8:Treg ratio in the tumors, increased activation of CD8 T cells (per increased CD69 activation marker), and increased expression of MHCII on tumor associated macrophages (FIG. 5I). Single cell suspensions of lung tumor nodules of the KP mice treated with Compound B or vehicle for 7 days were stained and then subjected to FACS analysis to assess proportions, phenotype and function of CD45+ immune cell subsets. Consistent with the findings for Compound A, single cell RNA-Seq revealed that a number of genes associated with T cell activation and effector function including Cd69, Sell (Cd62L), Cd44, and Prf1 (perforin) were up-regulated in tumor-infiltrating T cells from KP mice treated with Compound A when compared to equivalent cells derived from the tumors of the vehicle group (FIG. 5N). Single cell suspensions of lung tumor nodules of the KP and TL mice treated with Compound A or vehicle for 7-days were stained and then subjected to FACS analysis to assess proportions, phenotype and function of CD45+ immune cell subsets. Among myeloid cell populations, the CD11c+CD11b$^{lo}$ tumor-associated macrophages (TAMs; FIG. 5J) showed significantly elevated expression levels of MHC class II as well as the co-stimulatory molecule CD86 (FIGS. 5K-5M). In support of this phenotype, Compound A-exposed TAMS analyzed by single cell RNA-Sequencing showed higher expression of key genes associated with MHC class II expression including Cd74 and H2-Aa relative to their counterparts in the control mice (FIG. 5N).

Figure 6:
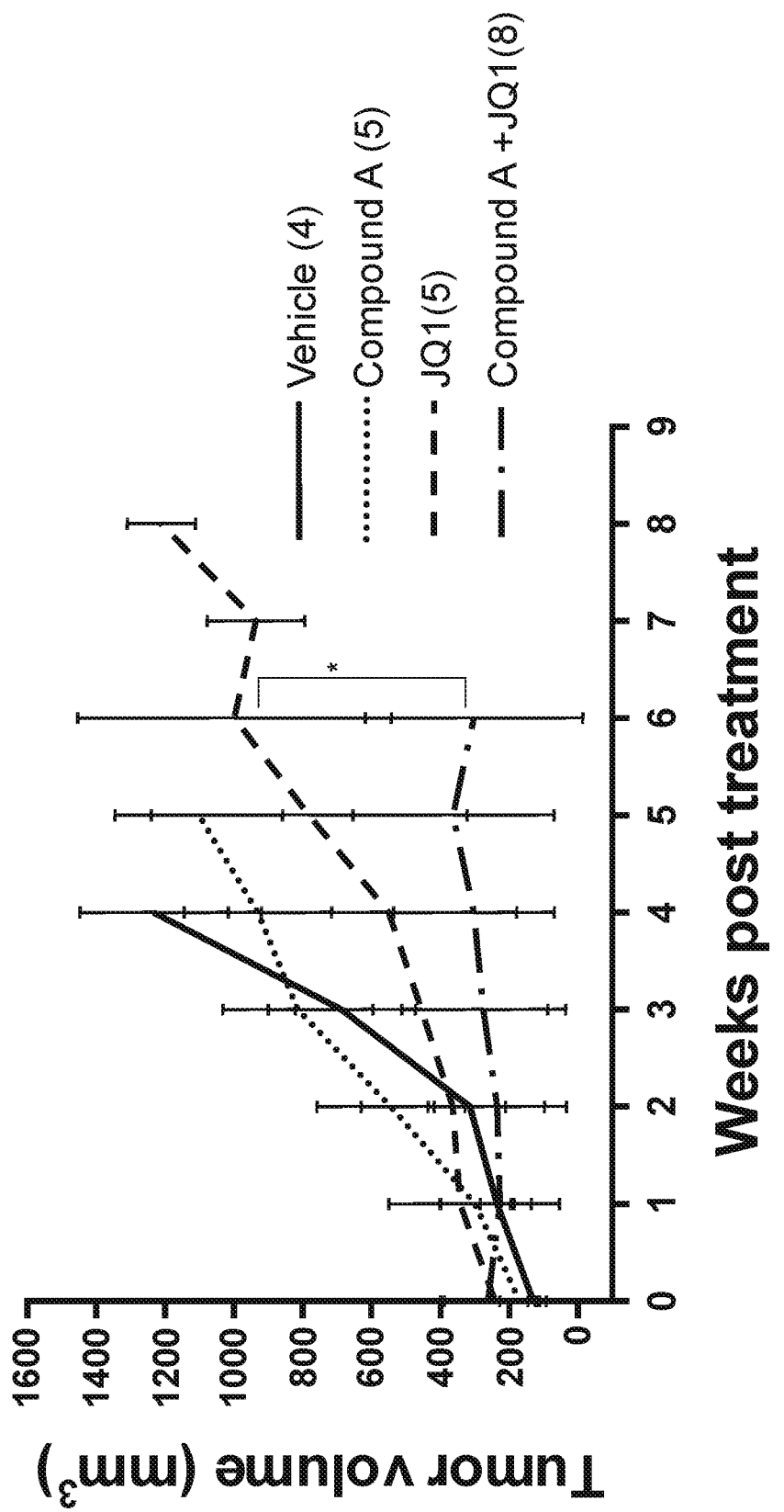
FIG. 6 shows tumor growth kinetics after 2 weeks of treatment with indicated drugs and antibodies. Data are mean±SEM of 4-8 mice per group. * indicates p-value<0.05.

Thus, in line with the in vitro observations, these findings indicated that upon Compound A treatment tumor-infiltrating macrophages underwent changes analogous to APCs that were in a more mature state and that surrounding T cells displayed a more activated/effector profile. Compound A mediated positive immuno-dynamic and phenotypic changes on immune cell subsets. When administered as a single agent, Compound A only resulted in a marginal delay of tumor growth in the immunocompetent genetically engineered mice harboring lung adenocarcinomas with concurrent Kras mutation and p53 deficiency or mutant EGFR (FIG. 6, data not shown). KP mice with tumor burdens of approximately 200 mm$^3$ were injected I.P. once daily with Compound A alone, JQ1 alone, or the combination of the two drugs. Tumor growth was monitored weekly by MRI.

An HDAC6 selective inhibitor (Compound A) promoted phenotypic changes that facilitated tumor-infiltrating T cell priming in a NSCLC model.

Example 9: Compound A Combined with JQ1 in Non-Small Cell Lung Cancer Cells

Figure 7A:
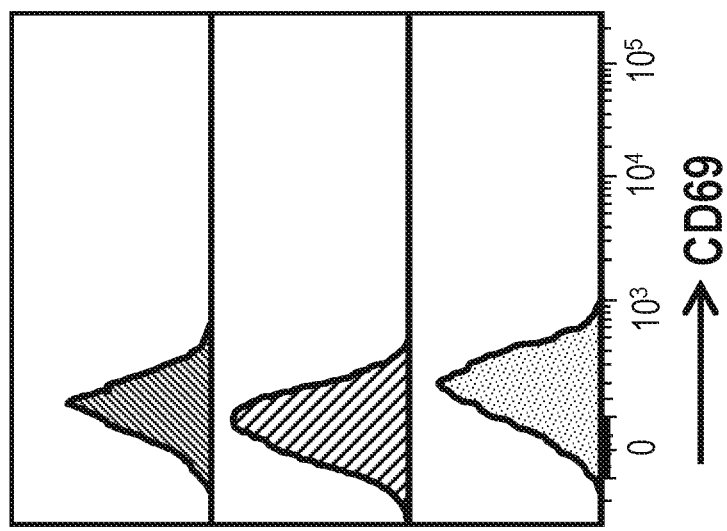
FIG. 7A shows representative histograms for the expression of PD-1 (left) and CD69 (right) on T cells. Data is representative of two independent experiments.
Figure 7A:
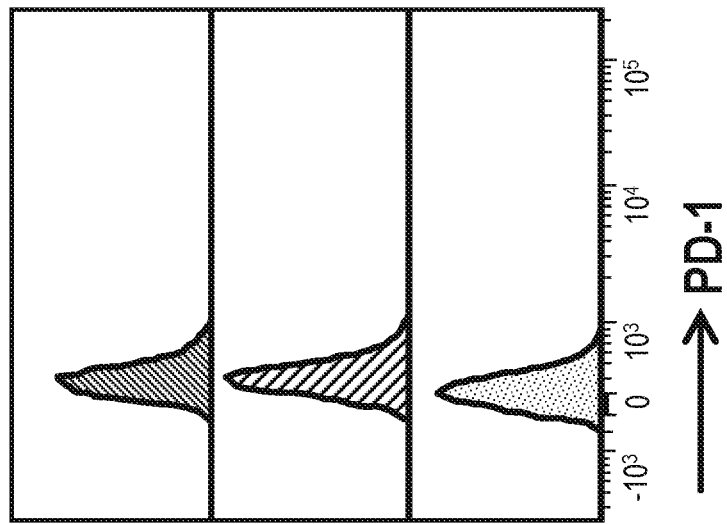
Figure 7A:
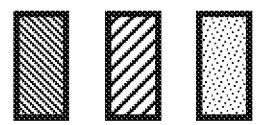
Figure 7B:
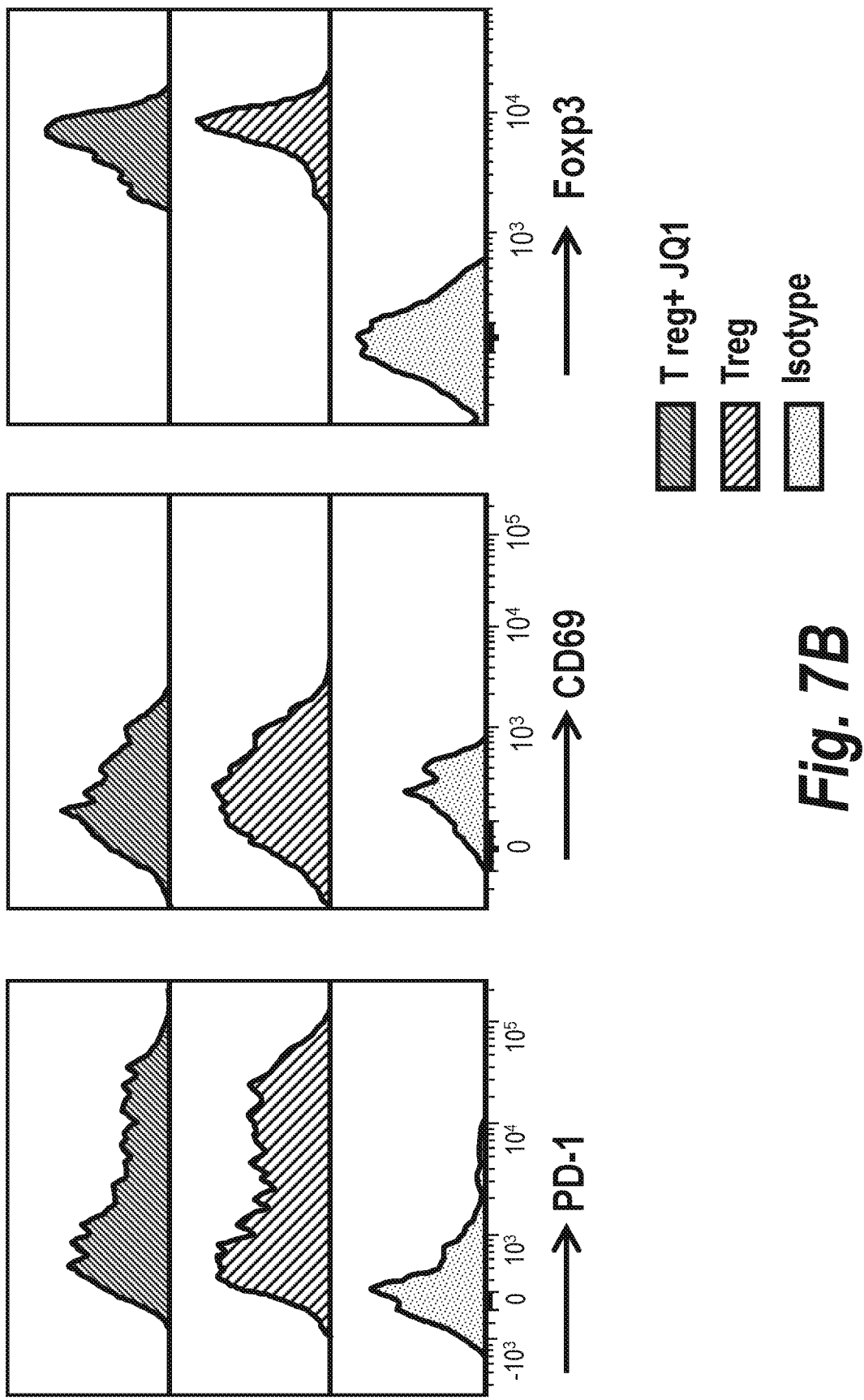
FIG. 7B shows representative histograms for the expression PD-1 (left), CD69 (middle) and Foxp3 (right) on Tregs.
Figure 7C:
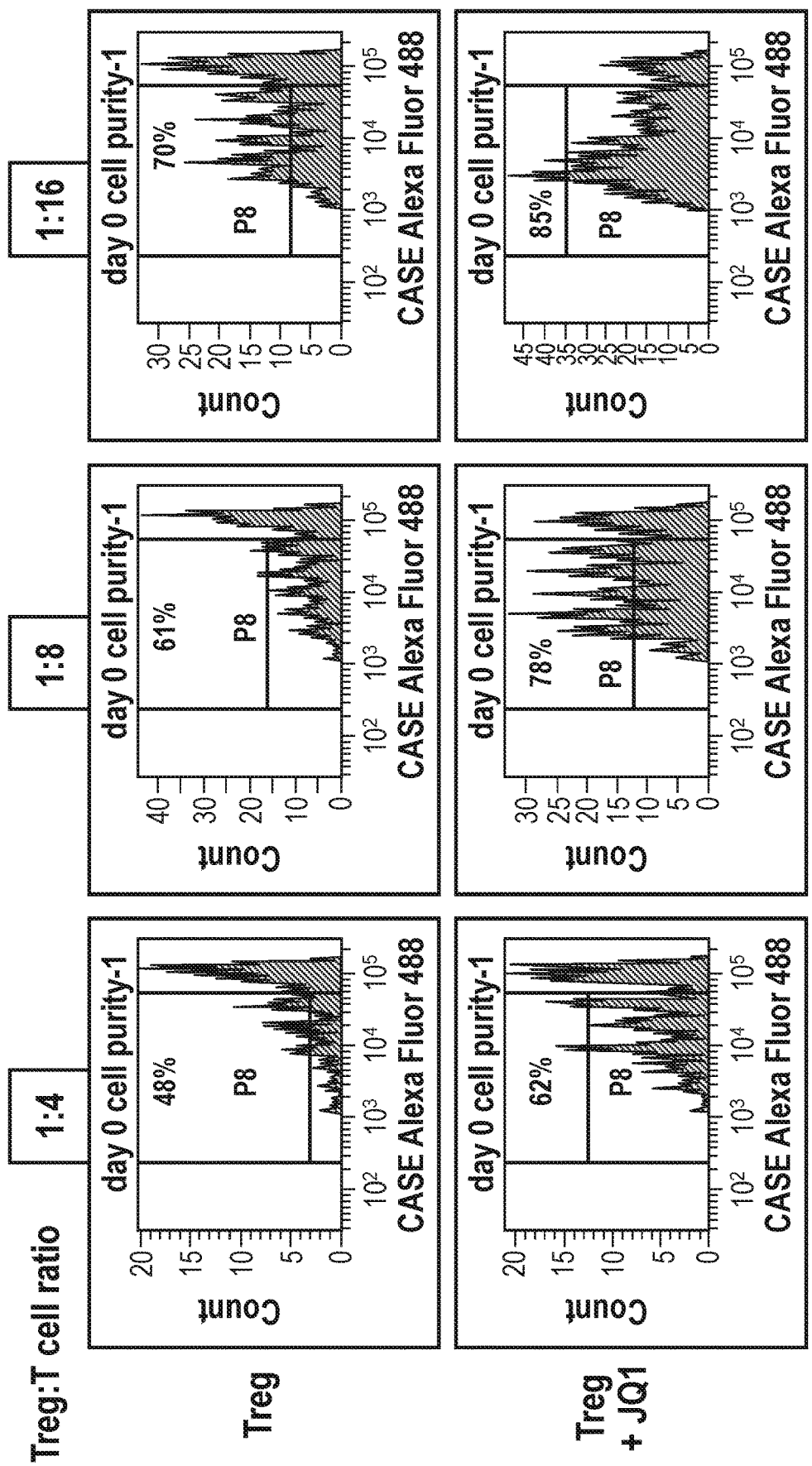
FIG. 7C shows representative histogram plots depicting percent of proliferating cells based on CSFE dilution.

A combination treatment with an HDAC6 selective inhibitor and a complementary immunomodulatory agent can achieve greater levels of immune-based control of tumor growth in these NSCLC models. JQ1 was previously shown to have an anti-tumor effect in KP mice in part due to downregulation of MYC and induction of apoptosis in tumor cells. From the perspective of immune cells, unlike conventional CD8+ T cells, Tregs exposed to JQ1 showed diminished expression levels of PD-1 and Foxp3, and were less suppressive than their unexposed counterparts (FIG. 7A-7C). These JQ1 effects, when combined with the immunomodulatory effects of Compound A, can foster a tumor micro-environment that favors stronger stimulation of tumor infiltrating T cells and an augmented anti-tumor response. T cells were isolated from the spleen of wild-type mice and sorted into CD3+CD25− (T cells) or CD3+CD4+CD25hi (Treg) subsets and subsequently cultured in the presence or absence of JQ1 (1 µM). Cultures were supplemented with 100 IU/mL of recombinant IL-2. Cells were washed after two days of culture and their phenotype was evaluated by FACS. For the CSFE dilution shown in FIG. 7C, 2×10$^5$ CFSE-labelled purified T cells obtained from the spleen of naïve mice were co-cultured with 1.0×10$^5$ mitomycin C treated, T-depleted spleen cells which served as APCs. 0.5 µg of soluble anti-CD3 was then added to each well along with graded numbers of Tregs (indicated by Treg:T cell ratios).

Figure 8A:
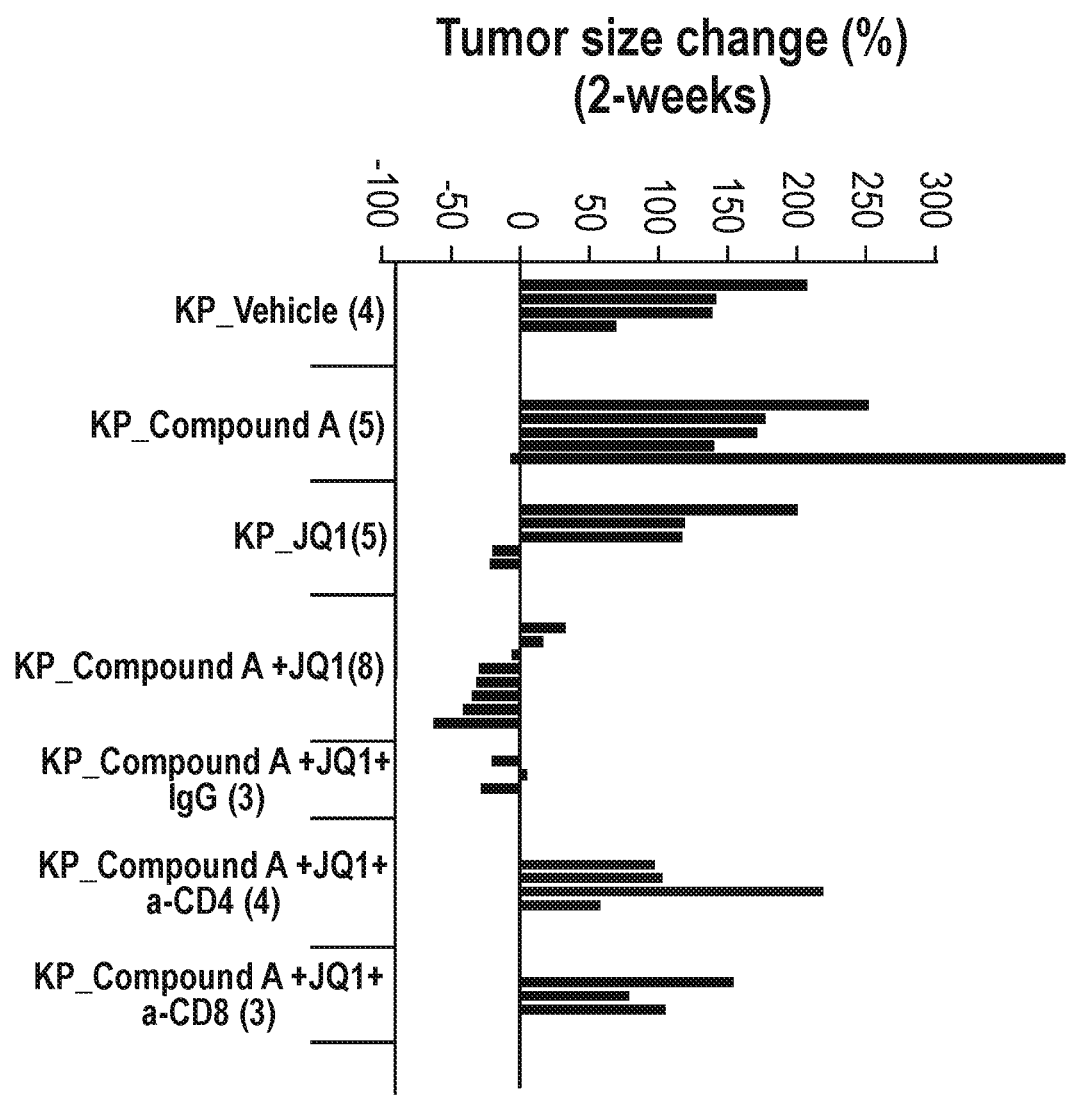
FIG. 8A shows the change in tumor size after 2 weeks of treatment with indicated drugs and antibodies.
Figure 8B:
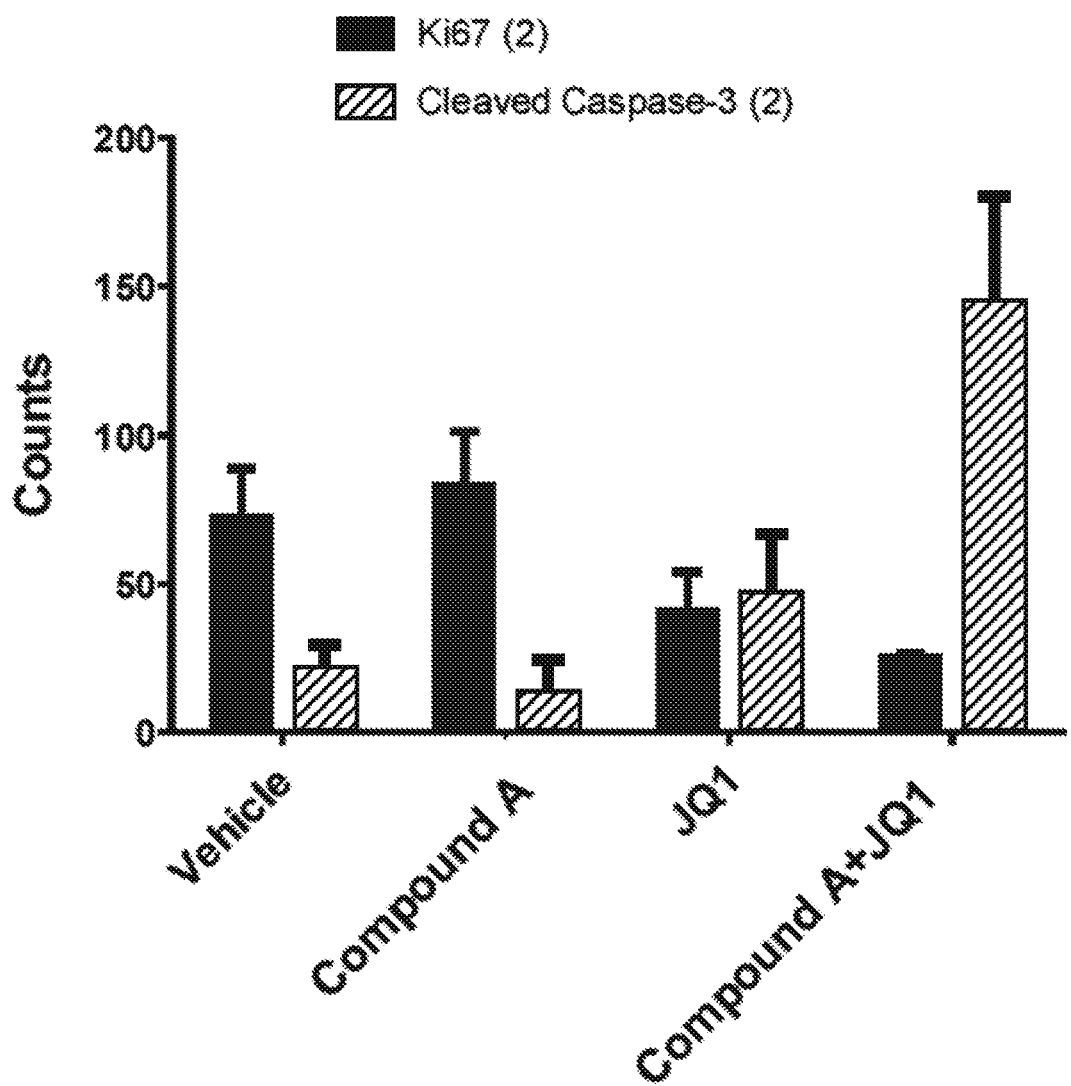
FIG. 8B shows an average of Ki67 positive cells from the selected tumor areas and total cleaved caspase 3 in tumor area of each slide was plotted. Two mice were analyzed.
Figure 8C:
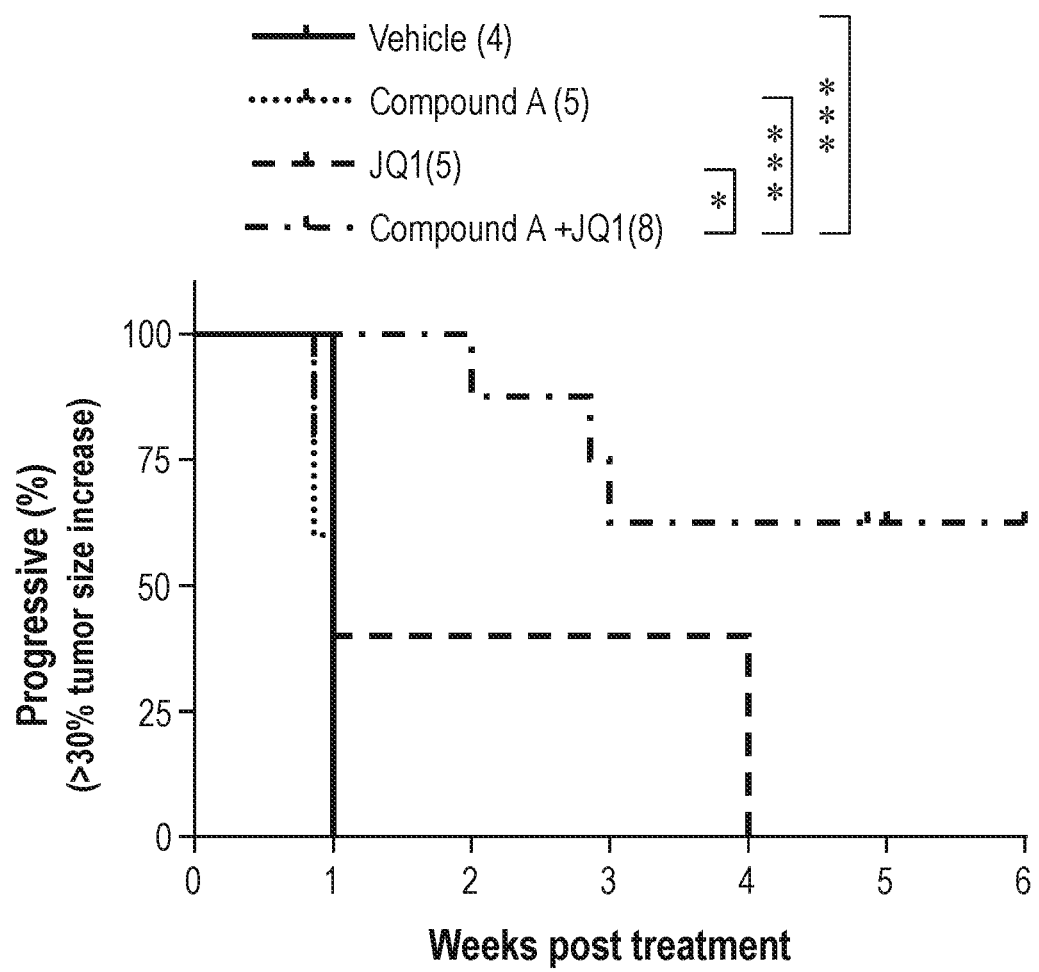
FIG. 8C shows progression free survival of mice in each treatment condition, where disease progression was classified as greater than 30% increase in tumor volume. Data are mean±SEM of 4-8 mice per group. * indicates p-value<0.05,  indicates p-value<0.001, * indicates p-value<0.0001.
Figure 8D:
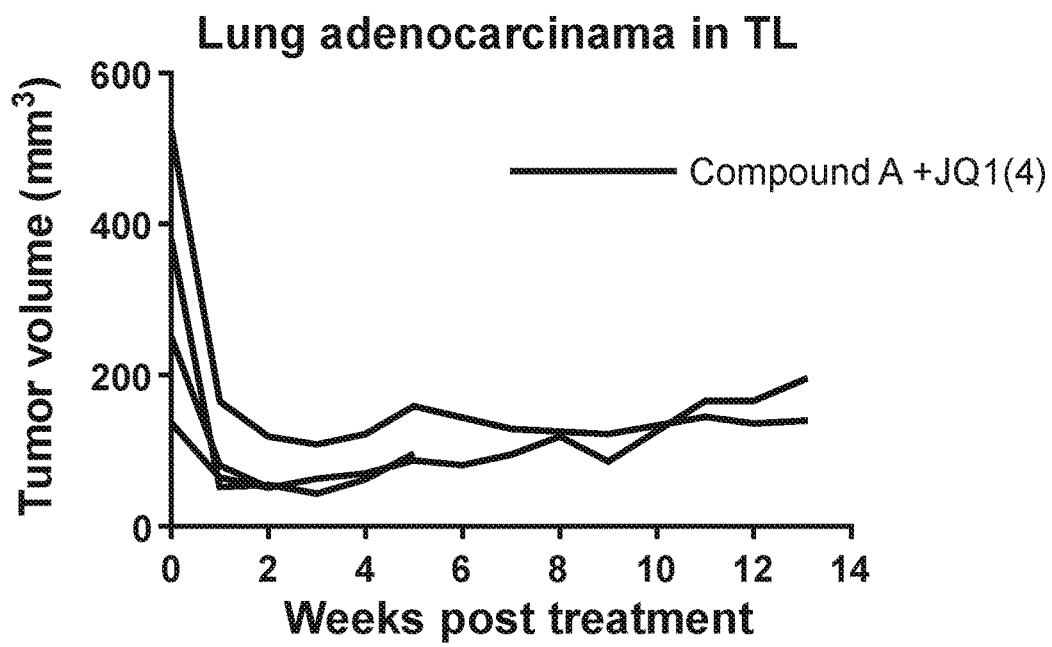
FIG. 8D shows tumor growth kinetics in TL mice. Data are mean±SEM of 5 mice per group.
Figure 8E:
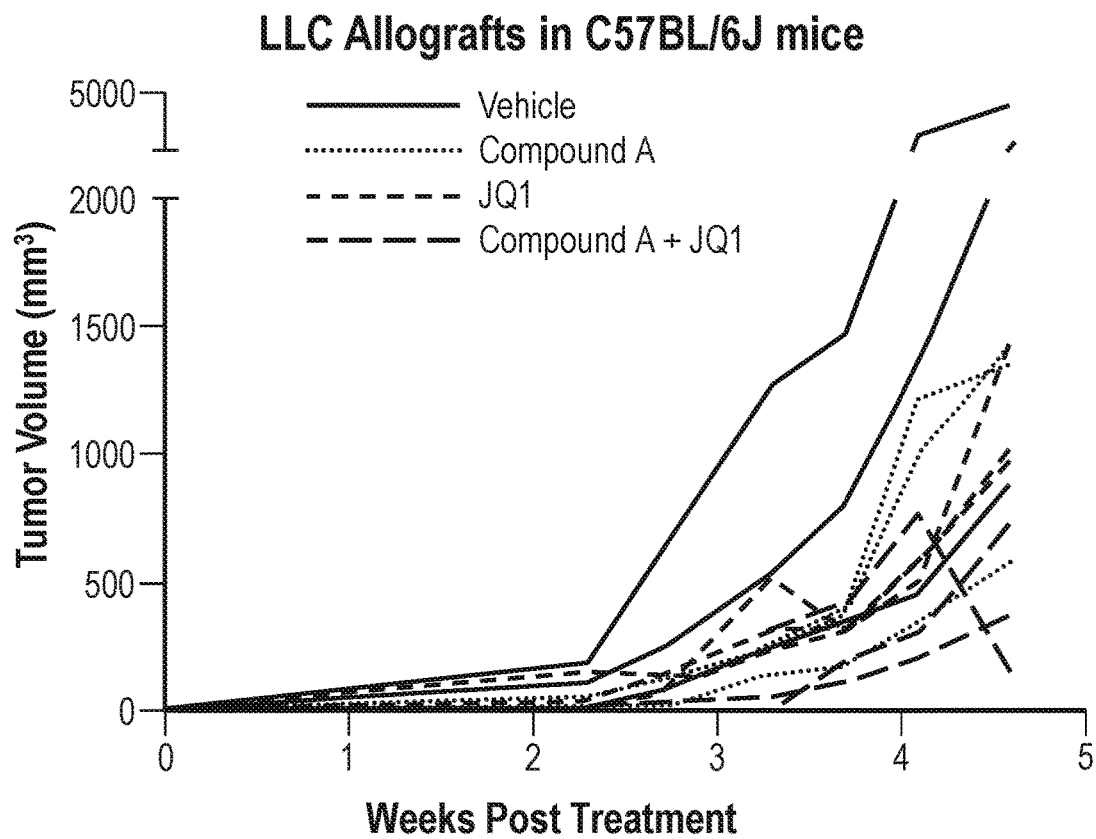
FIG. 8E shows tumor growth kinetics in B6 mice. Data are mean±SEM of 5 mice per group.

Lung adenocarcinoma-bearing mice were treated with Compound A and/or JQ1 in long-term efficacy studies. Tumor-bearing, immune competent mice were administered with a chronic dosing of Compound A and/or JQ1, and tumor growth kinetics were evaluated between the treatment groups versus vehicle-treated controls. Specifically, KP mice with tumor burdens of approximately 200 mm$^3$ were injected I.P. once daily with Compound A alone, JQ1 alone, or the combination of the two drugs with or without depleting antibodies against CD4 or CD8. Tumor growth was monitored weekly by MRI. In KP mice, Compound A or JQ1 monotherapy led to marginal or moderate delay in tumor growth, respectively, but combination treatment with both agents resulted in significant arrest of tumor growth (FIG. 6 and FIG. 8A). These effects were largely dependent on CD8+ and CD4+ T cells as tumor growth arrest noted under the combination of both agents was abrogated upon incorporation of CD8 or CD4-depleting antibodies in the treatment regimen (FIG. 8A). Additionally, decreased ki67 and increased cascape-3 expression in tumor cells occurred with a pharmaceutical combination of Compound A and JQ-1 treatment when compared with the single agent treatments. In particular, KP mice were treated with the vehicle, Compound A, JQ1, or a combination of Compound A and JQ1, for 1-week and then one small lung section was fixed in 10% formalin. This led to reduced proliferation and increased apoptosis of tumor cells upon combination of the two agents (FIG. 8B). Furthermore, the combination therapy led to longer progression-free survival compared to either agent alone (FIG. 8C), suggesting that JQ1 synergized with Compound A to drive T cell-mediated anti-tumor response. Similar to the KP mice, the combination was also efficacious in mice bearing mutant EGFR (TL) lung tumors, as well as Lewis Lung carcinomas, evidenced by marked inhibition of tumor growth in each of these models (FIG. 8D and FIG. 8E). TL mice with tumor burdens of approximately 200 mm$^3$ were injected I.P. once daily with the combination of Compound A and JQ1 and tumor volume measured by MRI (FIG. 8D). Lewis Lung Carcinoma (LLC) cells (500k cells/implantation) were implanted into the C57BL/6 (B6) mice at 1 implantation/mouse. Three days after implantation, the mice were randomly grouped at 5 per group for vehicle, JQ1 and/or Compound A treatment as indicated in FIG. 8E. Tumor was measured twice per week and tumor volume is calculated by 0.5*L*W*W. These data suggest that the therapeutic benefits of this combinatorial approach extend beyond lung adenocarcinomas driven by ectopic expression of driver mutations in the GEMMs to that characterized by spontaneous development and to melanoma.

Figure 9A:
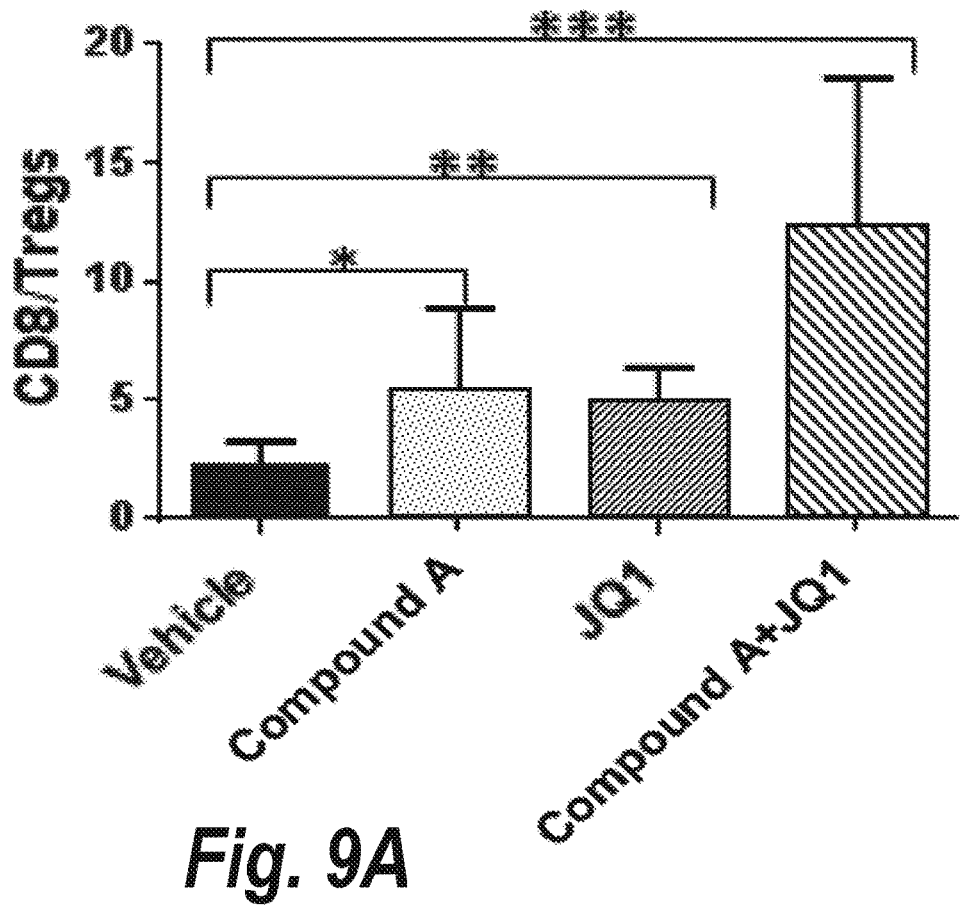
FIG. 9A shows a summary of CD8:Treg ratio in KP mice treated as in FIG. 8A. Data are mean±SEM of 4-8 mice per group.
Figure 9B:
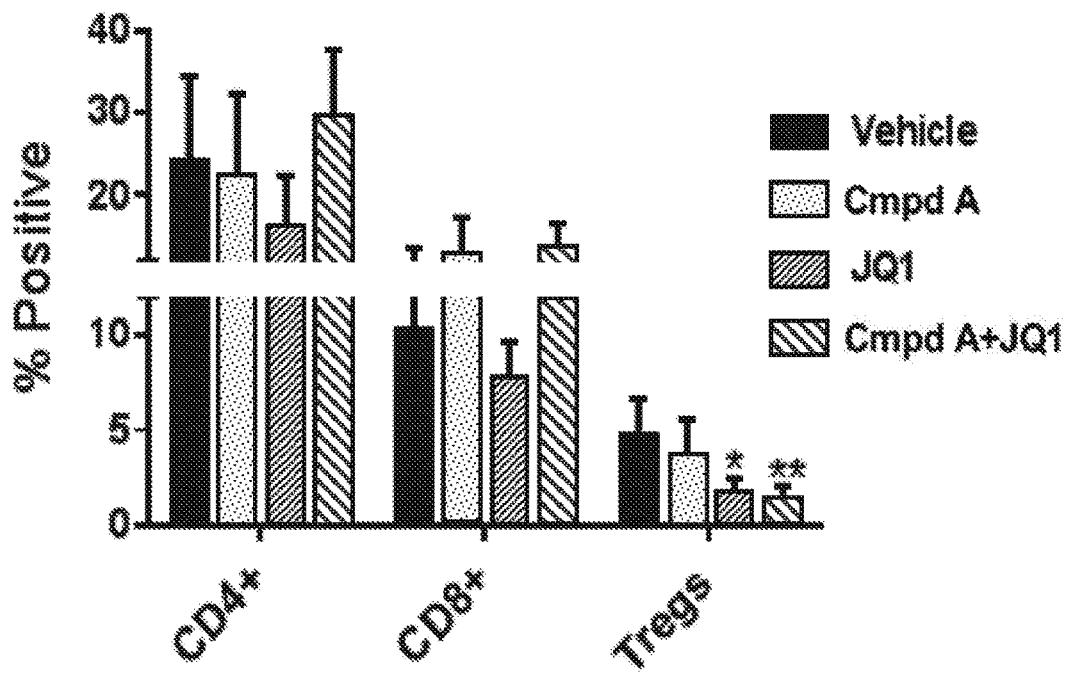
FIG. 9B shows a summary of CD4+, CD8+, and CD4+Foxp3+(Tregs) cell populations in the tumors of KP mice that were treated with JQ1 and/or Compound A. Data are mean±SEM of 4-8 mice per group.
Figure 9C:
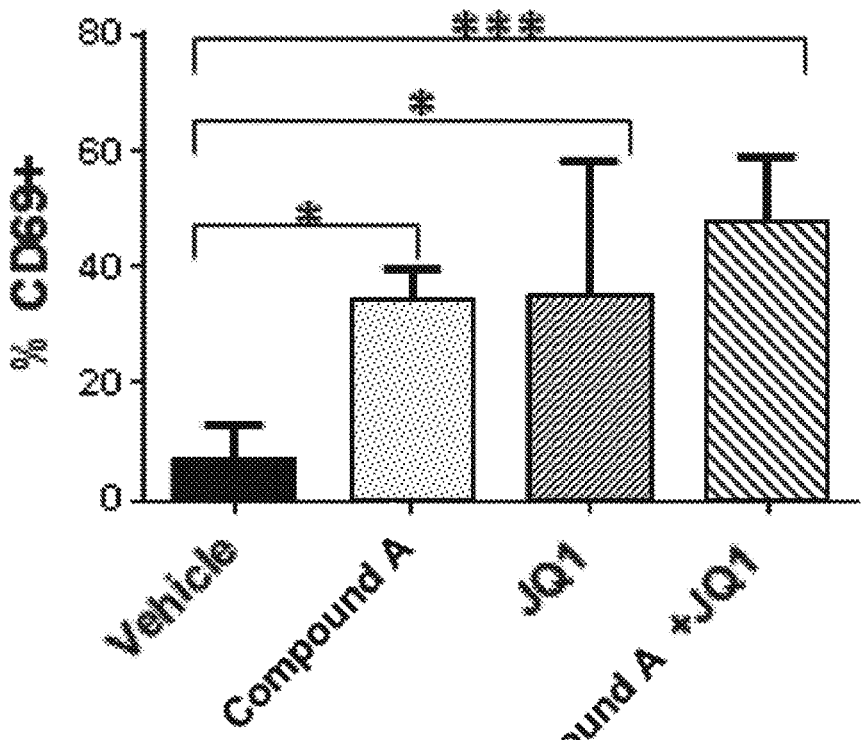
FIG. 9C shows the percentage of CD8+ T cells that expressed CD69 within tumor-infiltrating leukocytes. Data are mean±SEM of 4-8 mice per group.
Figure 9D:
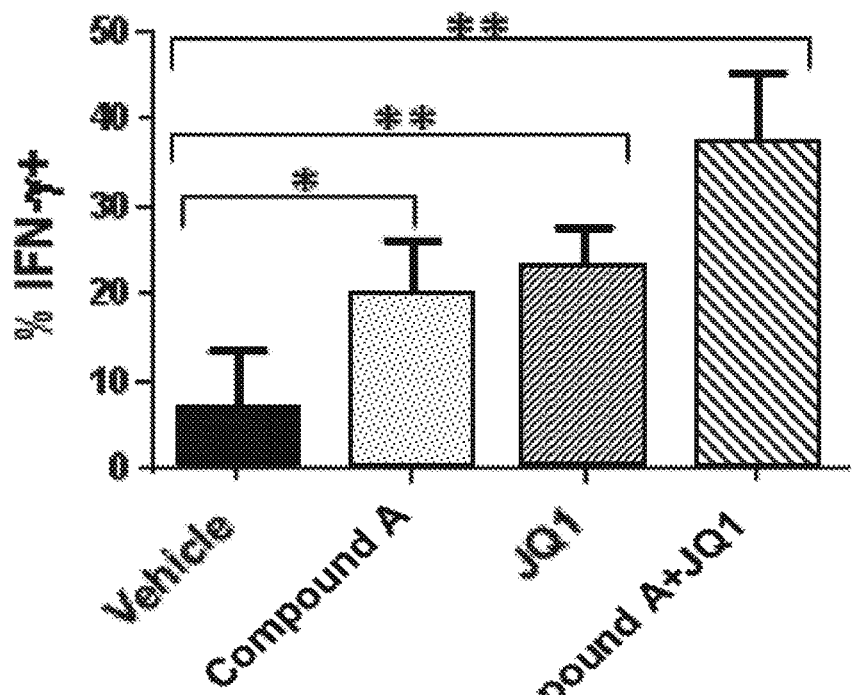
FIG. 9D shows the percentage of CD8+ T cells within tumor-infiltrating leukocytes that secreted IFN-γ based on mean fluorescent intensity following ex-vivo stimulation. Data are mean±SEM of 4-8 mice per group.
Figure 9E:
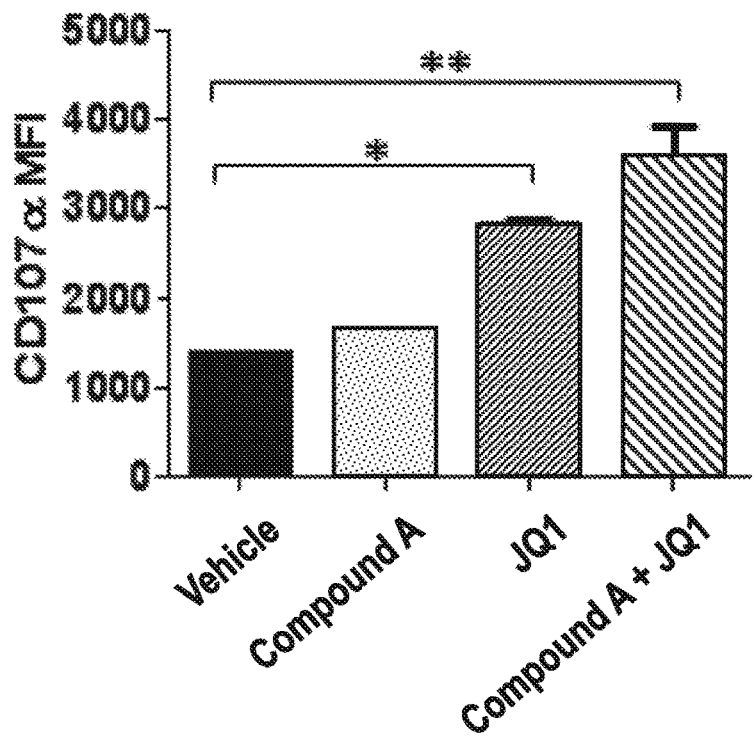
FIG. 9E shows the percentage of expressed CD107a based on mean fluorescent intensity following ex-vivo stimulation. Data are mean±SEM of 4-8 mice per group.
Figure 9F:
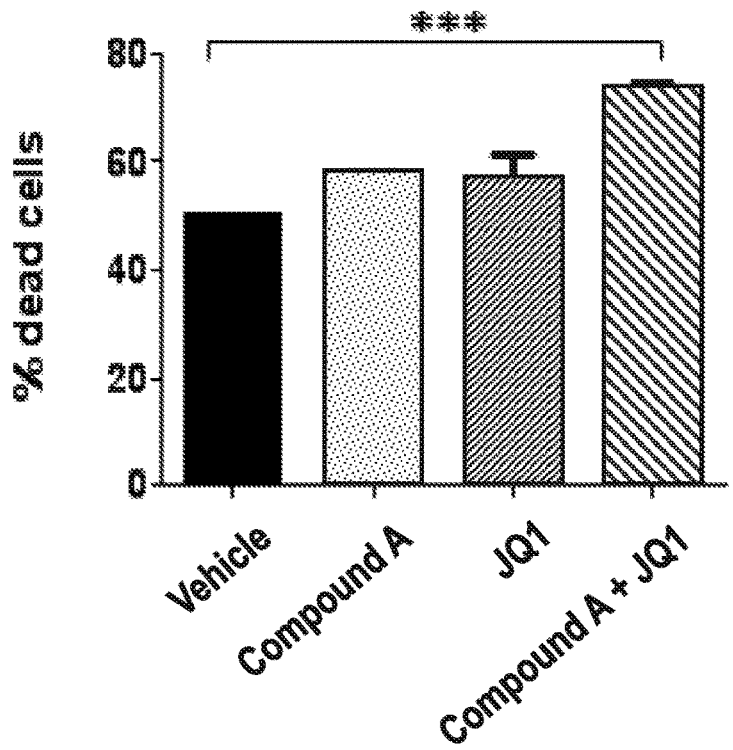
FIG. 9F shows the percentage of dead EpCam+ tumor cells as determined by populations that stained positive for live/dead discrimination dye.
Figure 9G:
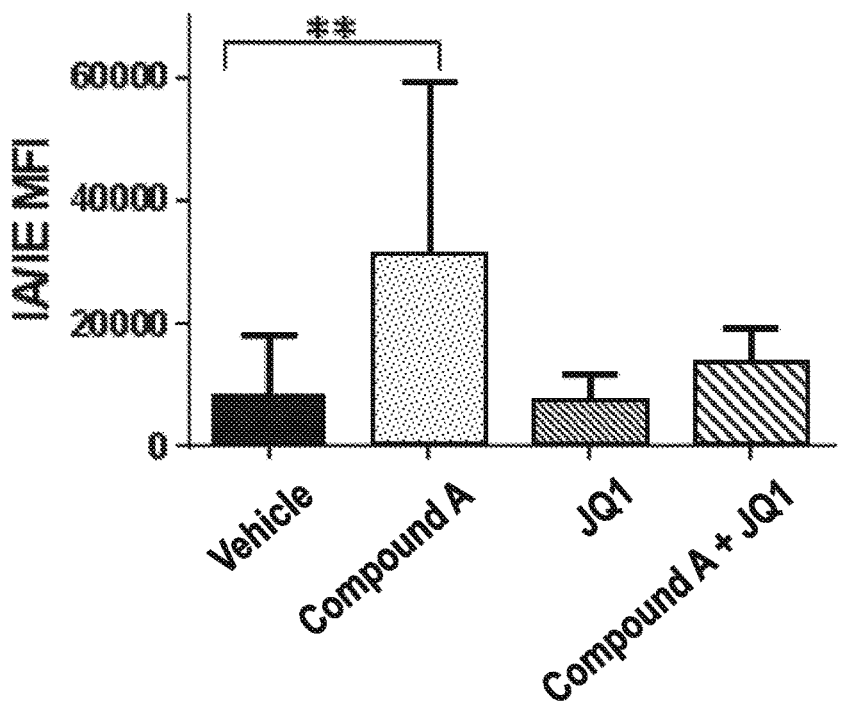
FIG. 9G shows a summary of expression levels of MHC class II on TAMs in the tumors of treated mice. Control mice received vehicle alone. Data are mean±SEM of 4-8 mice per group.
Figure 9H:
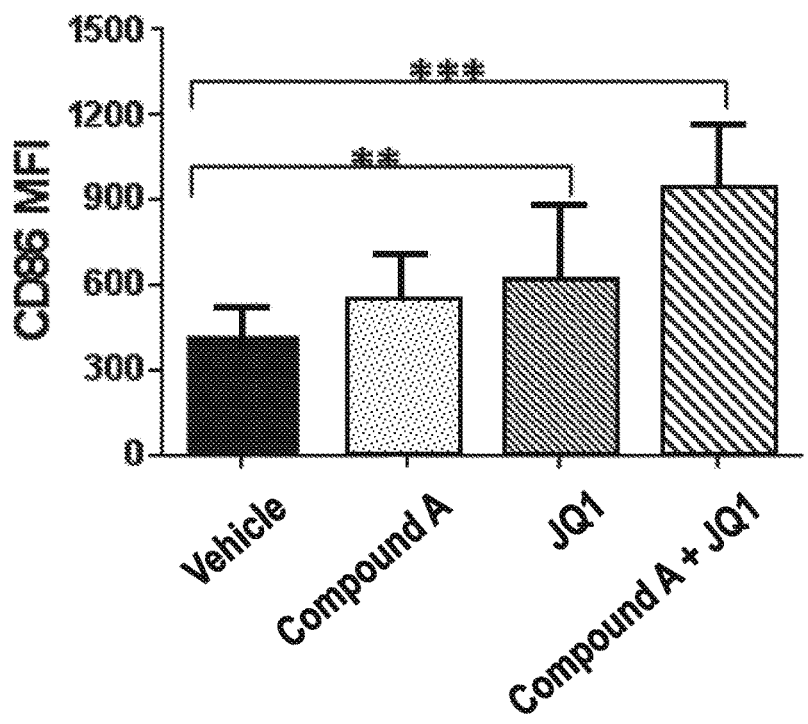
FIG. 9H shows a summary of expression levels of CD86 on TAMs in the tumors of treated mice. Control mice received vehicle alone. Data are mean±SEM of 4-8 mice per group.

Immune profiling of the tumor nodules further revealed that relative to the single agent treatments, lymphoid cells infiltrating tumors of KP mice treated with the combination of the two agents harbored significantly higher CD8:Treg ratios presumably as a result of highly reduced Treg fractions (FIGS. 9A and 9B). For immune profiling, cohorts of mice were sacrificed after 4-6 weeks of treatment and tumor cell suspensions were subjected to FACS analysis. The CD8+ T cells were more activated as evidenced by increased expression of CD69 (FIG. 9C). In addition, immune cells isolated from tumors of mice treated with indicated drugs were stimulated ex-vivo for 6 hours in the presence of golgi plug. These tumor-infiltrating CD8+ T cells demonstrated enhanced capacity to secrete the effector cytokine IFN-γ as well as increased degranulation as indicated by CD107a staining (FIGS. 9D and 9E). Cell suspensions generated from tumor nodules excised from mice that were treated with JQ1 and/or Compound A that were sorted into three populations: CD25-CD3+ T cells, CD45-Epcam+ tumor cells, and CD11b$^{lo}$CD11c+ TAMs. Equivalent numbers of each of these populations were co-cultured for two days in the presence of tumor cell lysate. When equivalent numbers of T cells, TAMs, and EpCam+ tumor cells sorted from tumor nodules of Compound A and/or JQ1-treated mice were co-cultured together along with tumor cell lysate, a higher proportion of the tumor cell death was observed in the presence of T cells isolated from the tumors of dual agent-treated mice (FIG. 9F). This demonstrated that the combination treatment results in greater tumor killing potential of tumor infiltrating T cells. With respect to the TAMs, Compound A treatment, either alone or in combination with JQ1, markedly promoted the up-regulation of MHC class II molecules and CD86 (FIGS. 9G and 9H). Taken together, these findings demonstrated that the HDAC6 selective inhibitor Compound A in combination with the bromodomain inhibitor JQ1 had immune-modulatory effects that synergized to potentiate robust immune-mediated anti-tumor response. That is, a BET bromodomain inhibitor (JQ1) with HDAC6 selective inhibitor (Compound A) enhanced immune-dependent suppression of tumor growth.

Example 10: Other Methods

Mice

Genetically engineered mice harboring $Kras^{+/LSL-G12D}Trp53^{L/L}$ (KP) or $EGFR^{LSL-T790M/L858R}$ (TL) have been previously described (DuPage, M. A. L. Dooley, and T. Jacks, *Conditional mouse lung cancer models using adenoviral or lentiviral delivery of Cre recombinase*. Nat Protoc, 2009. 4(7): p. 1064-72). For lung tumor induction, mice received 1×10⁶ cfu cre-encoding adenovirus intranasally at 5-6 weeks of age. Tumor formation (typically 6-8 weeks post inoculation) and volume was confirmed by MRI and was quantified using the 3D-slicer software. C57BL/6 mice were purchased from Taconic Farms (Bejing, China). All mice were maintained under specific pathogen-free conditions.

Drugs, Antibodies, and Reagents

Compound A (ricolinostat) was provided by Acetylon Pharmaceuticals (Boston, Mass.). Compound A was formulated in 10% DMSO and 90% of 5% dextrose, and was administered to mice at 50 mg/kg I.P. daily. Tubastatin was obtained from APExBIO (Houston, Tex.). Tubastatin was formulated in 10% DMSO and 90% of 0.9% saline, and was administered to mice at 25 mg/kg I.P. daily. JQ1 was kindly provided by James Bradner (Dana Farber Cancer Institute, Boston, Mass.). JQ1 was formulated in 10% DMSO and 90% of 10% 2-hydroxylpropyl β-cyclodextrin (Sigma), and was administered to mice at 25 mg/kg I.P. daily. Vehicle control was prepared by diluting DMSO into the related drug vehicle. Anti-CD4 (GK1.5), anti-CD8 (53-6.72) and Rat IgG (LTF-2) were purchased from BioXcell. Mice were first administered antibodies for two consecutive days before treatment with a combination of Compound A and JQ1, and then were dosed twice per week at 400 ug/mouse/time I.P. with antibodies. Depletion of relevant cell types was confirmed by flow cytometry one day after the second dose using peripheral blood obtained from the tail vein. Mouse and human antibodies used in the study for flow cytometric analyses were purchased from Biolegend, Ebioscience, and BD pharmingen. Recombinant human cytokines IL-2, IL-4, and GM-CSF were all purchased from peprotech (NJ).

Tumor Profiling and Flow Cytometry

Figure 10:
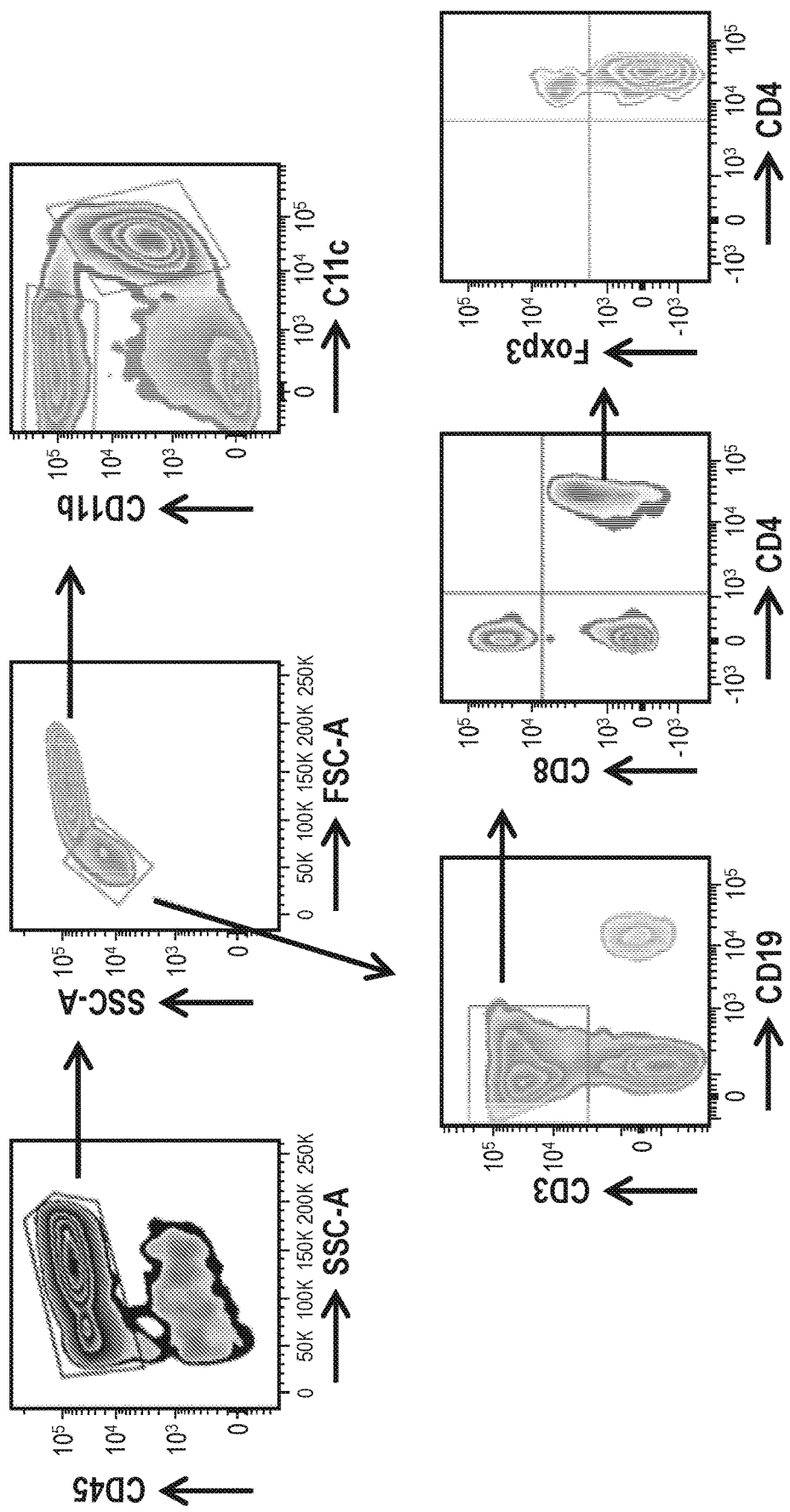
FIG. 10 shows the gating strategy for FACS analyses.

To generate cell suspensions, tumor nodules were excised from lungs of KP and TL mice and cut into small pieces followed by further dissociation in RPMI-1640/5% FBS buffer containing 100 U/ml collagenase type IV (Invitrogen) and 50 ug/ml DNAse I (Roche) for 45 minutes at 37° C. After incubation, cells were treated with red blood cell lysis buffer and were filtered through a 70 µm cell strainer. After centrifugation, cell pellet was re-suspended in 1×PBS/2% FBS. Cells were counted, and ~0.5-1×10⁶ cells were stained for surface markers in PBS+2% FBS for 15 minutes at 4° C. Intracellular staining was performed for Foxp3, Ki67, CTLA-4, and Bcl-2, using the Foxp3 staining buffer according to the manufacturer's instructions while the cytofix/cytoperm kit (BD Bioscience) was used for intracellular cytokine staining. Briefly, cells were stained for surface markers including CD4, CD8, CD3, followed by intracellular staining with PE-conjµgated anti-IFN-γ, BV421-conjµgated anti-TNF-α, APC-conjugated IL-2, FITC-conjugated Perforin and CD107a (where indicated), or isotype-matched mAbs after permeabilization and fixation. In all stained samples, dead cells were excluded using Live/Dead Fixable dead cell staining kit (Invitrogen). Cells were acquired on the LSR Fortessa (BD Biosciences) and were analyzed with the flowjo software (Treestar). Gating strategy for FACS analysis is shown in FIG. 10.

Cell Purification and In Vitro Studies

Peripheral blood mononuclear cells (PBMCs) were isolated by Ficoll gradient from fresh or frozen blood samples obtained from healthy donors and consented patients under IRB-approved institutional protocols. When frozen, PBMCs were thawed and were rested in 10% complete medium (RPMI 1640 supplemented with 10% pooled human serum, 100 U/mL penicillin, 100 U/mL streptomycin, and 2 mM L-glutamine) at 37° C. for 6 hours after which cells (0.5× 10⁶) were cultured with Compound A (2.5 µm), entinostat (2.5 µm) or JQ1 (1 µm) for 24 or 72 hours. Cells were then washed and were subjected to phenotypic analysis by FACS. In some experiments, these cultures were performed with purified CD14+ monocytes or CD3+ T cells after purifications from whole PBMCs.

For T cell proliferation assays, T cells were isolated from PBMCs by positive selection using T cell enrichment kit (Miltenyi Biotec) following the manufacturer's instructions. Cells were typically ~90% pure. Purified T cells were then labeled with 2.511M CFSE or cell trace violet (CTV) at 37° C. for 7 min. Cells were washed three times with RPMI+ 10% FBS, were counted, and were used as responder cells. Purified CD14+ cells isolated from patient PBMCs by positive selection using CD14 microbeads were cultured with Compound A or entinostat for 24 hours after which cells were washed three times before co-culture with allogeneic T cells in mixed lymphocyte reactions.

For intracellular cytokine detection assays, immune cells from tumors of treated or control mice were obtained after ficoll gradient separation as previously described. 1×10⁶ cells were cultured with PMA (50 ng) and Ionomycin (500 ng) for 6 hours at 37° C., and GolgiPlµg (BD Pharmingen) was added for the last 5 hours of culture. For equivalent assays utilizing human PBMCs, 0.5×10⁶ cells were similarly stimulated prior to analysis.

Single Cell RNA Sequencing of Tumor-Infiltrating TAMs and T Cells

Tumor-associated macrophages (TAMs; CD45+CD11c+ CD11b$^{lo}$) and CD45+CD3+CD25$^{lo/-}$ T cells were sorted into 96-well plates containing 50 µl of 1×PBS with Recombinant Ribonuclease Inhibitor (Life Technologies) isolated from tumor tissues by FACS sorting. Briefly, tumor cell suspensions were incubated with live/dead fixable dye after FcγR blocking and subsequently stained with antibodies against CD45, CD3, CD8, CD11b, and CD11c. Smart-Seq2 libraries were prepared by the Broad Technology Labs and sequenced by the Broad Genomics Platform.

Statistical Analysis

Statistical significance was evaluated by Student's t test for comparisons between two groups or one-way Anova for multi-group comparisons using GraphPad Prism software. P<0.05 values were considered statistically significant (*), P<0.01 values were considered very significant (), and P<0.001 values were considered highly significant (*).

Summary of Above Examples

The experiments above demonstrate that entinostat, a Class 1 HDAC-selective agent, only partially reproduced some of the effects of Compound A (HDAC6 selective with weak activity against HDAC1/2/3). Thus, the observed immunomodulatory effects of Compound A were likely a unique and unexpected feature of its relative inhibitory activities on HDAC6 and Class 1 HDACs.

Compound A has the potential to fine-tune immunological events associated with antigen presentation. In a pathological or disease setting, immature professional antigen presenting cells (APCs) must "pick up," process, and present relevant antigens while undergoing phenotypic changes to a more mature state. When present in such state, they possess enhanced antigen-presenting and T cell priming capability due to an increase in their expression of MHC class II and co-stimulatory molecules. The increased expression of MHC class II as well as co-stimulatory molecule CD86 as observed on tumor-associated macrophages (TAMs) upon Compound A treatment in lung tumor-bearing mice was thus consistent with the notion that Compound A served as a unique modulatory agent promoting phenotypic changes that favored improved delivery of co-stimulatory signals and presentation of antigens. In support of this point was the finding that Compound A-exposed CD14+ monocytes from patient PBMCs were better at driving allo-reactive T cell proliferation. This is largely a function of the degree of stimulation derived from T-cell engagement of foreign MHC molecules as well as co-stimulation present on APCs. Furthermore, the observed increase in phospho-STAT3 and CD69 expression on Compound A-exposed T cells also suggested that it may have a direct priming effect on T cells in a manner dependent on STAT3 activation. Indeed, activation of STAT3 has been shown to induce CD69 expression, and, hence, T cell activation in an alloreactive T cell model. Such activating effects can be beneficial for amplification of TCR-induced, antigen-driven T cell priming especially in the context of tumor-associated antigens.

The administration of Compound A can facilitate improved T cell priming in cancer patients. This notion was supported by the increased activation and enhanced effector function of tumor-infiltrating CD8+ T cells observed in tumor-bearing mice that were treated with Compound A. Although by itself it was not robust in dampening tumor growth in the GEM model of NSCLC, Compound A resulted in remarkable T-cell mediated anti-tumor efficacy when coupled with JQ1.

As CD4+FOXP3+T regulatory cells accumulate in many solid cancers, agents that have the potential to target these cells can offer therapeutic benefits. As disclosed, a combination of an HDAC6 selective inhibitor (Compound A) and a BET inhibitor (JQ1) treatment reduced fractions of Treg cells but not conventional T cells within the tumor microenvironment in treated mice. This suggested that Treg cells can be more susceptible to epigenetic modifications than their conventional T cell counterparts. Although levels of Foxp3 were diminished on Treg cells spared by Compound A in vitro, this effect was only moderate in vivo. JQ1 on the other hand, exhibited a more profound effect evidenced by reduced Foxp3 expression level, and function of the Treg cells in vitro in addition to a more substantial reduction of Treg proportions in tumors of JQ1 treated mice. Compound A and JQ1 can preferentially modulate FOXP3 gene expression, or stability of the protein, and, hence, overall survival and activity of these cells. These effects are supported by existing reports demonstrating that certain HDAC inhibitors affect Treg biology as acetylation status of histones by HATs/HDACs are known to affect FOXP3 gene expression and stability. Variations in gene loci or protein region targeted by different HDACs can affect Treg activity in response to different HDAC inhibitors. In addition, the inflammatory context associated with different disease states can dictate how certain HDAC inhibitors effect their activity.

Without intending to be bound by any theory, Compound A can play a pleiotropic role on immune cells and can function by reducing Treg cell numbers, increasing transient TCR-independent activation of T cells, and promoting APC function. JQ1 on the other hand further disrupts Treg suppressive activity, which is considered a key mechanism impeding immune-mediated anti-tumor response. JQ1 synergized with Compound A, further reducing Treg proportions and disrupting suppressive function of residual Tregs present in the tumor bed. The net effect is promotion of leukocyte-orchestrated anti-tumor response by way of optimizing antigen delivery, increasing co-stimulatory signals while lowering inhibitory cellular mechanisms. The abrogation of tumor growth arrest seen under Compound A and JQ1 therapy upon T cell depletion demonstrated that T cells were key players in the efficacy of combinatorial treatment in this model.

The combination of Compound A and JQ1 led to a robust immune-mediated anti tumor effect in lung tumors driven by different mutation genotypes, which prolonged the survival of tumor-bearing mice. The previously undescribed immune-modulatory effects of these two agents support a rational pharmaceutical combination comprising HDAC6 selective inhibitor and a BET inhibitor for therapeutic interventions in cancer, especially lung adenocarcinomas. Additionally, the dosages used herein are consistent with current clinical application. No signs of toxicity were observed. Compound A and JQ1 can be utilized as "hybrid" therapies that harness not just their direct anti-tumor effects but also the indirect effects via peripheral re-shaping of immune cell dynamics and function, converging to foster strong anti-cancer benefit.

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the disclosure described herein. Such equivalents are intended to be encompassed by the following claims.

What is claimed is:

1. A method for treating lung cancer in a subject in need thereof, comprising administering to the subject a therapeutically effective amount of a histone deacetylase 6 (HDAC6) selective inhibitor and a therapeutically effective amount of a bromodomain and extraterminal (BET) inhibitor, wherein the HDAC6 selective inhibitor is a compound of Formula I:

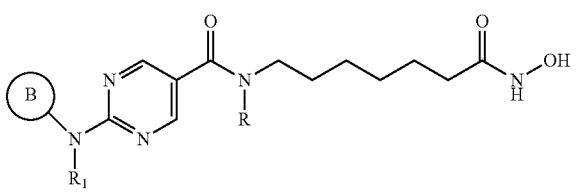

(I)

or a pharmaceutically acceptable salt thereof,
wherein,
ring B is aryl or heteroaryl;
$R_1$ is an aryl or heteroaryl, each of which may be optionally substituted by OH, halo, or $C_{1-6}$-alkyl; and
R is H or $C_{1-6}$-alkyl.

2. The method of claim 1, wherein the compound of Formula I is:

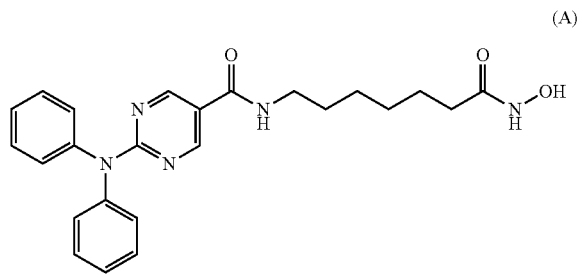 [SMILES: O=C(CCCCCCNC(=O)c1cnc(N(c2ccccc2)c2ccccc2)nc1)NO]

(A)

or a pharmaceutically acceptable salt thereof.

3. The method of claim 1, wherein the compound of Formula I is:

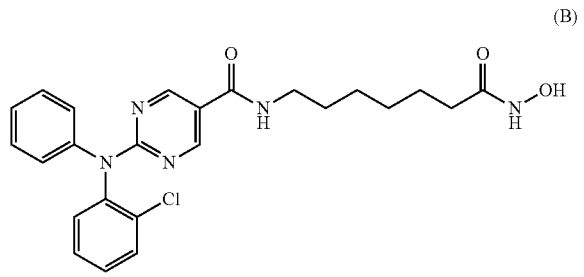 [SMILES: O=C(CCCCCCNC(=O)c1cnc(N(c2ccccc2)c2ccccc2Cl)nc1)NO]

(B)

or a pharmaceutically acceptable salt thereof.

4. The method of claim 1, wherein the BET inhibitor is selected from the group consisting of;
N-(4-(2,4-difluorophenoxy)-3-(6-methyl-7-oxo-6,7-dihydro-1H-pyrrolo[2,3-c]pyridin-4-yl)phenyl)ethanesulfonamide (ABBV-075),
((S)-7,8-dimethoxy-N,4-dimethyl-1-(4-(4-methylpiperazin-1-yl)phenyl)-4,5-dihydro-3H-benzo[d][1,2]diazepine-3-carboxamide) (BAY1238097),
3-(1,4-dimethyl-1H-1,2,3-triazol-5-yl)-α,α-dimethyl-5-[(S)-phenyl(tetrahydro-2H-pyran-4-yl)methyl]-5H-pyrido[3,2-b]indole-7-methanol (BMS986158),
N-[6-(3-methanesulfonamido-4-methylphenyl)-3-methyl-[1,2,4]triazolo[4,3-b]pyridazin-8-yl]carbamate (bromosporine),
2-[2-(3-chloro-4-methoxyphenyl)ethyl]-5-(dimethyl-1,2-oxazol-4-yl)-1-[(2S)-2-(morpholin-4-yl)propyl]-1H-1,3-benzodiazole (CBP30),
(6S)-4-(4-chlorophenyl)-2,3,9-trimethyl-6H-thieno[3,2-f][1,2,4]triazolo[4,3-a][1,4]diazepine-6-acetamide (CPI-203),
2-[(4S)-6-(4-chlorophenyl)-1-methyl-4H-[1,2]oxazolo[5,4-d][2]benzazepin-4-yl]acetamide (CPI-0610),
[(2S)-5-(cyclobutyloxy)-3,4-dihydro-2-methyl-6-[1-(4-piperidinyl))-1H-pyrazol-4-yl]-1(2H)-quinolinyl]cyclopropylmethanone (FT-1101),
7-(3,5-dimethyl-1,2-oxazol-4-yl)-8-methoxy-1-[(1R)-1-pyridin-2-ylethyl]-3H-imidazo[4,5-c]quinolin-2-one (GSK2820151),
7,3,5-dimethyl-4-isoxazolyl-1,3-dihydro-8-methoxy-1-[1R-1-(2-pyridinyl)ethyl]-2H-imidazo[4,5-c]quinolin-2-one (I-BET151),
4-[(2S,4R)-1-acetyl-4-[(4-chlorophenyl)amino]-1,2,3,4-tetrahydro-2-methyl-6-quinolinyl]-benzoic acid (I-BET726),
(S)-2-(6-(4-chlorophenyl)-8-methoxy-4H-benzo[f][1,2,4]triazolo[4,3-a][1,4]diazepin-4-yl)-N-ethylacetamide (I-BET-762),
(S)-6-(3,5-dimethylisoxazol-4-yl)-3-(pyridin-2-yl)-3,4-dihydro-5-oxa-1,2a-diazaacenaphthylen-2(1H)-one (INCB054329),
8-(6,7-dihydro-6-methyl-7-oxo-1H-pyrrolo[2,3-c]pyridin-4-yl)-2,2,4-trimethyl-6-(methylsulfonyl)-2H-1,4-benzoxazin-3(4H)-one (INCB057643),
3-(4-(2-(5-(3,5-dimethylisoxazol-4-yl)-1-(2-morpholinoethyl)-1H-benzo[d]imidazol-2-yl)ethyl)phenoxy)-N,N-dimethylpropan-1-amine (ISOX DUAL),
(6S)-4-(4-chlorophenyl)-2,3,9-trimethyl-6H-thieno[3,2-f][1,2,4]triazolo[4,3-a][1,4]diazepine-6-acetic acid, 1,1-dimethylethyl ester (JQ1),
2-(4-morpholinyl)-8-phenyl-4H-1-benzopyran-4-one (LY294002),
8-phenyl-2-(1-piperazinyl)-4H-1-benzopyran-4-one, dihydrochloride (LY303511),
(E)-4-[2-(2-amino-4-hydroxy-5-methylphenyl)diazenyl]-N-2-pyridinylbenzenesulfonamide (MS436),
4-chlorophenyl)-N-(4-hydroxyphenyl)-2,3,9-trimethyl-, (6S)-6H-Thieno[3,2-f][1,2,4]triazolo[4,3-a][1,4]diazepine-6-acetamide (MK8628),
4-bromo-N-(2,3-dihydro-6-methoxy-1,3-dimethyl-2-oxo-1H-benzimidazol-5-yl)-2-methyl-benzenesulfonamide (OF-1),
3-(3,5-dimethyl-4-isoxazolyl)-5-hydroxy-α-phenylbenzenemethanol (OXF BD 02),
2-methoxy-N-(3-methyl-2-oxo-1,2,3,4-tetrahydroquinazolin-6-yl)benzenesulfonamide (PFI-1),
(2E)-1-(2-hydroxyphenyl)-3-[(1R,4R)-5-(2-pyridinyl)-2,5-diazabicyclo[2,2,1]hept-2-yl]-2-propen-1-one (PFI-3),
2-methoxy-N-(3-methyl-2-oxo-1,2,3,4-tetrahydroquinazolin-6-yl)benzenesulfonamide (PF-6405761),
2-[4-(2-hydroxyethoxy)-3,5-dimethylphenyl]-5,7-dimethoxy-4(3H)-quinazolinone (RVX-208),
(S)-2-(4-(4-chlorophenyl)-2,3,9-trimethyl-6H-thieno[3,2-f][1,2,4]triazolo[4,3-a][1,4]diazepin-6-yl)acetamide (TEN-010), and
4-acetyl-N-[5-[(diethylamino)sulfonyl]-2-hydroxyphenyl]-3-ethyl-5-methyl-1H-pyrrole-2-carboxamide (XD 14),
or a pharmaceutically acceptable salt thereof.

5. The method of claim 4, wherein the BET inhibitor is JQ1:

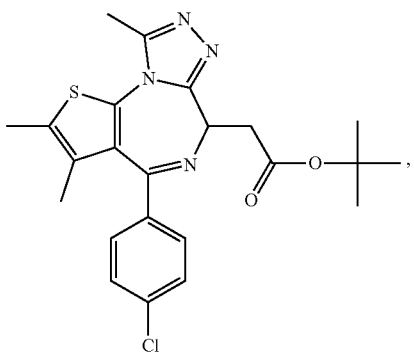

(JQ1)

or a pharmaceutically acceptable salt thereof.

6. The method of claim 1, wherein the HDAC6 selective inhibitor or the BET inhibitor are administered at a sub-therapeutic dose.

7. The method of claim 1, wherein the HDAC6 selective inhibitor induces apoptosis of cancer cells.

8. The method of claim 1, wherein the lung cancer is non-small cell lung cancer, small cell lung cancer, or lung carcinoid tumor.

9. The method of claim 1, wherein the HDAC6 selective inhibitor and the BET inhibitor are together formulated as a single formulation or the HDAC6 selective inhibitor and the BET inhibitor are each formulated as separate formulations.

10. The method of claim 1, wherein the HDAC6 selective inhibitor and the BET inhibitor are administered at substantially the same time or the HDAC6 selective inhibitor and the BET inhibitor are administered at different times.

11. The method of claim 1, wherein the cancer is resistant or refractory cancer.

* * * * *